US011158422B1

(12) United States Patent
Wilson et al.

(10) Patent No.: US 11,158,422 B1
(45) Date of Patent: Oct. 26, 2021

(54) MEASUREMENT AND TESTING SYSTEM THAT INCLUDES A DATA PROCESSING DEVICE CONFIGURED TO SYNCHRONIZE FIRST AND SECOND SIGNALS BY USING TIME-DELAYED VALUES OR RECONSTRUCTED VALUES OCCURRING COINCIDENT WITH A TRANSITION OF A DIGITAL TIME REFERENCE SIGNAL

(71) Applicant: Bertec Corporation, Columbus, OH (US)

(72) Inventors: Todd Christopher Wilson, Columbus, OH (US); Necip Berme, Worthington, OH (US); Jan Jakub Ober, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 17/068,181

(22) Filed: Oct. 12, 2020

Related U.S. Application Data

(60) Division of application No. 16/450,377, filed on Jun. 24, 2019, now Pat. No. 10,803,990, which is a continuation-in-part of application No. 15/822,135, filed on Nov. 25, 2017, now Pat. No. 10,331,324, which is a continuation-in-part of application No. 14/953,505, filed on Nov. 30, 2015, now Pat. No. 9,829,311, which is a continuation-in-part of application No. 14/556,656, filed on Dec. 1, 2014, now Pat. No. 9,200,897, which is a continuation-in-part of application No. 14/042,332, filed on Sep. 30, 2013, now Pat. No. 8,902,249, which is a continuation-in-part of application No. 13/726,065, filed on Dec. 22, 2012, now Pat. No. 8,643,669.

(51) Int. Cl.
*G16H 40/63* (2018.01)

(52) U.S. Cl.
CPC .................................. *G16H 40/63* (2018.01)

(58) Field of Classification Search
None
See application file for complete search history.

(56) References Cited

U.S. PATENT DOCUMENTS

| | | | |
|---|---|---|---|
| 5,428,769 A | 6/1995 | Glaser et al. |
| 6,038,488 A | 3/2000 | Barnes et al. |
| 6,113,237 A | 9/2000 | Ober et al. |
| 6,152,564 A | 11/2000 | Ober et al. |
| 6,295,878 B1 | 10/2001 | Berme |
| 6,354,155 B1 | 3/2002 | Berme |
| 6,389,883 B1 | 5/2002 | Berme et al. |
| 6,936,016 B2 | 8/2005 | Berme et al. |
| 7,389,144 B1 | 6/2008 | Osorio et al. |
| 8,181,541 B2 | 5/2012 | Berme |
| 8,315,822 B2 | 11/2012 | Berme et al. |
| 8,315,823 B2 | 11/2012 | Berme et al. |
| D689,388 S | 9/2013 | Berme |
| D689,389 S | 9/2013 | Berme |
| 8,543,540 B1 | 9/2013 | Wilson et al. |
| 8,544,347 B1 | 10/2013 | Berme |
| 8,643,669 B1 | 2/2014 | Wilson et al. |
| 8,700,569 B1 | 4/2014 | Wilson et al. |
| 8,704,855 B1 | 4/2014 | Berme et al. |
| 8,764,532 B1 | 7/2014 | Berme |
| 8,847,989 B1 | 9/2014 | Berme et al. |
| D715,669 S | 10/2014 | Berme |
| 8,902,249 B1 | 12/2014 | Wilson et al. |
| 8,915,149 B1 | 12/2014 | Berme |
| 9,032,817 B2 | 5/2015 | Berme et al. |
| 9,043,278 B1 | 5/2015 | Wilson et al. |
| 9,066,667 B1 | 6/2015 | Berme et al. |
| 9,081,436 B1 | 7/2015 | Berme et al. |
| 9,168,420 B1 | 10/2015 | Berme et al. |
| 9,173,596 B1 | 11/2015 | Berme et al. |
| 9,200,897 B1 | 12/2015 | Wilson et al. |
| 9,277,857 B1 | 3/2016 | Berme et al. |
| D755,067 S | 5/2016 | Berme et al. |
| 9,404,823 B1 | 8/2016 | Berme et al. |
| 9,414,784 B1 | 8/2016 | Berme et al. |
| 9,468,370 B1 | 10/2016 | Shearer |
| 9,517,008 B1 | 12/2016 | Berme et al. |
| 9,526,443 B1 | 12/2016 | Berme et al. |
| 9,526,451 B1 | 12/2016 | Berme |
| 9,558,399 B1 | 1/2017 | Jeka et al. |
| 9,568,382 B1 | 2/2017 | Berme et al. |
| 9,622,686 B1 | 4/2017 | Berme et al. |
| 9,763,604 B1 | 9/2017 | Berme et al. |
| 9,770,203 B1 | 9/2017 | Berme et al. |
| 9,778,119 B2 | 10/2017 | Berme et al. |
| 9,814,430 B1 | 11/2017 | Berme et al. |
| 9,829,311 B1 | 11/2017 | Wilson et al. |
| 9,854,997 B1 | 1/2018 | Berme et al. |
| 9,916,011 B1 | 3/2018 | Berme et al. |
| 9,927,312 B1 | 3/2018 | Berme et al. |

(Continued)

OTHER PUBLICATIONS

BalanceCheck Screener—Protocol Guide, Bertec Corporation, Version 1.1.0, last updated Mar. 2012.

(Continued)

*Primary Examiner* — G Steven Vanni
(74) *Attorney, Agent, or Firm* — The Law Office of Patrick F. O'Reilly III, LLC

(57) ABSTRACT

A measurement and testing system is disclosed herein. The measurement and testing system includes a first measurement device and a second measurement device and a data processing device operatively coupled to the first measurement device and the second measurement device. In one or more embodiments, the data processing device is configured to synchronize each of a first plurality of data values from the first measurement device with each of a second plurality of data values from the second measurement device by determining which first timestamps associated with the first plurality of data values correspond to second timestamps associated with the second plurality of data values. In one or more other embodiments, the data processing device is configured to compute time-delayed values of one or more first measurement signals from a first measurement device using a predetermined time delay.

11 Claims, 57 Drawing Sheets

(56) References Cited

U.S. PATENT DOCUMENTS

| | | | |
|---|---|---|---|
| 10,010,248 B1 | 7/2018 | Shearer | |
| 10,010,286 B1 | 7/2018 | Berme et al. | |
| 10,085,676 B1 | 10/2018 | Berme et al. | |
| 10,117,602 B1 | 11/2018 | Berme et al. | |
| 10,126,186 B2 | 11/2018 | Berme et al. | |
| 10,216,262 B1 | 2/2019 | Berme et al. | |
| 10,231,662 B1 | 3/2019 | Berme et al. | |
| 10,264,964 B1 | 4/2019 | Berme et al. | |
| 10,331,324 B1 | 6/2019 | Wilson et al. | |
| 10,342,473 B1 | 7/2019 | Berme et al. | |
| 10,390,736 B1 | 8/2019 | Berme et al. | |
| 10,413,230 B1 | 9/2019 | Berme et al. | |
| 10,463,250 B1 | 11/2019 | Berme et al. | |
| 10,527,508 B2 | 1/2020 | Berme et al. | |
| 10,555,688 B1 | 2/2020 | Berme et al. | |
| 10,646,153 B1 | 5/2020 | Berme et al. | |
| 10,722,114 B1 | 7/2020 | Berme et al. | |
| 10,736,545 B1 | 8/2020 | Berme et al. | |
| 10,765,936 B2 | 9/2020 | Berme et al. | |
| 10,803,990 B1 | 10/2020 | Wilson et al. | |
| 2002/0057380 A1 | 5/2002 | Matey | |
| 2002/0178008 A1 | 11/2002 | Reynar | |
| 2003/0216656 A1 | 11/2003 | Berme et al. | |
| 2004/0127337 A1 | 7/2004 | Nashner | |
| 2004/0260427 A1 | 12/2004 | Wimsatt | |
| 2006/0265249 A1 | 11/2006 | Follis et al. | |
| 2008/0183981 A1 | 7/2008 | Tannai | |
| 2008/0228110 A1 | 9/2008 | Berme | |
| 2009/0062092 A1 | 3/2009 | Mortimer et al. | |
| 2009/0251130 A1 | 10/2009 | Lund | |
| 2011/0277562 A1 | 11/2011 | Berme | |
| 2012/0123701 A1 | 5/2012 | Drueding et al. | |
| 2012/0266648 A1 | 10/2012 | Berme et al. | |
| 2012/0271565 A1 | 10/2012 | Berme et al. | |
| 2013/0018282 A1 | 1/2013 | Mainini et al. | |
| 2013/0171601 A1 | 7/2013 | Yuasa et al. | |
| 2015/0096387 A1 | 4/2015 | Berme et al. | |
| 2016/0245711 A1 | 8/2016 | Berme et al. | |
| 2016/0334288 A1 | 11/2016 | Berme et al. | |
| 2018/0024015 A1 | 1/2018 | Berme et al. | |
| 2019/0078951 A1 | 3/2019 | Berme et al. | |
| 2020/0139229 A1 | 5/2020 | Berme et al. | |

OTHER PUBLICATIONS

BalanceCheck Trainer—Protocol Guide, Bertec Corporation, Version 1.1.0, last updated Mar. 2012.

Bertec Workbook—Program Documentation, Bertec Corporation, Version 1.1.0, last updated Mar. 2012.

Digital Acquire 4—Program Documentation, Bertec Corporation, Version 4.0.11, last updated Jul. 2012.

Bertec Force Plates, Bertec Corporation, Version 1.0.0, last updated Mar. 2012.

Author Todd Wilson, Bertec Workbook: Program Documentation, Version 1.0.0, Feb. 2010, pp. 47 Source: http://web.archive.org/web20110918144039/http://bertec.com/uploads/pdfs/manuals/Bertec%20Workbook.pdf.

First office action on the merits (Non-Final Rejection) in U.S. Appl. No. 13/726,065, dated Mar. 25, 2013.

Notice of Allowance in U.S. Appl. No. 13/726,065, dated Jul. 1, 2013.

First office action on the merits (Non-Final Rejection) in U.S. Appl. No. 14/042,332, dated Apr. 9, 2014.

Notice of Allowance in U.S. Appl. No. 14/042,332, dated Aug. 1, 2014.

First office action on the merits (Non-Final Rejection) in U.S. Appl. No. 14/556,656, dated Feb. 18, 2015.

Notice of Allowance in U.S. Appl. No. 14/556,656, dated Jul. 28, 2015.

First office action on the merits (Non-Final Rejection) in U.S. Appl. No. 14/953,505, dated Oct. 21, 2016.

Decond office action on the merits (Final Rejection) in U.S. Appl. No. 14/953,505, dated Mar. 6, 2017.

Notice of Allowance in U.S. Appl. No. 14/953,505, dated Jul. 26, 2017.

Decker et al., 2009, Foot force measurement by a force platform, BME 315 Biomechanics, 8 pages.

First office action on the merits (Non-Final Rejection) in U.S. Appl. No. 15/822,135, dated Nov. 13, 2018.

Notice of Allowance in U.S. Appl. No. 15/822,135, dated Feb. 6, 2019.

First office action on the merits (Non-Final Rejection) in U.S. Appl. No. 16/450,377, dated Nov. 19, 2019.

Notice of Allowance in U.S. Appl. No. 16/450,377, dated Jun. 15, 2020.

Lei, Ying, et al. "Algorithms for time synchronization of wireless structural monitoring sensors." Earthquake engineering & structural dynamics 34.6 (2005): 555-573.

Liu, Tao, et al. "A mobile force plate and three-dimensional motion analysis system for three-dimensional gait assessment." IEEE Sensors Journal 12.5 (2011): 1461-1467.

Waele, Stijn, and Piet MT Broersen. "Error measures for resampled irregular data." IEEE Transactions on Instrumentation and Measurement 49.2 (2000): 216-222.

338 — sqlite> SELECT DISTINCT Sessions.* FROM TestResults INNER JOIN Sessions ON TestResults.SessionGUID = Sessions.GUID WHERE Sessions.PatientGUID='4f64d052-a3f0-1499-775c-8bb1f55c0a5d' ORDER BY StartTime;

| Record Number | Patient GUID | Start Time/Date of Test |
|---|---|---|
| 1 | 4f6...a5d | 08:29:15 \| 2008/10/31 |
| 2 | 4f6...a5d | 15:39:07 \| 2008/11/10 |
| 3 | 4f6...a5d | 15:42:12 \| 2008/11/11 |
| 4 | 4f6...a5d | 13:21:42 \| 2008/11/12 |
| 5 | 4f6...a5d | 15:32:48 \| 2008/11/12 |
| 6 | 4f6...a5d | 15:59:17 \| 2008/11/13 |
| 7 | 4f6...a5d | 09:20:52 \| 2008/11/14 |
| 8 | 4f6...a5d | 15:30:19 \| 2008/11/14 |
| 9 | 4f6...a5d | 16:24:39 \| 2008/11/14 |
| 10 | 4f6...a5d | 10:12:19 \| 2008/11/18 |

See Fig. 25 for Continuation

MEASUREMENT AND TESTING SYSTEM THAT INCLUDES A DATA PROCESSING DEVICE CONFIGURED TO SYNCHRONIZE FIRST AND SECOND SIGNALS BY USING TIME-DELAYED VALUES OR RECONSTRUCTED VALUES OCCURRING COINCIDENT WITH A TRANSITION OF A DIGITAL TIME REFERENCE SIGNAL

CROSS-REFERENCE TO RELATED APPLICATIONS

This is a divisional of U.S. Nonprovisional patent application Ser. No. 16/450,377, entitled "Measurement And Testing System", filed on Jun. 24, 2019, which is a continuation-in-part of U.S. Nonprovisional patent application Ser. No. 15/822,135, entitled "Measurement And Testing System", filed on Nov. 25, 2017, now U.S. Pat. No. 10,331,324; which is a continuation-in-part of U.S. Nonprovisional patent application Ser. No. 14/953,505, entitled "Force Measurement System", filed on Nov. 30, 2015, now U.S. Pat. No. 9,829,311; which is a continuation-in-part of U.S. Nonprovisional patent application Ser. No. 14/556,656, entitled "Measurement And Testing System", filed on Dec. 1, 2014, now U.S. Pat. No. 9,200,897; which is a continuation-in-part of U.S. Nonprovisional patent application Ser. No. 14/042,332, entitled "Measurement And Testing System", filed on Sep. 30, 2013, now U.S. Pat. No. 8,902,249; which is a continuation-in-part of U.S. Nonprovisional patent application Ser. No. 13/726,065, entitled "Measurement And Testing System", filed on Dec. 22, 2012, now U.S. Pat. No. 8,643,669; the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a measurement and testing system. More particularly, the invention relates to a measurement and testing system that may be in the form of a force measurement system.

2. Background

Measurement and testing systems are utilized in various fields to detect and analyze many different measurable quantities. For example, in biomedical applications, measurement and testing systems are used for gait analysis, assessing balance and mobility, evaluating sports performance, and assessing ergonomics. However, conventional measurement and testing systems have numerous limitations and drawbacks.

In order to properly execute certain tests utilizing measurement and testing systems, it is often necessary to utilize a large measurement surface area. However, conventional measurement and testing systems with large measurement surface areas have no means by which to separately analyze the movement of the individual legs of the subject walking thereon. Also, conventional measurement and testing systems with large measurement surface areas are difficult to install, and are not easily adaptable to different space configurations in a building.

Therefore, what is needed is a measurement and testing system with a large measurement surface area that enables the movement of the individual legs of the subject disposed thereon to be separately analyzed. Moreover, what is needed is a measurement and testing system that includes a data acquisition and processing device which is specially programmed to determine the movement generated by each of the legs separately. Furthermore, a need exists for a measurement and testing system in the form of a force measurement system with a modular configuration that is easy to install, and is readily adaptable to different building space configurations. In addition, what is needed is a measurement and testing system that is capable of combining data channels from various devices with different sampling rates into a single time-synced channel collection.

BRIEF SUMMARY OF EMBODIMENTS OF THE INVENTION

Accordingly, the present invention is directed to a measurement and testing system that substantially obviates one or more problems resulting from the limitations and deficiencies of the related art.

In accordance with one or more embodiments of the present invention, there is provided a measurement and testing system comprising a first measurement device having a first sampling rate, the first measurement device configured to sense one or more measured quantities and output one or more first measurement signals that are representative of the one or more measured quantities, the one or more first measurement signals comprising a first plurality of data values with corresponding first timestamps associated with each of the first plurality of data values; a second measurement device having a second sampling rate that is different than the first sampling rate of the first measurement device, the second measurement device configured to sense one or more measured quantities and output one or more second measurement signals that are representative of the one or more measured quantities, the one or more second measurement signals comprising a second plurality of data values with corresponding second timestamps associated with each of the second plurality of data values; and a data processing device operatively coupled to the first measurement device and the second measurement device, the data processing device configured to receive the one or more first measurement signals from the first measurement device and the one or more second measurement signals from the second measurement device, the data processing device further configured to synchronize each of the first plurality of data values with each of the second plurality of data values by determining which of the first timestamps correspond to the second timestamps.

In a further embodiment of the present invention, the second sampling rate of the second measurement device is greater than the first sampling rate of the first measurement device, or the second sampling rate of the second measurement device is less than the first sampling rate of the first measurement device.

In yet a further embodiment, the first measurement device is in the form of a force plate and the second measurement device is in the form of an inertial measurement unit, and wherein the second sampling rate of the inertial measurement unit is variable over time.

In still a further embodiment, the first measurement device is in the form of a force plate and the second measurement device is in the form of a motion capture device.

In yet a further embodiment, the second measurement device has fewer data values than the first measurement device such that the second measurement device has missing data values for a subset of the second timestamps; and the data processing device is further configured to fill-in the missing data values corresponding to the subset of the second timestamps by duplicating a particular one of the second plurality of data values until a next one of the second plurality of data values having a sampled value is reached in the data set.

In still a further embodiment, the second measurement device has fewer data values than the first measurement device such that the second measurement device has missing data values for a subset of the second timestamps; and the data processing device is further configured to fill-in the missing data values corresponding to the subset of the second timestamps by interpolating between known ones of the second plurality of data values.

In yet a further embodiment, the first measurement device has fewer data values than the second measurement device such that the first measurement device has missing data values for a subset of the first timestamps; and the data processing device is further configured to fill-in the missing data values corresponding to the subset of the first timestamps by computing time-delayed values of the one or more first measurement signals from the first measurement device using a predetermined time delay, the time-delayed values occurring between sampled data values of the one or more first measurement signals.

In still a further embodiment, the first measurement device has fewer data values than the second measurement device such that the first measurement device has missing data values for a subset of the first timestamps; and the data processing device is further configured to fill-in the missing data values corresponding to the subset of the first timestamps by computing an interpolated continuous curve between sampled data values of the one or more first measurement signals, and the data processing device is additionally configured to estimate the missing data values for the subset of the first timestamps from the interpolated continuous curve.

In accordance with one or more other embodiments of the present invention, there is provided a measurement and testing system comprising a first measurement device having a first sampling rate, the first measurement device configured to sense one or more measured quantities and output one or more first measurement signals that are representative of the one or more measured quantities; a second measurement device having a second sampling rate that is different than the first sampling rate of the first measurement device, the second measurement device configured to sense one or more measured quantities and output one or more second measurement signals that are representative of the one or more measured quantities, the second measurement device being part of a data collection subsystem; a microcontroller configured to sample a digital time reference signal at a predetermined sampling period; and a data processing device operatively coupled to the first measurement device, the second measurement device, and the microcontroller, the data processing device configured to receive the one or more first measurement signals from the first measurement device and the digital time reference signal from the microcontroller, the data processing device further configured to compute time-delayed values of the one or more first measurement signals from the first measurement device using a predetermined time delay, the data processing device additionally configured to select particular ones of the computed time-delayed values that occur coincident with a predetermined transition of the digital time reference signal produced by the microcontroller, and the data processing device further configured to send the particular ones of the computed time-delayed values to the data collection subsystem with the second measurement device such that the one or more first measurement signals are able to be synchronized with the one or more second measurement signals.

In a further embodiment of the present invention, the digital time reference signal sampled by the microcontroller is in the form of square wave signal.

In yet a further embodiment, the predetermined transition of the digital time reference signal comprises an up transition of the square wave signal, a down transition of the square wave signal, or both an up transition and down transition of the square wave signal.

In still a further embodiment, the predetermined time delay used by the data processing device to compute the time-delayed values is based upon a predetermined fraction of the sampling period of the one or more first measurement signals from the first measurement device.

In still a further embodiment, the predetermined sampling period of the digital time reference signal sampled by the microcontroller is fractionally proportionate to a sampling period of the first measurement device.

In yet a further embodiment, the predetermined transition of the digital time reference signal determined by the data processing device comprises an increase in the digital time reference signal, a decrease in the digital time reference signal, or both an increase in the digital time reference signal and a decrease in the digital time reference signal.

In accordance with yet one or more other embodiments of the present invention, there is provided a measurement and testing system comprising a first measurement device having a first sampling rate, the first measurement device configured to sense one or more measured quantities and output one or more first measurement signals that are representative of the one or more measured quantities; a second measurement device having a second sampling rate that is different than the first sampling rate of the first measurement device, the second measurement device configured to sense one or more measured quantities and output one or more second measurement signals that are representative of the one or more measured quantities, the second measurement device being part of a data collection subsystem; a microcontroller configured to sample a digital time reference signal on each of one or more predetermined transitions and record the time values; and a data processing device operatively coupled to the first measurement device, the second measurement device, and the microcontroller, the data processing device configured to receive the one or more first measurement signals from the first measurement device and the digital time reference signal from the microcontroller, the data processing device further configured to compute, for each of the time values determined by the microcontroller, a reconstructed value of the one or more first measurement signals outputted by the first measurement device, and the data processing device additionally configured to send the computed reconstructed values to the data collection subsystem with the second measurement device for each predetermined transition of the digital time reference signal such that the one or more first measurement signals are able to be synchronized with the one or more second measurement signals.

In a further embodiment of the present invention, the digital time reference signal sampled by the microcontroller is in the form of square wave signal.

In yet a further embodiment, the predetermined transition of the digital time reference signal comprises an up transition of the square wave signal, a down transition of the square wave signal, or both an up transition and down transition of the square wave signal.

In still a further embodiment, the reconstructed values computed by the data processing device comprise sinc reconstructed values.

In yet a further embodiment, the predetermined transition of the digital time reference signal determined by the data processing device comprises an increase in the digital time reference signal, a decrease in the digital time reference signal, or both an increase in the digital time reference signal and a decrease in the digital time reference signal.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 14 depicts an exemplary portion of software program code and exemplary tabular data for illustrating the manner in which session records are sorted during the timeline bar generation procedure;

FIG. 22 is a partial screenshot displayed on the operator visual display device of the measurement and testing system illustrating a second plurality of global/progress reports that a system user is able to select, according to an embodiment of the invention;

Throughout the figures, the same parts are always denoted using the same reference characters so that, as a general rule, they will only be described once.

DETAILED DESCRIPTION OF EMBODIMENTS OF THE INVENTION

The present invention is described herein, in an exemplary manner, with reference to hardware components, computer system architecture, and flowcharts that illustrate exemplary processes carried out by the computer system. In a preferred embodiment, functional blocks of the flowchart illustrations can be implemented by computer system instructions. These computer program instructions may be loaded directly onto an internal data storage device of a computing device (e.g., a hard drive of a computer). Alternatively, these computer program instructions could be stored on a portable computer-readable medium (e.g., a flash drive, a floppy disk, a compact disk, etc.), and then subsequently loaded onto a computing device such that the instructions can be executed thereby. In other embodiments, these computer program instructions could be embodied in the hardware of the computing device, rather than in the software thereof. It is also possible for the computer program instructions to be embodied in a combination of both the hardware and the software. Also, in the disclosure, when a reference is made to a computing device that is "configured to", "arranged to" and/or "configured and arranged to" perform a specific function (e.g., a data acquisition/data processing device 104 configured and arranged to perform a specific function), it is to be understood that, in one or more embodiments of the invention, this means that the computing device is specially programmed to carry out the particular function (e.g., the data acquisition/data processing device 104 being specially programmed to perform a specific function).

This description describes in general form the computer program(s) required to carry out the various features of the invention. Any competent programmer in the field of information technology could develop a functioning system using the description set forth herein.

For the sake of brevity, conventional computer system components, conventional data networking, and conventional software coding will not be described in detail herein. Also, it is to be understood that the connecting lines shown in the block diagram(s) included herein are intended to represent functional relationships and/or operational couplings between the various components. Similarly, connecting lines are also used between the elements of the flowcharts in order to illustrate the functional relationships therebetween. In addition to that which is explicitly depicted, it is to be understood that many alternative or additional functional relationships and/or physical connections may be incorporated in a practical application of the system.

Figure 1:
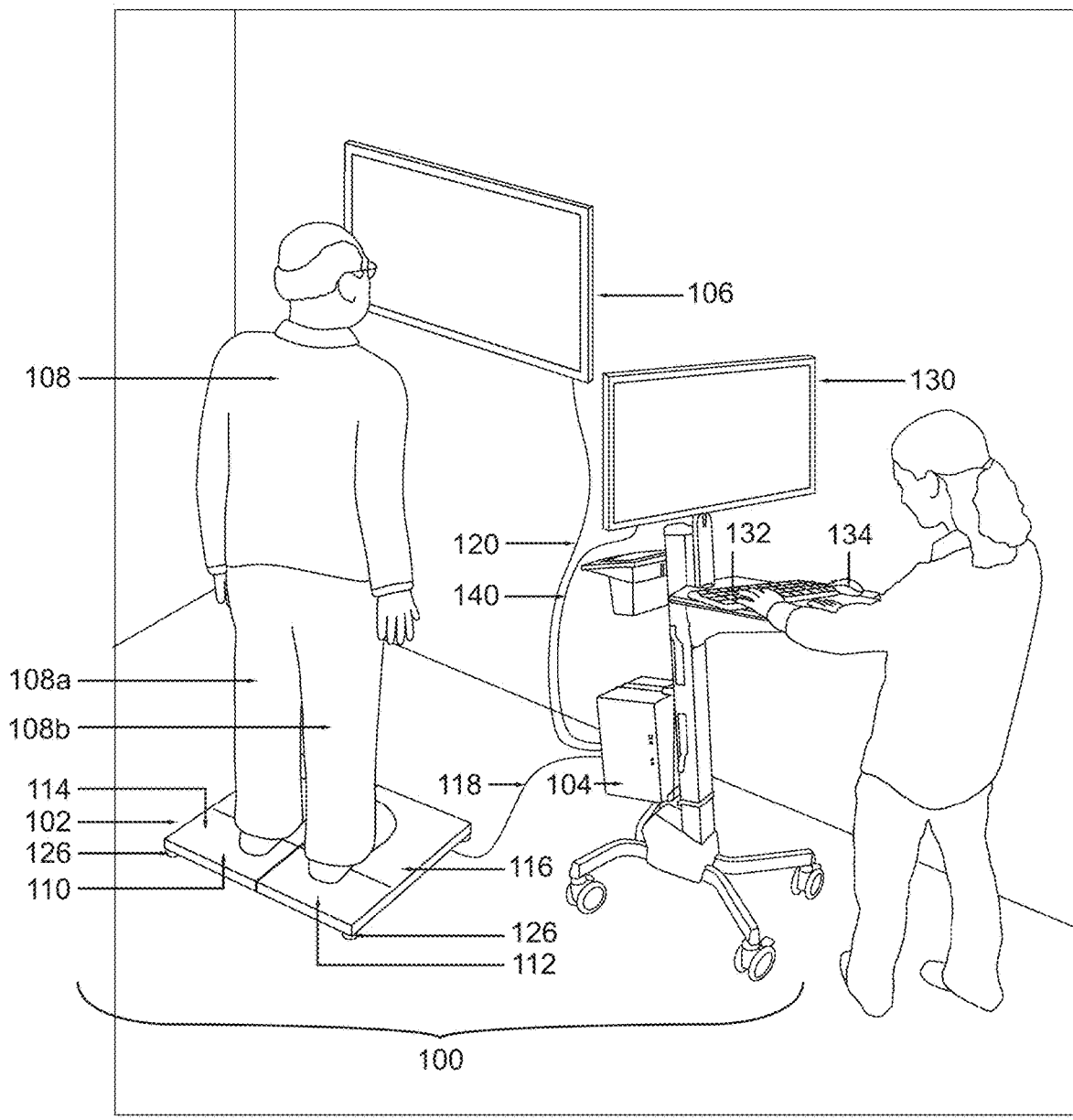
FIG. 1 is a diagrammatic perspective view of a measurement and testing system according to an embodiment of the invention.

An exemplary embodiment of the measurement and testing system is seen generally at 100 in FIG. 1. In the illustrative embodiment, the measurement and testing system 100 generally comprises a measurement assembly 102 (e.g., a force measurement assembly) that is operatively coupled to a data acquisition/data processing device 104 (i.e., a data acquisition and processing device or computing device that is capable of collecting, storing, and processing data), which in turn, is operatively coupled to a subject visual display device 106 and an operator visual display device 130. As illustrated in FIG. 1, the force measurement assembly 102 is configured to receive a subject 108 thereon, and is capable of measuring the forces and/or moments applied to its measurement surfaces 114, 116 by the subject 108.

As shown in FIG. 1, the data acquisition/data processing device 104 includes a plurality of user input devices 132, 134 connected thereto. Preferably, the user input devices 132, 134 comprise a keyboard 132 and a mouse 134. In addition, the operator visual display device 130 may also serve as a user input device if it is provided with touch screen capabilities. While a desktop type computing system is depicted in FIG. 1, one of ordinary of skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the claimed invention.

As illustrated in FIG. 1, force measurement assembly 102 is operatively coupled to the data acquisition/data processing device 104 by virtue of an electrical cable 118. In one embodiment of the invention, the electrical cable 118 is used for data transmission, as well as for providing power to the force measurement assembly 102. Various types of data transmission cables can be used for cable 118. For example, the cable 118 can be a Universal Serial Bus (USB) cable or an Ethernet cable. Preferably, the electrical cable 118 contains a plurality of electrical wires bundled together, with at least one wire being used for power and at least another wire being used for transmitting data. The bundling of the power and data transmission wires into a single electrical cable 118 advantageously creates a simpler and more efficient design. In addition, it enhances the safety of the testing environment when human subjects are being tested on the force measurement assembly 102. However, it is to be understood that the force measurement assembly 102 can be operatively coupled to the data acquisition/data processing device 104 using other signal transmission means, such as a wireless data transmission system. If a wireless data transmission system is employed, it is preferable to provide the force measurement assembly 102 with a separate power supply in the form of an internal power supply or a dedicated external power supply.

Referring again to FIG. 1, it can be seen that the force measurement assembly 102 of the illustrated embodiment is in the form of a dual force plate assembly. The dual force plate assembly includes a first plate component 110, a second plate component 112, at least one measurement device (e.g., force transducer) associated with the first plate component 110, and at least one measurement device (e.g., force transducer) associated with the second plate component 112. In the illustrated embodiment, a subject 108 stands in an upright position on the force measurement assembly 102 and each foot of the subject 108 is placed on the top surfaces 114, 116 of a respective plate component 110, 112 (i.e., one foot on the top surface 114 of the first plate component 110 and the other foot on the top surface 116 of the second plate component 112). The at least one force transducer associated with the first plate component 110 is configured to sense one or more measured quantities and output one or more first signals that are representative of forces and/or moments being applied to its measurement surface 114 by the left foot/leg 108a of the subject 108, whereas the at least one force transducer associated with the second plate component 112 is configured to sense one or more measured quantities and output one or more second signals that are representative of forces and/or moments being applied to its measurement surface 116 by the right foot/leg 108b of subject 108.

Figure 4:
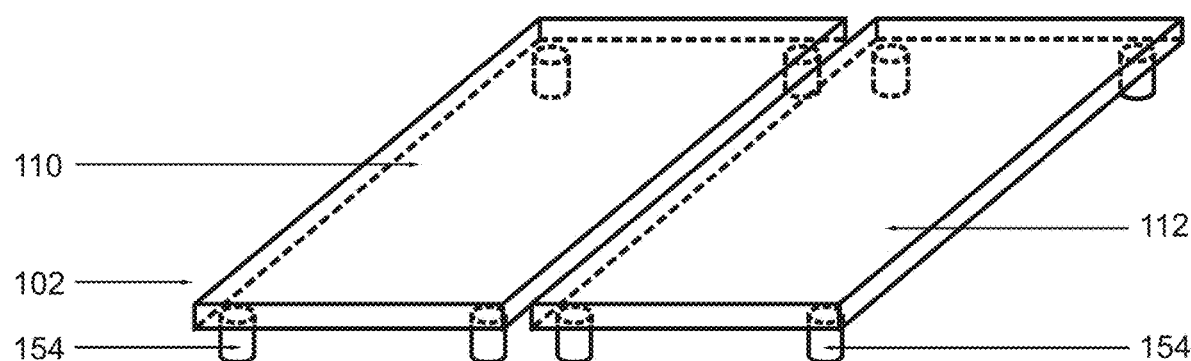
FIG. 4 is a diagrammatic perspective view of one measurement assembly used in the measurement and testing system, according to an embodiment of the invention, wherein the measurement assembly is in the form of a dual force plate.

In illustrated embodiment, the at least one force transducer associated with the first and second plate components 110, 112 comprises four (4) pylon-type force transducers 154 (or pylon-type load cells) that are disposed underneath, and near each of the four corners (4) of the first plate component 110 and the second plate component 112 (see FIG. 4). Each of the eight (8) illustrated pylon-type force transducers has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 102.

In an alternative embodiment, rather than using four (4) pylon-type force transducers 154 on each plate component 110, 112, force transducers in the form of transducer beams could be provided under each plate component 110, 112. In this alternative embodiment, the first plate component 110 could comprise two transducer beams that are disposed underneath, and on generally opposite sides of the first plate component 110. Similarly, in this embodiment, the second plate component 112 could comprise two transducer beams that are disposed underneath, and on generally opposite sides of the second plate component 112. Similar to the pylon-type force transducers 154, the force transducer beams could have a plurality of strain gages attached to one or more surfaces thereof for sensing the mechanical strain imparted on the beam by the force(s) applied to the surfaces of the force measurement assembly 102.

Rather, than using four (4) force transducer pylons under each plate, or two spaced apart force transducer beams under each plate, it is to be understood that the force measurement assembly 102 can also utilize the force transducer technology described in commonly-owned U.S. Pat. No. 8,544,347, the entire disclosure of which is incorporated herein by reference.

Figure 6:
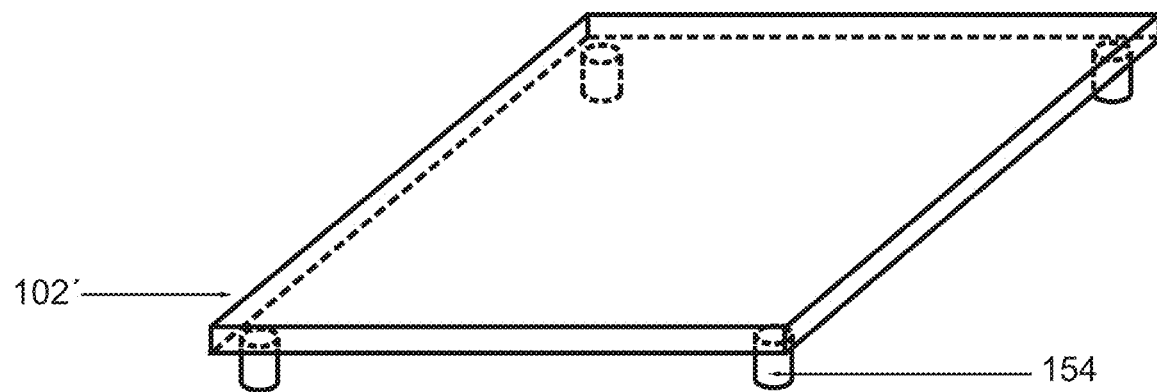
FIG. 6 is a diagrammatic perspective view of another measurement assembly used in the measurement and testing system, according to an embodiment of the invention, wherein the measurement assembly is in the form of a single force plate.

In other embodiments of the invention, rather than using a measurement assembly 102 having first and second plate components 110, 112, it is to be understood that a force measurement assembly 102' in the form of a single force plate may be employed (see FIG. 6). Unlike the dual force plate assembly illustrated in FIGS. 1 and 4, the single force plate comprises a single measurement surface on which both of a subject's feet are placed during testing. Although, similar to the measurement assembly 102, the illustrated single force plate 102' comprises four (4) pylon-type force transducers 154 (or pylon-type load cells) that are disposed underneath, and near each of the four corners (4) thereof for sensing the load applied to the surface of the force measurement assembly 102'.

Also, as shown in FIG. 1, the force measurement assembly 102 is provided with a plurality of support feet 126 disposed thereunder. Preferably, each of the four (4) corners of the force measurement assembly 102 is provided with a support foot 126 (e.g., mounted on the bottom of each pylon-type force transducer or on the bottom of a base). In one embodiment, each support foot 126 is attached to a bottom surface of a force transducer. In another embodiment, one or more of the force transducers could function as support feet (e.g., if pylon-type force transducers are used, the first and second plate components 110, 112 could be supported on the force transducers). In one preferred embodiment, at least one of the support feet 126 is adjustable so as to facilitate the leveling of the force measurement assembly 102 on an uneven floor surface.

Figure 2:
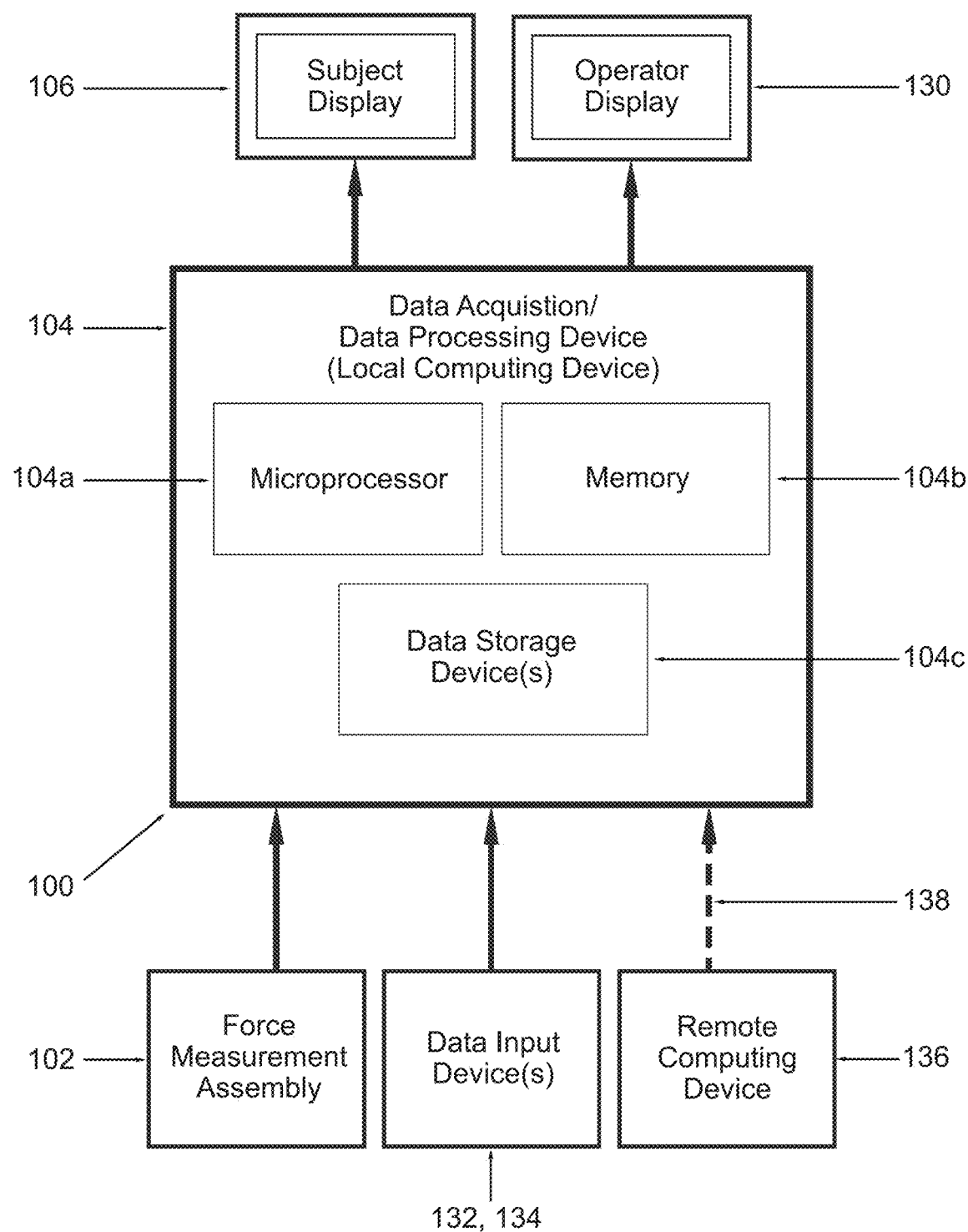
FIG. 2 is a block diagram of constituent components of the measurement and testing system, according to an embodiment of the invention.

Now, turning to FIG. 2, it can be seen that the data acquisition/data processing device 104 (i.e., the local computing device) of the measurement and testing system 100 comprises a microprocessor 104a for processing data, memory 104b (e.g., random access memory or RAM) for storing data during the processing thereof, and data storage device(s) 104c, such as one or more hard drives, compact disk drives, floppy disk drives, flash drives, or any combination thereof. As shown in FIG. 2, the force measurement assembly 102, the subject visual display device 106, and the operator visual display device 130 are operatively coupled to the data acquisition/data processing device 104 such that data is capable of being transferred between these devices 102, 104, 106, and 130. Also, as illustrated in FIG. 2, a plurality of data input devices 132, 134 such as the keyboard 132 and mouse 134 shown in FIG. 1, are operatively coupled to the data acquisition/data processing device 104 so that a user is able to enter data into the data acquisition/data processing device 104. In some embodiments, the data acquisition/data processing device 104 can be in the form of a desktop computer, while in other embodiments, the data acquisition/data processing device 104 can be embodied as a laptop computer.

Referring again to FIG. 2, it can be seen that the measurement and testing system 100 can also include a remote computing device 136. Like the data acquisition/data processing device 104 (i.e., the local computing device) described above, the remote computing device 136 also comprises a microprocessor for processing data, memory (e.g., random access memory or RAM) for storing data during the processing thereof, and data storage device(s), such as one or more hard drives, compact disk drives, floppy disk drives, flash drives, or any combination thereof. As shown in FIG. 2, in the illustrated embodiment, the remote computing device 136 can be operatively coupled to the data acquisition/data processing device 104 (i.e., the local computing device) by means of a network connection 138. In some embodiments, the network connection 138 is an encrypted network connection so that data can be securely transferred between the local computing device 104 and the remote computing device 136. The network connection 138 between the computing devices 104, 136 can be a conventional hard-wired connection (e.g., utilizing an Ethernet cable or any other type of suitable data transmission cable), or alternatively, can utilize wireless data transmission technology (e.g., a wireless local area network, commonly referred to as Wi-Fi technology). Alternatively, the network connection 138 between the computing devices 104, 136 can be an Internet-based connection.

In the illustrated embodiment of the invention, the local computing device 104 is disposed at a first location, while the remote computing device 136 is disposed at a second location. Also, in one or more embodiments, the first location is geographically remote from the second location, and the first and second locations are separated from one another by a predetermined distance (e.g., by at least one mile).

With reference again to FIG. 1, the visual display devices 106, 130 of the measurement and testing system 100 will be described in more detail. In the illustrated embodiment, each visual display device 106, 130 is in the form of a flat panel monitor. Those of ordinary skill in the art will readily appreciate that various types of flat panel monitors having various types of data transmission cables 120, 140 may be used to operatively couple the visual display devices 106, 130 to the data acquisition/data processing device 104. For example, the flat panel monitors employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the visual display devices 106, 130 can be operatively coupled to the data acquisition/data processing device 104 using wireless data transmission means. Electrical power is supplied to the visual display devices 106, 130 using a separate power cord that connects to a building wall receptacle.

Those of ordinary skill in the art will appreciate that the visual display devices 106, 130 can be embodied in various forms. For example, if the visual display devices 106, 130 are in the form of flat screen monitors as illustrated in FIG. 1, they may comprise a liquid crystal display (i.e., an LCD display), a light-emitting diode display (i.e., an LED display), a plasma display, a projection-type display, or a rear projection-type display. Although, it will be appreciated that the subject visual display device 106 may take other forms as well, such as a head-mounted display, a heads-up display, or a 3-dimensional display. Each of the visual display devices 106, 130 may also be in the form of a touch pad display. For example, the visual display devices 106, 130 may comprise multi-touch technology which recognizes two or more contact points simultaneously on the surface of the screen so as to enable users of the device to use two fingers for zooming in/out, rotation, and a two finger tap.

Figure 3:
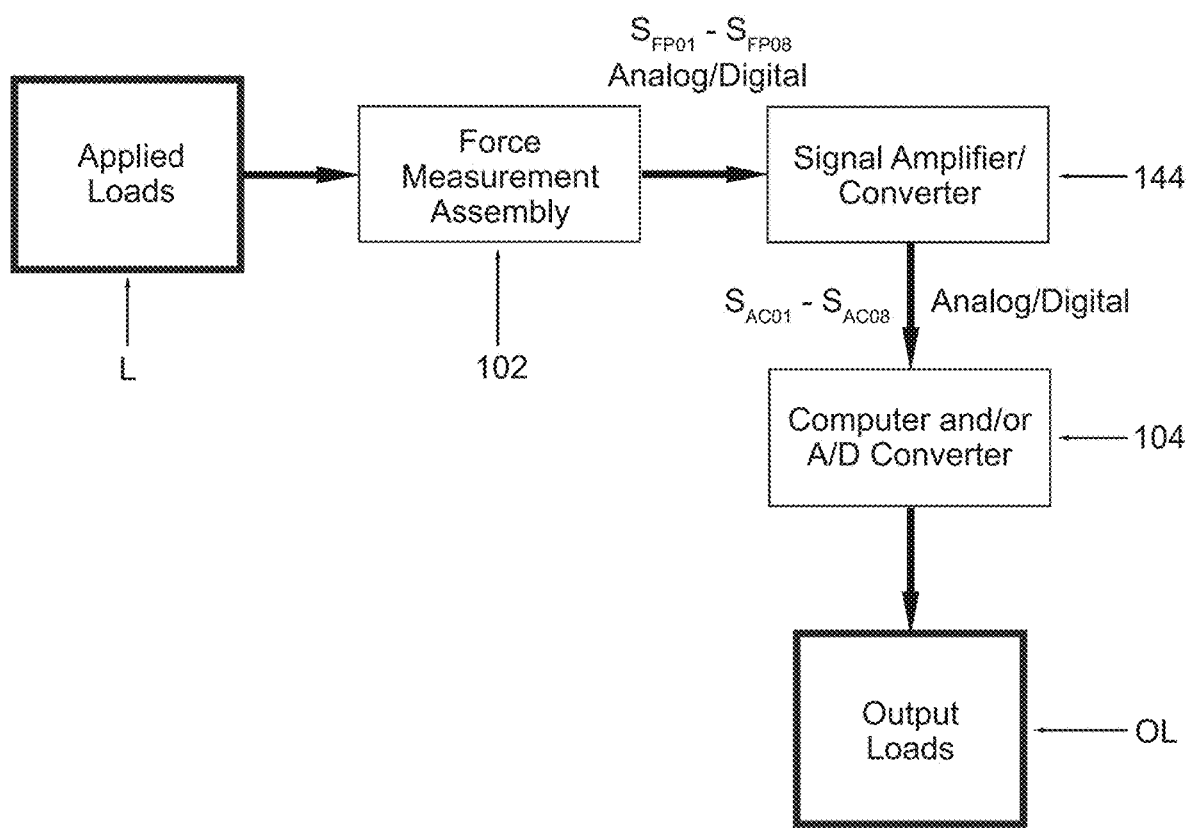
FIG. 3 is a block diagram illustrating data manipulation operations carried out by the measurement and testing system, according to an embodiment of the invention.

FIG. 3 graphically illustrates the acquisition and processing of the load data carried out by the exemplary measurement and testing system 100. Initially, as shown in FIG. 3, a load L is applied to the force measurement assembly 102 by a subject disposed thereon. The load is transmitted from the first and second plate components 110, 112 to its respective set of pylon-type force transducers or force transducer beams. As described above, in one embodiment of the invention, each plate component 110, 112 comprises four (4) pylon-type force transducers 154 disposed thereunder. Preferably, these pylon-type force transducers are disposed near respective corners of each plate component 110, 112. In a preferred embodiment of the invention, each of the pylon-type force transducers includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the first and second plate components 110, 112. For each plurality of strain gages disposed on the pylon-type force transducers, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 154 disposed under each plate component 110, 112 output a total of four (4) analog output voltages (signals). In some embodiments, the four (4) analog output voltages from each plate component 110, 112 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 102 transmits the force plate output signals $S_{FPO1}$-$S_{FPO8}$ to a main signal amplifier/converter 144. Depending on whether the preamplifier board also includes an analog-to-digital (A/D) converter, the force plate output signals $S_{FPO1}$-$S_{FPO8}$ could be either in the form of analog signals or digital signals. The main signal amplifier/converter 144 further magnifies the force plate output signals $S_{FPO1}$-$S_{FPO8}$, and if the signals $S_{FPO1}$-$S_{FPO8}$ are of the analog-type (for a case where the preamplifier board did not include an analog-to-digital (A/D) converter), it may also convert the analog signals to digital signals. Then, the signal amplifier/converter 144 transmits either the digital or analog signals $S_{ACO1}$-$S_{ACO8}$ to the data acquisition/data processing device 104 (computer 104) so that the forces and/or moments that are being applied to the surfaces of the force measurement assembly 102 can be transformed into output load values OL. In addition to the components 104a, 104b, 104c, the data acquisition/data processing device 104 may further comprise an analog-to-digital (A/D) converter if the signals $S_{ACO1}$-$S_{ACO8}$ are in the form of analog signals. In such a case, the analog-to-digital converter will convert the analog signals into digital signals for processing by the microprocessor 104a.

Figure 5:
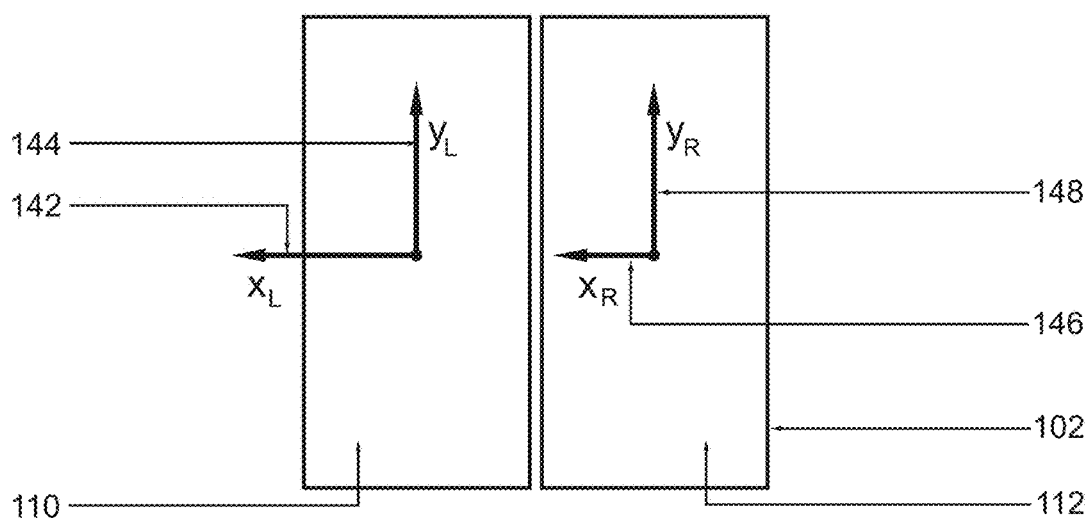
FIG. 5 is a diagrammatic top view of one measurement assembly used in the measurement and testing system with exemplary coordinate axes superimposed thereon, according to an embodiment of the invention, wherein the measurement assembly is in the form of a dual force plate.

When the data acquisition/data processing device 104 receives the voltage signals $S_{ACO1}$-$S_{ACO8}$, it initially transforms the signals into output forces and/or moments by multiplying the voltage signals $S_{ACO1}$-$S_{ACO8}$ by a calibration matrix. After which, the force $F_L$ exerted on the surface of the first force plate by the left foot of the subject, the force $F_R$ exerted on the surface of the second force plate by the right foot of the subject, and the center of pressure for each foot of the subject (i.e., the x and y coordinates of the point of application of the force applied to the measurement surface by each foot) are determined by the data acquisition/data processing device 104. Referring to FIG. 5, which depicts a top view of the measurement assembly 102, it can be seen that the center of pressure coordinates ($x_{P_L}$, $y_{P_L}$) for the first plate component 110 are determined in accordance with x and y coordinate axes 142, 144. Similarly, the center of pressure coordinates ($x_{P_R}$, $y_{P_R}$) for the second plate component 112 are determined in accordance with x and y coordinate axes 146, 148. If the force transducer technology described in pending, commonly-owned U.S. patent application Ser. No. 13/348,506 is employed, it is to be understood that the center of pressure coordinates ($x_{P_L}$, $y_{P_L}$, $x_{P_R}$, $x_{P_R}$) can be computed in the particular manner described in that application.

Figure 7:
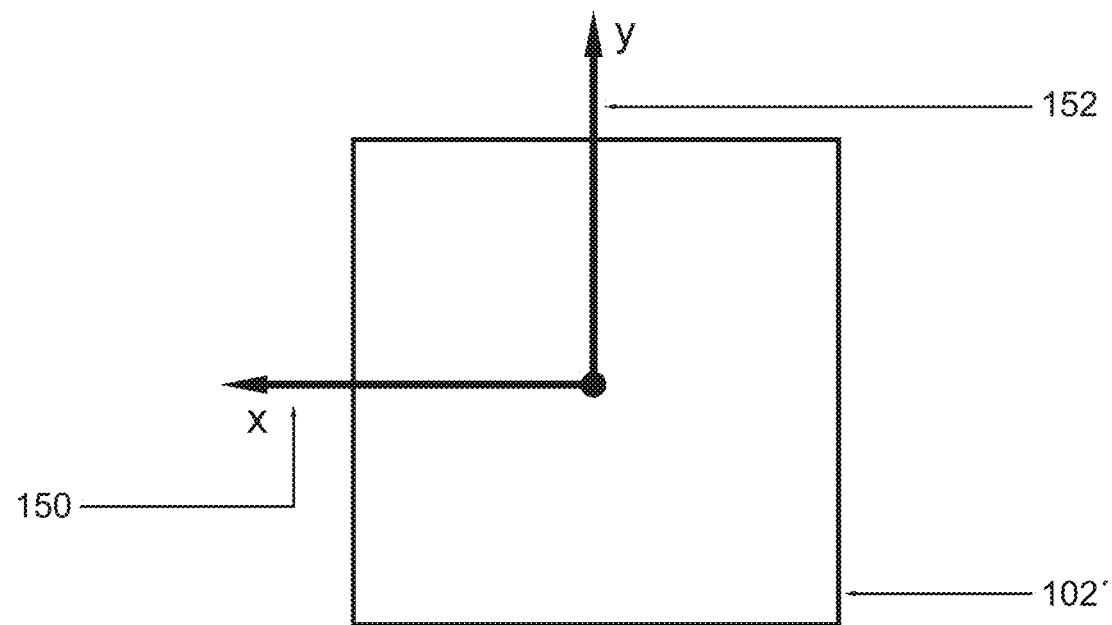
FIG. 7 is a diagrammatic top view of another measurement assembly used in the measurement and testing system with exemplary coordinate axes superimposed thereon, according to an embodiment of the invention, wherein the measurement assembly is in the form of a single force plate.

As explained above, rather than using a measurement assembly 102 having first and second plate components 110, 112, a force measurement assembly 102' in the form of a single force plate may be employed (see FIGS. 6 and 7, which illustrate a single force plate). As discussed hereinbefore, the single force plate comprises a single measurement surface on which both of a subject's feet are placed during testing. As such, rather than computing two sets of center of pressure coordinates (i.e., one for each foot of the subject), the embodiments employing the single force plate compute a single set of overall center of pressure coordinates ($x_P$, $y_P$) in accordance with x and y coordinate axes 150, 152.

In one exemplary embodiment, the data acquisition/data processing device 104 determines the vertical forces $F_{Lz}$, $F_{Rz}$ exerted on the surface of the first and second force plates by the feet of the subject and the center of pressure for each foot of the subject, while in another exemplary embodiment, the output forces of the data acquisition/data processing device 104 include all three (3) orthogonal components of the resultant forces acting on the two plate components 110, 112 (i.e., $F_{Lx}$, $F_{Ly}$, $F_{Lz}$, $F_{Rx}$, $F_{Ry}$, $F_{Rz}$). In yet other embodiments of the invention, the output forces and moments of the data acquisition/data processing device 104 can be in the form of other forces and moments as well.

Now, specific functionality of the exemplary measurement and testing system 100 will be described in detail. It is to be understood that the aforedescribed functionality of the measurement and testing system 100 can be carried out by the data acquisition/data processing device 104 (i.e., the local computing device) utilizing software, hardware, or a combination of both hardware and software. For example, the data acquisition/data processing device 104 can be specially programmed to carry out the functionality described hereinafter. In one embodiment of the invention, the computer program instructions necessary to carry out this functionality may be loaded directly onto an internal data storage device 104c of the data acquisition/data processing device 104 (e.g., on a hard drive thereof) and subsequently executed by the microprocessor 104a of the data acquisition/data processing device 104. Alternatively, these computer program instructions could be stored on a portable computer-readable medium (e.g., a flash drive, a floppy disk, a compact disk, etc.), and then subsequently loaded onto the data acquisition/data processing device 104 such that the instructions can be executed thereby. In one embodiment, these computer program instructions are embodied in the form of a measurement and testing software program executed by the data acquisition/data processing device 104. In other embodiments, these computer program instructions could be embodied in the hardware of the data acquisition/data processing device 104, rather than in the software thereof. It is also possible for the computer program instructions to be embodied in a combination of both the hardware and the software.

Figure 8:
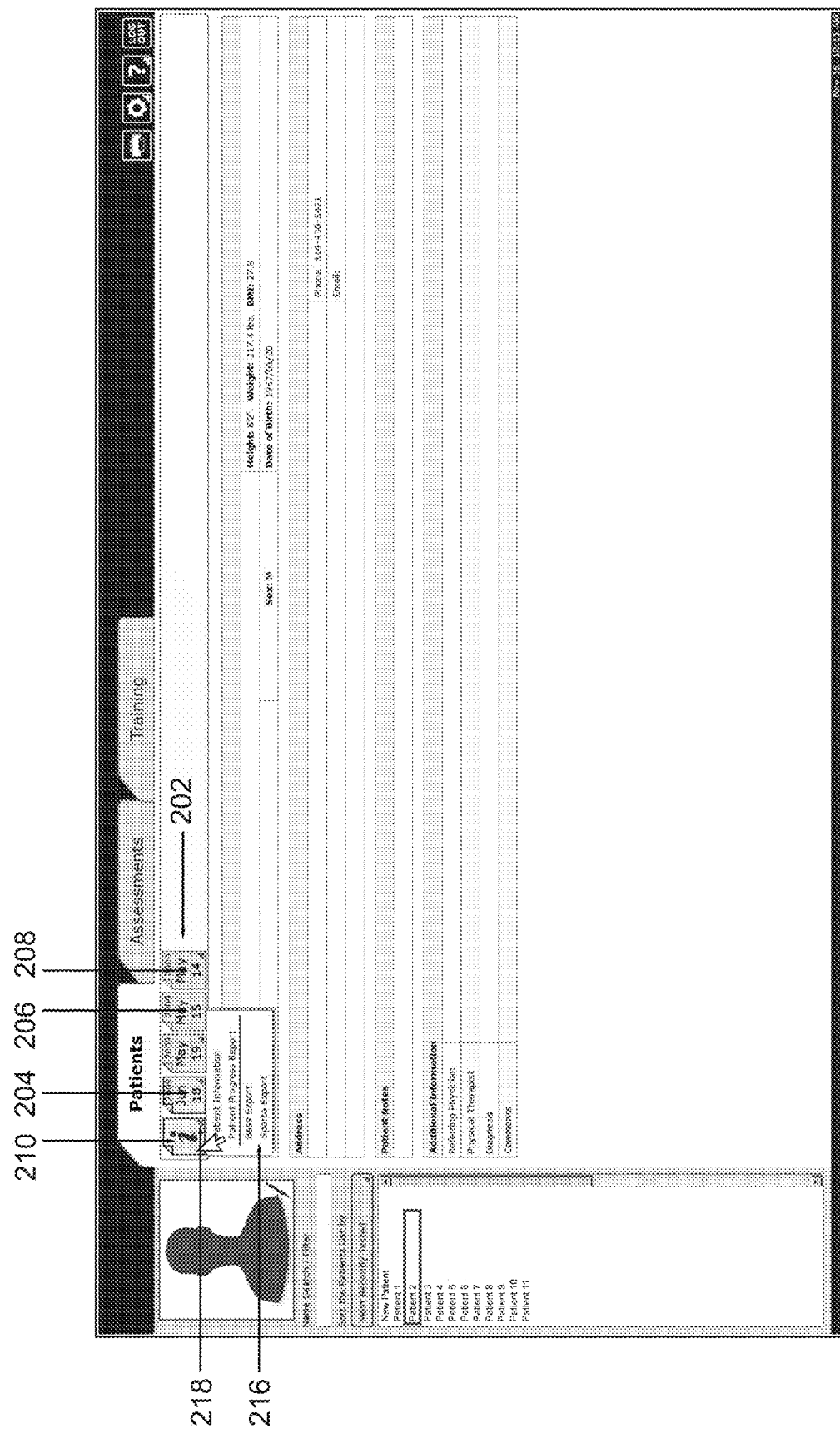
FIG. 8 is a first screenshot displayed on the operator visual display device of the measurement and testing system illustrating the timeline bar feature, according to an embodiment of the invention.
Figure 9:
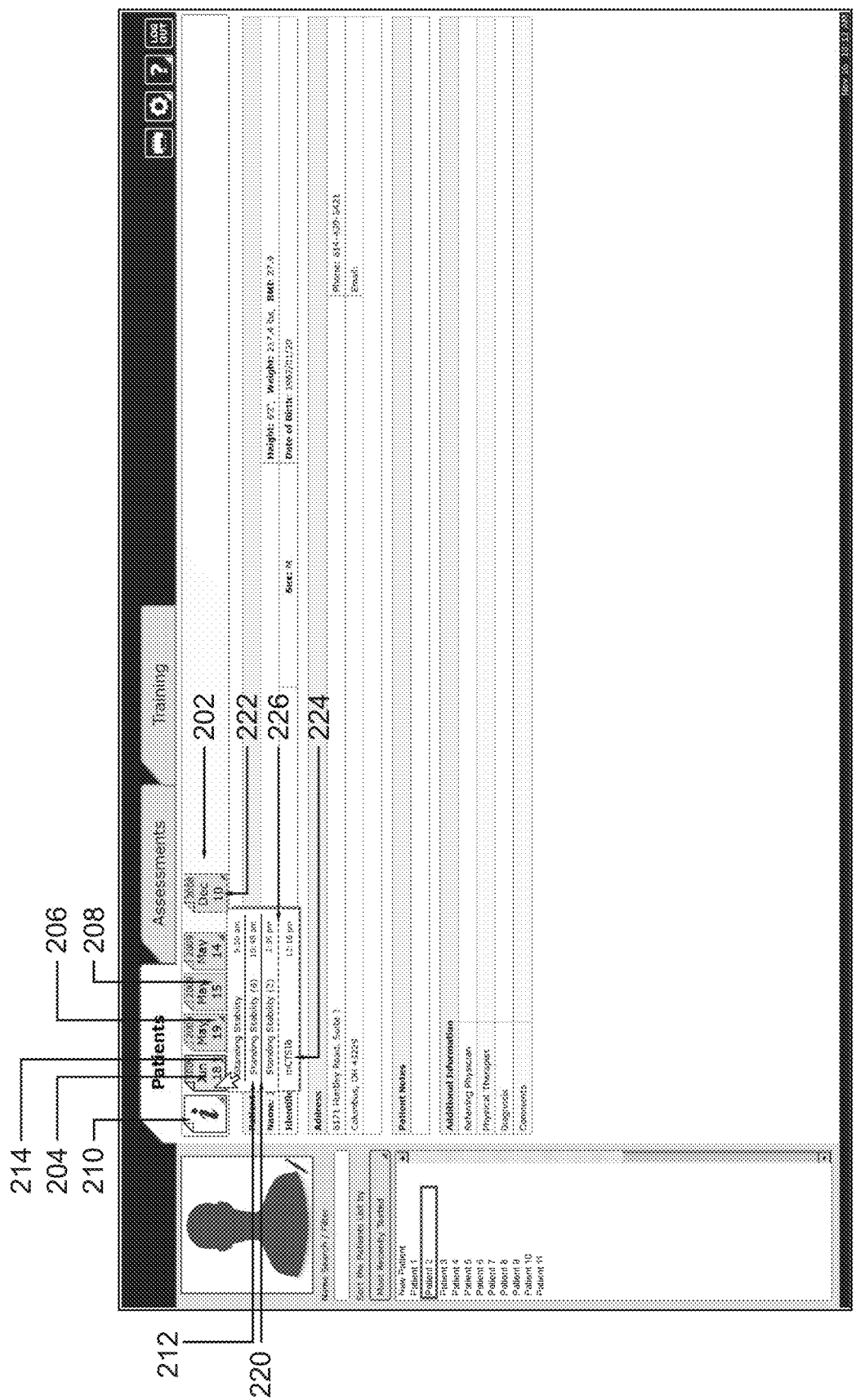
FIG. 9 is a second screenshot displayed on the operator visual display device of the measurement and testing system illustrating the timeline bar feature, according to an embodiment of the invention.

According to one aspect of the illustrative embodiment, referring to FIGS. 8 and 9, the data acquisition/data processing device 104 of the measurement and testing system 100 is configured and arranged to generate a screen image 200 that includes a timeline bar 202 disposed proximate to a top of the output screen of the operator visual display device 130. As shown in FIGS. 8 and 9, the illustrated timeline bar 202 includes a plurality date icons 204, 206, 208 for accessing subject testing output data. The data acquisition/data processing device 104 is additionally configured to assign the subject testing output data to a selected one of the plurality of date icons 204, 206, 208 in accordance with the date on which the subject testing output data was generated. In addition, as illustrated in FIGS. 8 and 9, the data acquisition/processing device 104 is further configured to generate a subject (patient) information icon 210 in the timeline bar 202 that includes information about a particular test subject for which output data was generated by the measurement and testing system 100. In FIG. 9, it can also be seen that the data acquisition/processing device 104 is further configured to generate a drop-down menu 212 for at least one of the plurality of date icons (e.g., date icon 204), wherein the drop-down menu 212 comprises output data collected at a plurality of different times on the date (e.g., Jun. 18, 2009) displayed on the associated date icon 204. As shown in FIG. 9, the data acquisition/processing device 104 is preferably configured to arrange the output data listed in the drop-down menu 212 in accordance with the time at which the output data was collected. In particular, the output data collected at the plurality of different times is arranged by the data acquisition/processing device 104 in one of ascending or descending order based upon the time at which it was collected (FIG. 9 illustrates an example of arrangement in ascending order, i.e., listing morning (AM) times before afternoon (PM) times). Also, referring to FIG. 9, it can be seen that the data acquisition/processing device 104 is configured to generate a visual indicator 214 (e.g., a small triangle) in a lower corner of the date icon 204 containing the drop-down menu 212. Similarly, the other date icons 206, 208, which also contain drop down menus, are provided with visual indicators (e.g., small triangles) in the lower corners thereof.

Referring to FIG. 8, it can be seen that, similar to the plurality of date icons 204, 206, 208, the subject (patient) information icon 210 also contains a drop-down menu 216. The patient or subject drop-down menu 216 includes several different items that may be selected by the user of the system 100, such as general patent information, patient progress reports, and data exporting options. Also, like one or more of the plurality of date icons 204, 206, 208, the subject (patient) information icon 210 has a visual indicator 218 (e.g., a small triangle) in a lower corner thereof in order to inform users of the system 100 that the subject (patient) information icon 210 contains a drop-down menu 216.

Now, the specific attributes of the timeline bar 202, which can be embodied in a measurement and testing software program(s), will be described in more detail. As illustrated in FIGS. 8 and 9, the items (e.g., subject testing results) in the timeline bar 202 are organized by date, and additionally sorted by time. The measurement and testing software program executed by the data acquisition/data processing device 104 also groups tests performed during a particular session together. In one embodiment of the invention, a session is defined as a series of tests that are performed in succession without exiting the test series. As such, test results, which are a form of output data generated from the measurement device signals of the measurement assembly 102, are grouped into session records (i.e. session records can comprise a collection of output data from the measurement assembly 102, as well as other types of data). Although, a session could be defined in a different manner in other embodiments of the invention. For example, in other embodiments, a session could be determined in accordance with predetermined window of time (e.g., 10 minutes) as set by a user, or a session could be defined as a specific block of tests that are specified by the user to comprise a session. In the drop-down menu 212 (see FIG. 9), it can be seen that eight Standing Stability tests (the quantity of tests is indicated by the parenthetical number) are separated from two Standing Stability tests by a separating line 220. The eight Standing Stability tests were performed during the same session, while the two Standing Stability tests were performed during a different, subsequent session. The separating line 220 separates the two distinct sessions from one another.

The dynamic population feature of the measurement and testing software program, as will be described hereinafter, drives the content of the timeline bar 202. For example, suppose three Standing Stability tests are performed in the same session. The measurement and testing software will combine these into a single report when the testing data is entered into the program.

Figure 10:
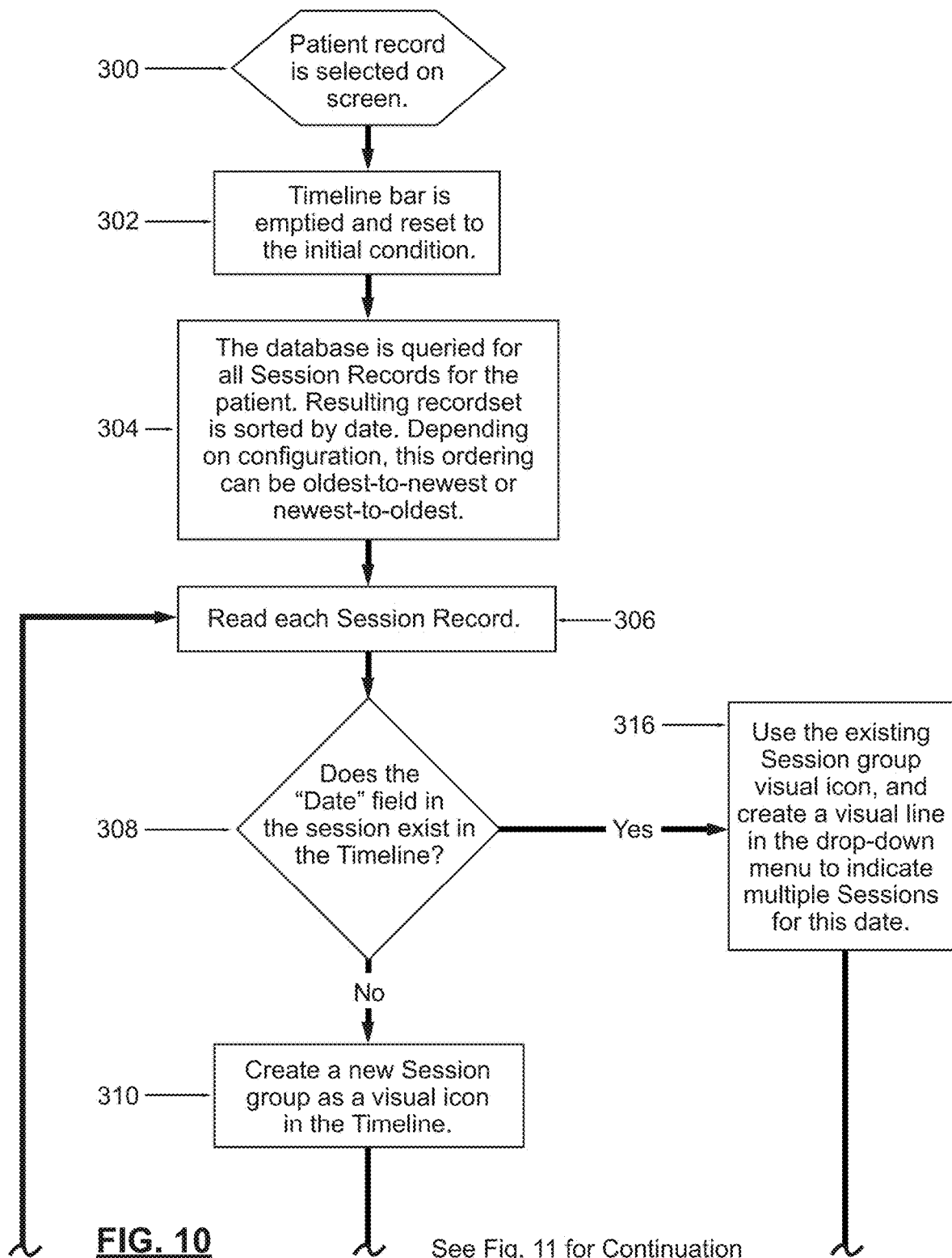
FIG. 10 is a partial flowchart illustrating a manner in which the timeline bar is generated by the measurement and testing system, according to an embodiment of the invention.

In accordance with this aspect of the illustrative embodiment, a flowchart illustrating the functionality of the timeline bar feature of the measurement and testing system 100 is set forth in FIGS. 10-13. All of the steps described below with reference to the flowcharts of FIGS. 10-13 are carried out by the data acquisition/processing device 104. In particular, the flowcharts graphically illustrate the manner in which the data acquisition/processing device 104 generates the timeline bar, as well as the manner in which output data is assigned to elements of the timeline bar. Referring initially to FIG. 10, the procedure commences at 300 when a patient record is selected on the screen by a system user, and in step 302, the timeline bar 202 is emptied and reset to the initial condition by the data acquisition/processing device 104 in response to the user input (i.e., the contents of the timeline bar 202 are deleted). After the timeline bar 202 is emptied and reset, a database (e.g., a patient database) is queried for all session records pertaining to a particular patient (step 304). For example, the patient database can be searched for all records containing the same patient globally unique identifier (GUID), which identifies a particular patient. Then, once all records having the same patient GUID are isolated, the resulting record set is sorted by date (see e.g., table 340 in FIG. 14). Depending on the particular configuration that is desired, this sorting order can be oldest-to-newest or newest-to-oldest.

As an example of the operations performed in step 304, reference is made to the exemplary query string 338 in FIG. 14. The "SELECT" statement in this query string 338 creates a resulting data set from the combination of two tables: (i) a first table, entitled "Sessions", which contains, for example, reference identifiers to the test results; and (ii) a second table, entitled "TestResults", which includes, for example, the weight of the subject, the height of the subject, and computed values for a particular test (TestResults.SessionGUID=Sessions.GUID). The "WHERE" clause in the query string 338 only returns results for a matching patient identifier (i.e., patent GUID "4f6 . . . a5d"—the middle characters of the GUID have been omitted to facilitate the explanation thereof, as indicated by the use of the ellipses), while the "ORDER" clause will order the result set by the StartTime, which is a field in the TestResults table. The "SELECT DISTINCT Sessions.*" clause only returns fields from the Sessions table (otherwise, columns would be obtained from both tables, which is not desirable). Using the "DISTINCT" keyword ensures that only distinct results are returned (i.e., duplicate rows are filtered out). Advantageously, the use of "Sessions.*", rather than just "*", ensures that only unique rows from the Sessions table are returned, rather unique rows from both the Sessions table and the TestResults table. The main benefit of executing the "INNER JOIN" command in the query string 338 of FIG. 14 is that any sessions, which contain no data (i.e., sessions that are empty), are removed from the record lists. As a result, the timeline bar is not populated with sessions having no data.

Turning again to FIG. 10, in step 306, each session record is read and then, in decision block 308, it is determined whether the date field in the session record exists in the existing timeline bar 202 for that particular patient. For example, the session record may have a "start time" field associated therewith (see FIG. 14) that contains the time and date on which the test was performed. If the date field does not exist in the timeline bar 202, then a new session group is created as a visual icon (e.g., 204, 206, 208, 222) in the timeline bar 202 (step 310). Next, in decision block 312 of FIG. 11, it is determined if the date field contains a year that is different from those presently included in the timeline bar 202. If the year in the date field is different from those presently included in the timeline bar 202 (e.g., the year 2008, which is not included in the timeline bar 202 of FIGS. 8 and 9), the spacing between the existing date icons and the added date icon(s) is increased (i.e., a noticeable gap is created by year groupings—see step 314 of FIG. 11). Also, in step 314, a visual border is created around date icon(s) from the same year. For example, see the added date icon 222 in FIG. 9 (Dec. 10, 2008), which has been illustrated using dashed lines in order to signify that it has been added to the timeline bar 202. However, if it is determined in decision block 308 of FIG. 10 that the date field in the session record exists in the existing timeline bar 202 for the particular patient, an existing session group visual icon is used (e.g., icon 204), and a visual line (e.g., dashed separating line 226 in FIG. 9) is created in the drop-down menu 212 to indicate multiple sessions on this same date (in step 316). For example, refer to the added session test 224 in FIG. 9 (i.e., mCTSIB test), which has been outlined with dashed lines in order to signify that it has been added to the drop-down menu 212.

Figure 11:
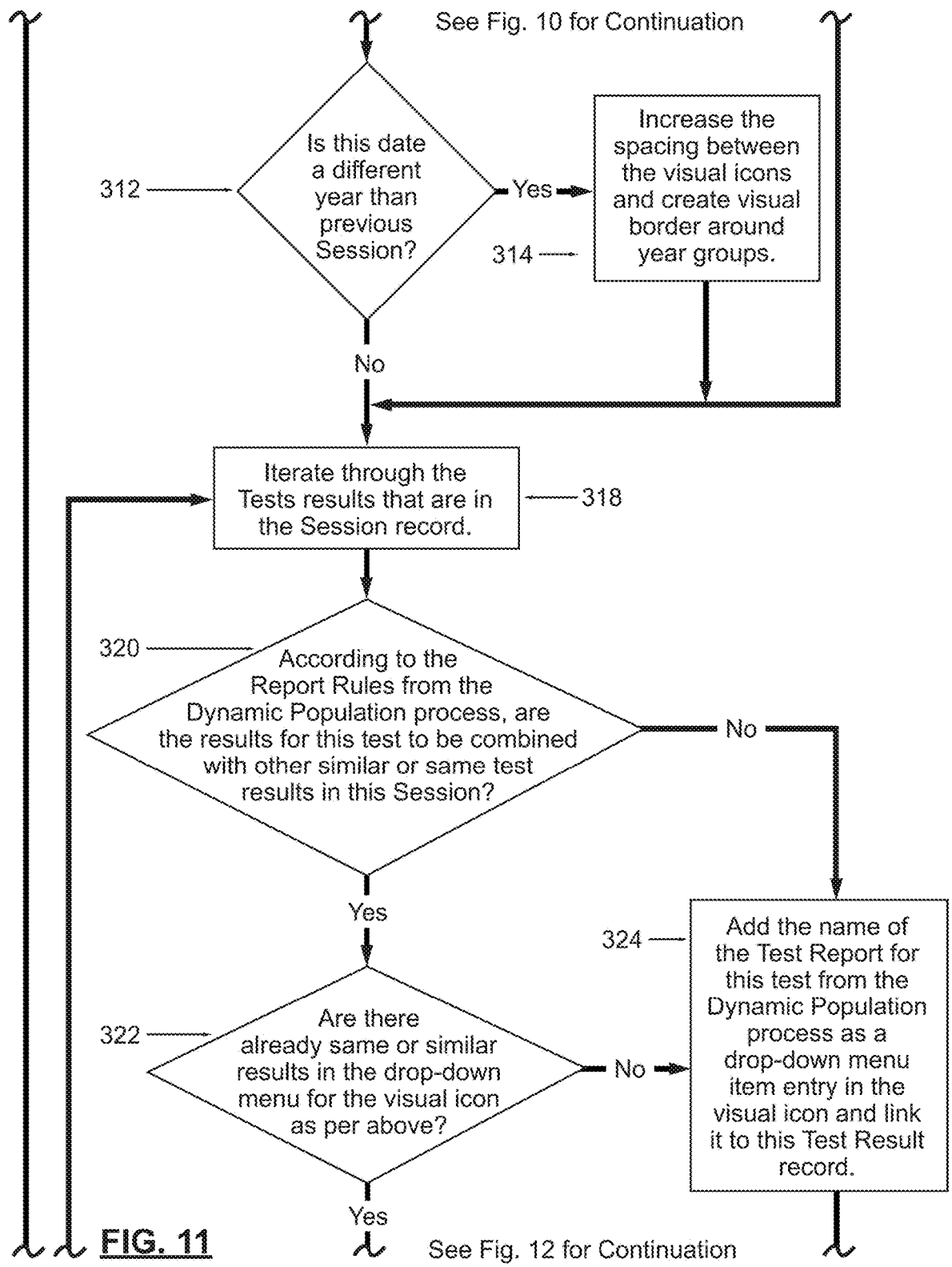
FIG. 11 is a continuation of the flowchart of FIG. 10, which illustrates additional steps of the timeline bar generation procedure, according to an embodiment of the invention.

In decision block 312 of FIG. 11, if it is determined that the date field contains a year that is the same as one of those presently included in the timeline bar 202 (e.g., the year 2009, which is included in the timeline bar 202 of FIGS. 8 and 9), then an iteration through the test results in the session record is performed in step 318. In the session record, each test result is identified using a unique GUID as the record identifier, which is used to identify and locate record (sessions and records of other types are also identified using unique GUIDs as well). After which, in decision block 320 of FIG. 11, it is determined whether, in accordance with the report rules from the dynamic population process, if the results for the particular test are to be combined with other similar or same test results in the session. For example, suppose the report rules comprise the following lines of code:

<!REPORTXML name="Standing Stability Report" type="TestReport"
testobject="BalanceTests.NSEO"
testobject="BalanceTests.NSEC"
testobject="BalanceTests.PSEO"

testobject="BalanceTests.PSEC"
reportcombines="*testobject*"
    reportcombinedtitle="Standing
Stability">

This example illustrates that the "Standing Stability Report" is to be used for the following test objects: BalanceTests.NSEO, BalanceTests.NSEC, BalanceTests.PSEO, and BalanceTests.PSEC. The keyword "reportcombines" is set with a special shorthand text "*testobject*" to instruct the system 100 to use the declared testobject keyword values; the code could also have been written as "reportcombines=BalanceTests.NSEO; BalanceTests. NSEC; BalanceTests.PSEO; and BalanceTests.PSEC", and the result would have been the same. As such, the reports generated from test results of the different types of balance tests are combined with the title "Standing Stability". In one embodiment, test reports comprise test results presented in a form that is readily ascertainable to a user (e.g., in graphical form).

If the results for the particular test are to be combined with other similar or the same test results in the session, then in decision block 322, it is further determined if the same or similar test results already exist in the drop-down menu (e.g., 212) for the visual icon (e.g., date icon 204) as described above. If the same or similar test results do not exist in the drop-down menu 212, then the name of the test report for this test from the dynamic population process will be added as a drop-down menu item entry (e.g., "mCTSIB" test 224 in drop-down menu 212) in the visual icon (e.g., date icon 204) and it will be linked to this test result record (step 324). The name of the test report for this test also will be added as a drop-down menu item entry if, in decision block 320, it is determined that, according to the report rules from dynamic population process, the results for the particular test are not to be combined with other similar or same test results in the session (refer to FIG. 11).

Figure 12:
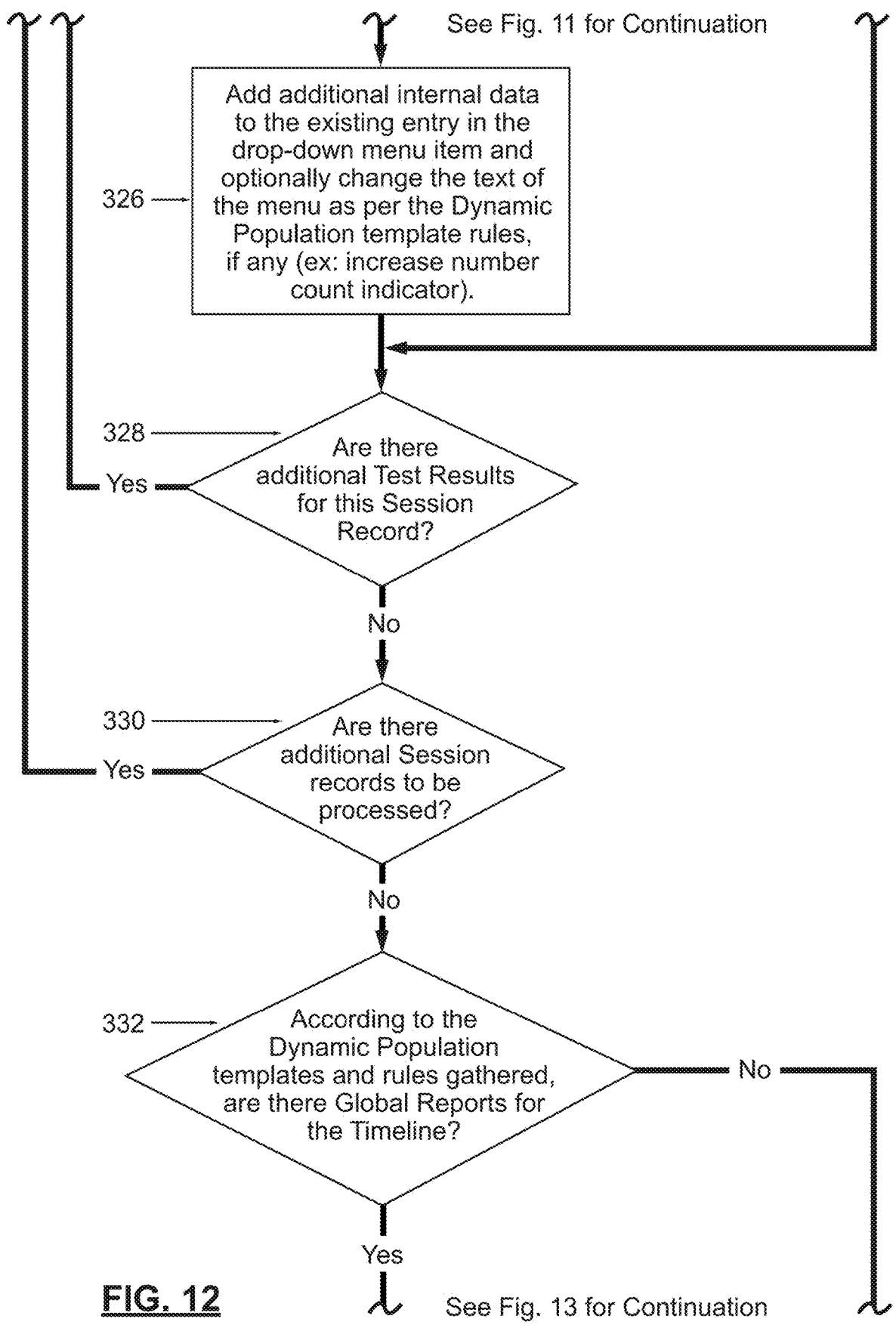
FIG. 12 is a continuation of the flowchart of FIG. 11, which illustrates additional steps of the timeline bar generation procedure, according to an embodiment of the invention.
Figure 13:
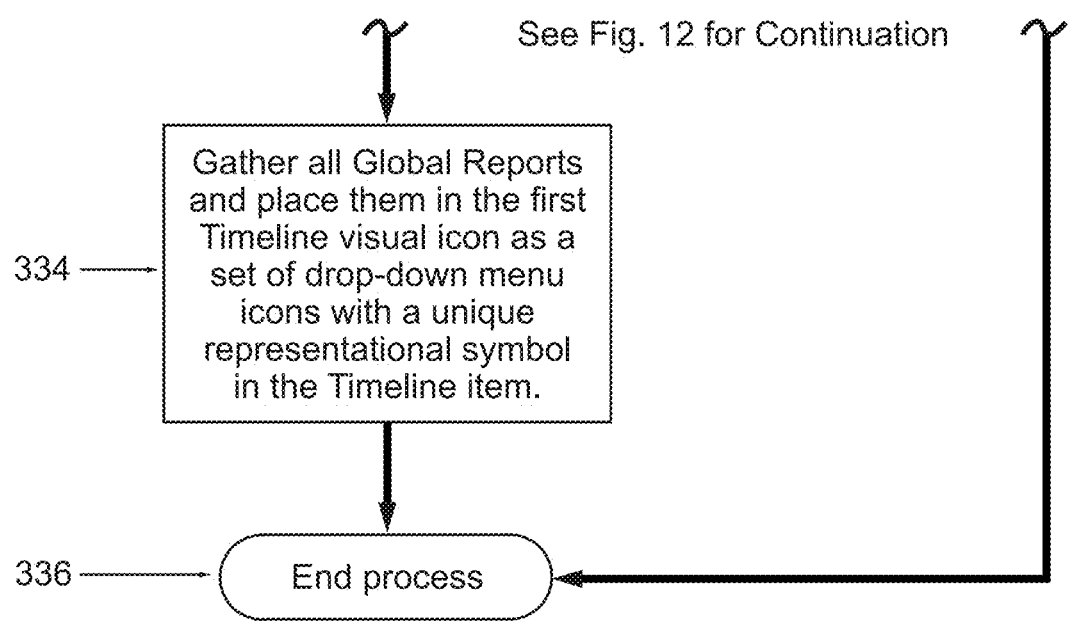
FIG. 13 is a continuation of the flowchart of FIG. 12, which illustrates additional steps of the timeline bar generation procedure, according to an embodiment of the invention.

In decision block 322, if it is determined that the same or similar test results already exist in the drop-down menu (e.g., 212) for the visual icon (e.g., date icon 204), then additional internal data is added to an existing entry in the drop-down menu item (see step 326 in FIG. 12). In some embodiments, the text of the menu item can be changed per the dynamic population template rules (e.g., a parenthetical number may be placed next to the entry in the drop-down menu 212—see FIG. 9). Next, in decision block 328 of FIG. 12, it is determined whether there are any additional test results for this session record. If there are any additional test results for this session record, then the process reverts back to step 318 in FIG. 11, wherein an iteration through the test results that are in the session record is performed. If there are not any additional test results for this session record, then the process proceeds to decision block 330, wherein it is determined if there are any additional session records that are to be processed. If it is determined in decision block 330 that there are additional session records that require processing, then the process reverts back to step 306 in FIG. 10, wherein each session record is read. However, if it is determined at decision block 330 that there are not any additional session records that need to be processed, then the process proceeds to decision block 332.

Referring to decision block 332 in FIG. 12, it is next determined whether, according to the dynamic population templates and rules gathered, if there are global reports for the timeline bar 202. If there are global reports for the timeline bar 202, then, in step 334 of FIG. 13, those global report(s) are gathered and placed in the first timeline visual icon (e.g., patient information icon 210) as a set of drop-down menu icons with a unique representational symbol in the timeline item, and the process ends at 336. In contrast, if it is determined in decision block 332 that there are no global reports for the timeline bar 202, the process ends at step 336 in FIG. 13.

Figure 15:
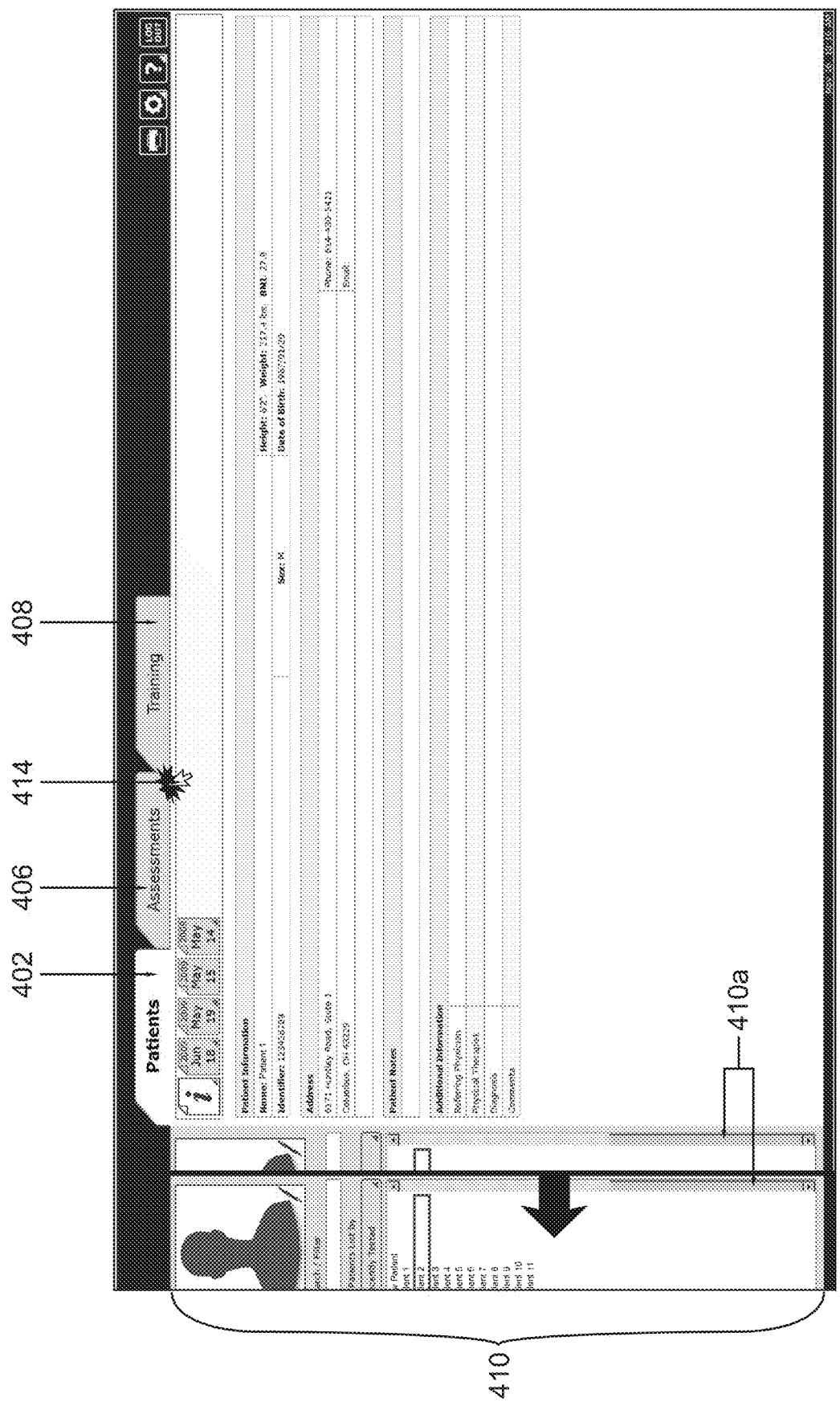
FIG. 15 is a first screenshot displayed on the operator visual display device of the measurement and testing system illustrating the mode change notification feature, according to an embodiment of the invention.
Figure 16:
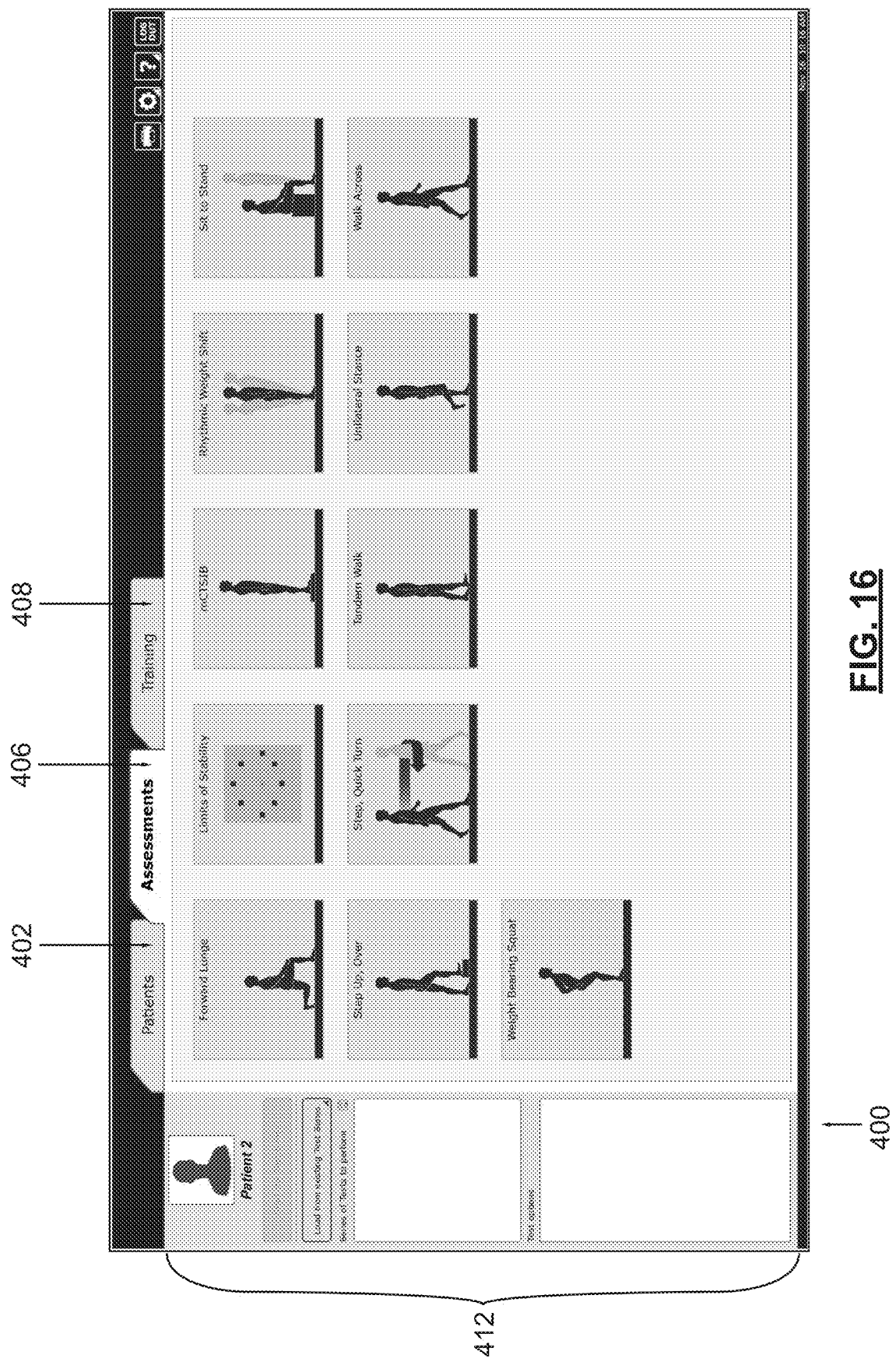
FIG. 16 is a second screenshot displayed on the operator visual display device of the measurement and testing system illustrating the mode change notification feature, according to an embodiment of the invention.

According to another aspect of the illustrative embodiment, with reference to FIGS. 15 and 16, the data acquisition/data processing device 104 of the measurement and testing system 100 is configured and arranged to generate a screen image 400 with a plurality of mode selection tabs 402, 406, 408 and a side bar menu 410 on the operator visual display device 130. When a user switches from a current mode of operation (e.g., patient data entry mode) to another mode of operation (e.g., assessment mode) by selecting one of mode selection tabs (e.g., 406) indicative of the another mode utilizing the user input device (e.g., keyboard 132 or mouse 134 by moving pointer 414 thereon), the data acquisition/data processing device 104 is configured to automatically displace the side bar menu 410 to an edge of the screen image 400. The displacement of the side bar menu 410 is a visual indicator of a system or process state change that is used to draw attention that a significant mode of operation has changed for the user that may otherwise happen without the user noticing it. In the illustrated embodiment of FIG. 15, the plurality of mode selection tabs 402, 406, 408 is disposed proximate to a top of the screen image 400 and the side bar menu 410 is disposed proximate to a lateral side of the screen image 400. When the data acquisition/data processing device 104 automatically displaces the side bar menu 410 to the edge of the operator visual display device 130, the side bar menu 410 is replaced by a new sidebar menu 412 (see FIG. 16) associated with the another mode (e.g., the assessment mode). When the data acquisition/processing device 104 automatically displaces the side bar menu 410 to the edge of the operator visual display device 130, an inner edge 410a (see FIG. 15) of the side bar menu 410 is gradually dragged towards an outer peripheral edge of the operator visual display device 130 in a continuous manner until the sidebar menu 410 is no longer visible to the user. The inner edge 410a of the side bar menu 410 remains generally parallel to the outer peripheral edge of the operator visual display device 130 as it dragged towards the outer peripheral edge thereof. Advantageously, the displacement of the side bar menu 410 off the output screen alerts the user of the measurement and testing system 100 that he or she is switching operational modes (i.e., switching the functional content of the software program). Otherwise, without the notification effect created by the displacement of the side bar menu 410, a user of the system 100 may not be readily unaware that he or she is switching modes.

Now, the specific functionality of the side bar menu displacement feature will be described in more detail. Initially, the data acquisition/data processing device 104 is programmed to take a graphical snapshot (e.g., a bitmap grab) of the screen image (e.g., screen image 400) on the operator visual display device 130 that is changing or switching contexts (i.e., when a user selects one of the tabs 402, 406, 408). The bitmap image is then placed into a top-level window container as the entire surface to be used. This top-level container (i.e., top-level meaning that it is above everything else) is displaced so as to be disposed almost exactly over top of where the source area is currently located, or was previously located. The operation mode is then changed, which results in the area that was made into a visual bitmap being erased and replaced with something else. Once this has occurred, the system notifies the animation routine to begin moving the bitmap image off the screen. In one embodiment, the graphical snapshot is animated so that it appears as if the side bar menu 410 is sliding off the output screen. For example, every 30 frames per second, the measurement and testing software program executed by the data acquisition/data processing device 104 moves the bitmap image across the output screen of the operator visual display device 130 and forces the area to redraw. After the animation has been completed (i.e., by the bitmap image moving completely off the screen), the bitmap and the top-level container are both discarded.

According to yet another aspect of the illustrative embodiment, the remote computing device 136, which is disposed at a first location, is specially programmed to generate one or more testing routines based upon input by a first system user. The data acquisition/data processing device 104 is configured to read the one or more testing routines generated by the remote computing device 136 and to integrate the one or more testing routines into the measurement and testing software program loaded thereon and executed thereby (i.e., dynamically populate the software program with new tests that are remotely generated). In other words, the one or more testing routines generated by the remote computing device 136 operate as an automatic plug-in to the measurement and testing software program (e.g., like a macro). The data acquisition/data processing device 104 of the measurement and testing system 100 is further configured to enable a second system user to utilize the one or more testing routines in the measurement and testing software program while data is acquired from a subject undergoing testing on the measurement assembly. Advantageously, this dynamic population feature of the measurement and testing software program allows the tests performed by the measurement and testing system 100 to be created and/or updated easily off-site, thereby obviating the need for the system end user to develop his or his own tests. Because the testing routines are typically written in a specific program code (e.g., HTML), and system end users are rarely trained software programmers, the dynamic population feature enables the measurement and testing software to be regularly updated without the need for system end users trained in software programming. Also, if end users of the measurement and testing software need to make only minor changes to the testing routines, they are able to change cosmetic features of test report output by utilizing a basic text editor, such as Microsoft® Notepad, for making changes to data labeling, and the like, in the program code.

Initially, the dynamic population feature of the measurement and testing software program reads a specific set of directories, and looks for a specific pattern of filenames (e.g., the software looks for HTML files under a specific set of directories). After which, the measurement and testing software program reads the content of the specific identified files, and looks for specific patterns of text. The patterns of text in the specific identified files inform the measurement and testing software program on the data acquisition/data processing device 104 how to organize the tests, the test reports, and the test outputs. For example, the first line of text in an exemplary HTML file may contain the following information: (i) the name of the test (e.g., Forward Lunge), (ii) the tab under which the test is to be located in the measurement and testing software program (e.g., Assessment), (iii) the grouping within the tab, if applicable (e.g., the "Training" tab includes groups, such as "Closed Chain", "Mobility", "Quick Training", "Seated", and "Weight Shifting"), and any predefined or custom options.

Figure 17:
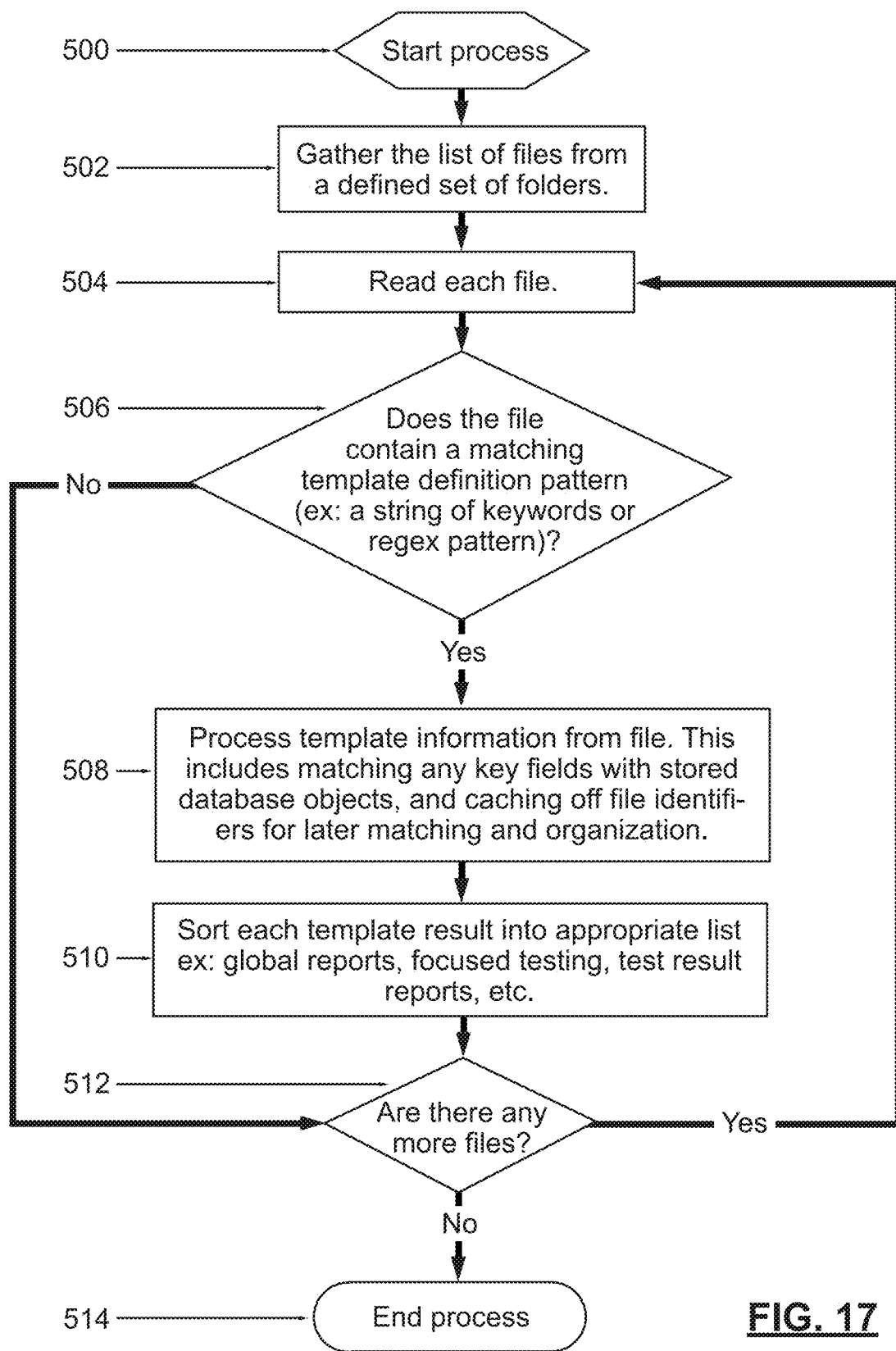
FIG. 17 is a flowchart illustrating the procedure by which the dynamic population feature of the measurement and testing system is carried out, according to an embodiment of the invention.

In accordance with this aspect of the illustrative embodiment, a flowchart illustrating the functionality of the dynamic population feature of the measurement and testing system 100 is set forth in FIG. 17. All of the steps described below with reference to the flowchart of FIG. 17 are carried out by the data acquisition/processing device 104. Referring to this figure, the procedure commences at 500, and in step 502, a list of files from a defined set of folders is gathered. For example, the testing software program looks for a specific file pattern (e.g., a specific extension) in a particular directory (e.g. a "Reports" directory) using a regular expression search routine (regex). After which, in step 504, each file is read and, at decision block 506, it is determined if the particular file contains report rules or a matching template definition pattern (e.g., with one or more key pairs). If the file does not contain a definition matching template pattern, the process proceeds to step 512, wherein it is determined if there are any more files. If the file does contain a definition matching template, the template information is processed from the file in step 508, which includes matching any key fields with stored database objects and caching off file identifiers for later matching and organization. The file identifiers (i.e., file names) are stored internally in the cache memory of the data acquisition/data processing device 104 so that the file identifiers do not have to be repeatedly read from a directory, thereby resulting in a performance advantage. As an example of how template information is processed from a file in step 508, suppose that the following three (3) files exist:

file #1: the test file:
<!TESTXML name="Limits of Stability" type="Assessment"
testobject="#LimitsOfStability">
file #2: the report file:
<!REPORTXML name="Limits of Stability" type="Assessment"
testobject="#LimitsOfStability"
reportcombines="*testobject*"
reportcombinedtitle="Limits of Stability">
file #3: the patient screen file:
<!PATIENTTESTXML name="Limits of Stability" type="Assessment"
testobject="#LimitsOfStability">

In the above example, the "test file" (i.e., file #1) determines the content on the operator visual display device 130, the "report file" (i.e., file #2) determines how the results of the tests are presented to a user, while the "patient screen file" (i.e., file #3) determines the content on the subject visual display device 106. The entries 'testobject="#LimitsOfStability" ' in the above files call up a subroutine for performing additional functionality (e.g., acting as a plug-in). In this example, a record with an associated record identifier (e.g., a number) is placed in a master database listing of tests, wherein the record indicates that the LimitsOfStability test is called "Limits of Stability" and is an "Assessment" type of test (as opposed to, for example, a "Training" or "Diagnostic" test. In other words, the "Limits of Stability" test would be entered under the "Assessments" tab 406 in FIG. 16. The record identifier in the master database listing of tests will then be used to locate the test file and test result processing code, as needed later on. The fields above, e.g., the name, type, test object, report title, and what the report combines, etc., are all stored in an internal object in the database. The end result being that there are three collections of data, which include: (i) a report collection, (ii) a test collection, and (iii) an optional patient screen collection. If the test does not have a matching patient screen, then it will default to using the existing test file (i.e., the patient screen will match the test screen on the operator visual display device 130). In addition, certain keywords such as "grouping" can be used to organize the tests into a visual collection of similar items, whereas keywords such as "package" and "series" can be used to define a predetermined series of tests that can be called up by the user by name. Also, tests that contain options, which may be set by a user, can additionally have an "option" keyword with additional text fields that determine the content of the options. Moreover, any other keywords can be processed by the system 100 as expansion needs arise.

In step 508, key fields (e.g., name="Limits of Stability", type="Assessment", and testobject="#LimitsOfStability" in the above example) are matched with stored database objects using a heuristic routine that looks for loaded results from the file system, and scans the database for existing records matching the type and test object. If the type and test object are found, then the name in the database is updated (e.g., if needed, the test is renamed). Conversely, if the database does not contain the type and test object, the system searches for a matching name. If the matching name is found, for example, the stored test object and type is updated (e.g., if the functionality of the test changed). If the database does not contain the test object or the name, then this is presumed to be a new test and the records for this new test are added in the database. Also, once the database has been scanned, any tests that existed before in the database, but do not presently have any matching files, are marked as inactive (because the system can no longer process the tests or show reports for them, but this could be a transient problem that reinstalling the test will fix, so nothing is deleted). For example, the tests or reports could have been inadvertently deleted by a system user.

Then, referring again to FIG. 17, in step 510, each template result is sorted into an appropriate list (e.g., global reports, focused testing, test result reports, etc.). For example, a global report may contain general patient information that is not associated with any particular test. If the report type is "global", then there is no test object assigned to this report, and it will be placed in the patient information icon (i.e., icon 210 in FIGS. 8 and 9). Next, at decision block 512, it is determined if there are any more files. If it is determined at step 512 that there are more files, then the process reverts back to step 504. If it is determined that there are no more files in step 512, the process ends at 514.

According to still another aspect of the illustrative embodiment, the data acquisition/data processing device 104 of the measurement and testing system 100 is configured and arranged to alert the user of the system when the one or more signals from the at least one transducer of the measurement assembly 102 are no longer detected by generating a quasi-instantaneous visual indicator on the operator visual display device 130. In general, in order to implement this feature, a specially programmed timing routine is incorporated in the force plate driver. If the specially programmed timing mechanism does not receive data from the force measurement assembly 102 in a predetermined amount of time, it will signal to the primary application program (i.e., a higher level software program) that the force measurement assembly 102 has been disconnected or has failed. In one embodiment, the predetermined amount of time ranges from approximately 100 milliseconds to approximately 3 seconds (or from 100 milliseconds to 3 seconds). The specially programmed timing routine is embodied in steps 704, 714, and 720 described below with respect to the flowchart of FIGS. 19 and 20. The high end of the range is intended to give a user of the measurement and testing system 100 enough time to reconnect the force measurement assembly 102 to the data acquisition/data processing device 104 (i.e., enough time to reconnect electrical cable 118).

Figure 18:
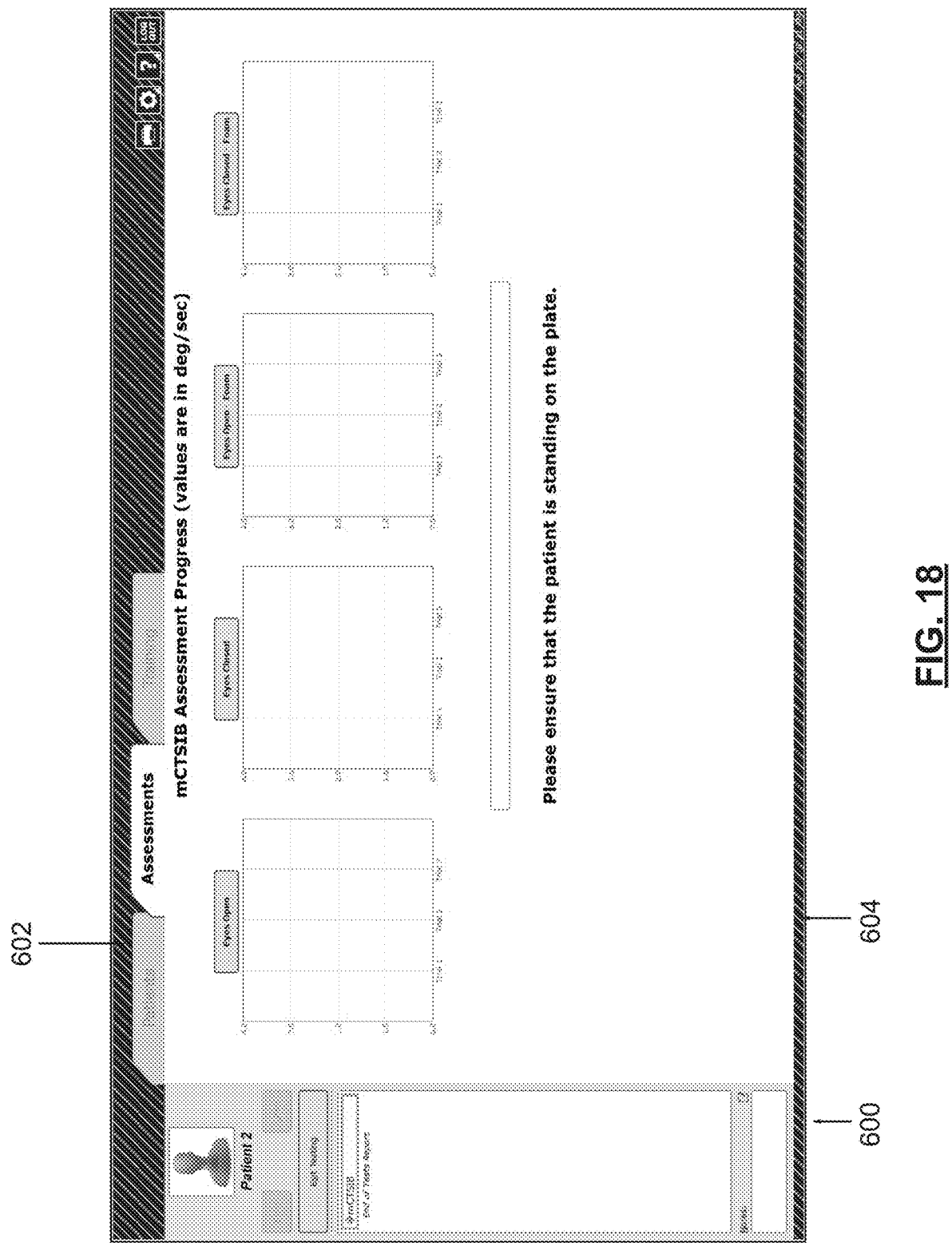
FIG. 18 is a screenshot displayed on the operator visual display device of the measurement and testing system illustrating the signal loss alert feature, according to an embodiment of the invention.

Referring to FIG. 18, the manner in which the quasi-instantaneous visual indicator is displayed on the operator visual display device 130 will be explained. Preferably, the visual indicator displayed on the operator visual display device 130 comprises a change in a background color of a screen image 600. More particularly, the change in the background color of the screen image 600 comprises changing the top border 602 and the bottom border 604 of the screen image 600 from a first color to a second color. In FIG. 18, because this is a black-and-white image, the change in the color of the top and bottom border 602, 604 is indicated through the use of a hatching pattern (i.e., a diagonal hatching pattern). In one embodiment of the invention, the first color of the top and bottom border 602, 604 is dark blue, while the second color of the top and bottom border 602, 604 is bright red. Bright red is chosen for the second color because it readily attracts the attention of the user so that corrective measures may be immediately taken thereby.

Figure 19:
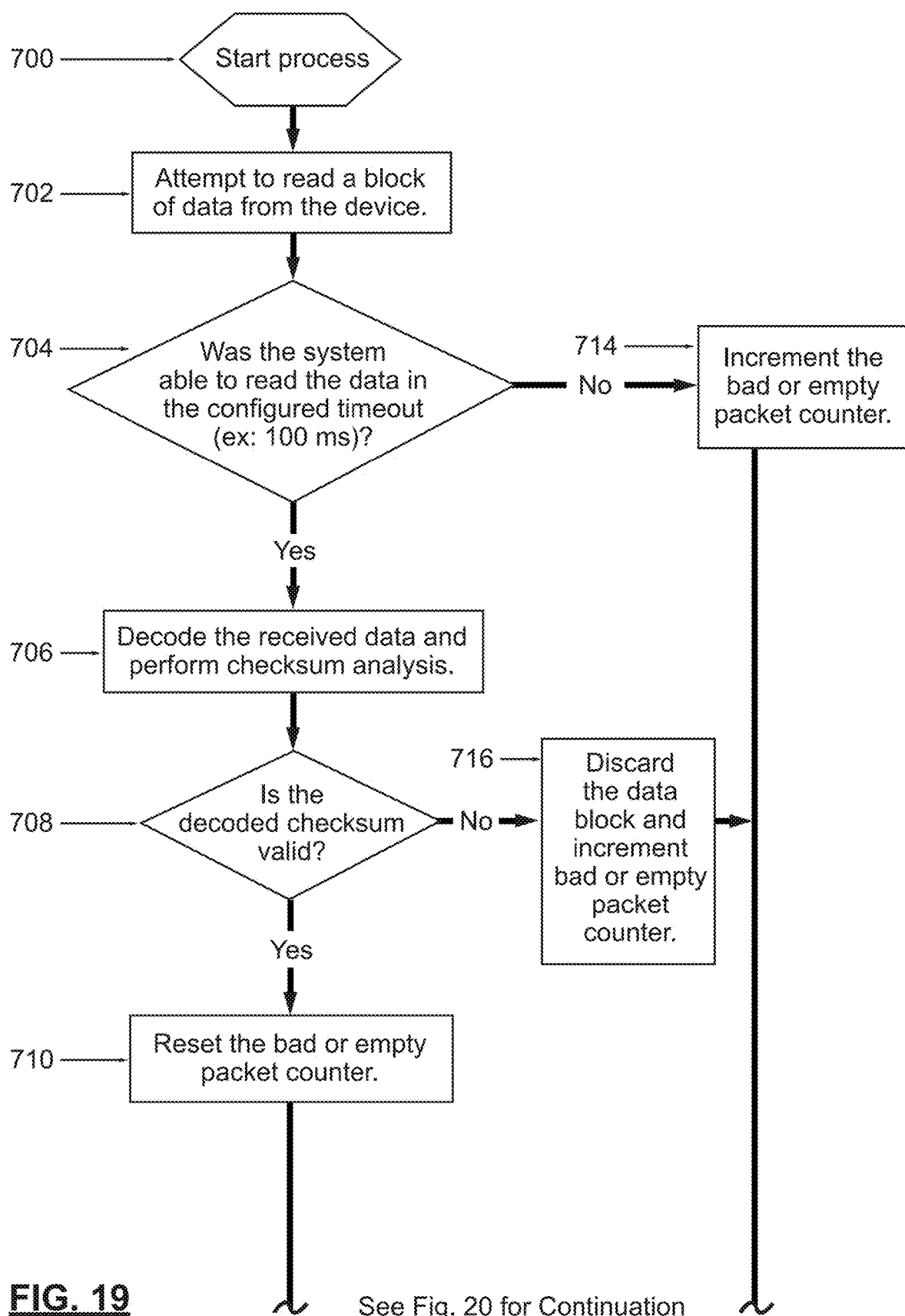
FIG. 19 is a flowchart illustrating the procedure by which the signal loss alert feature of the measurement and testing system is carried out, according to an embodiment of the invention.
Figure 20:
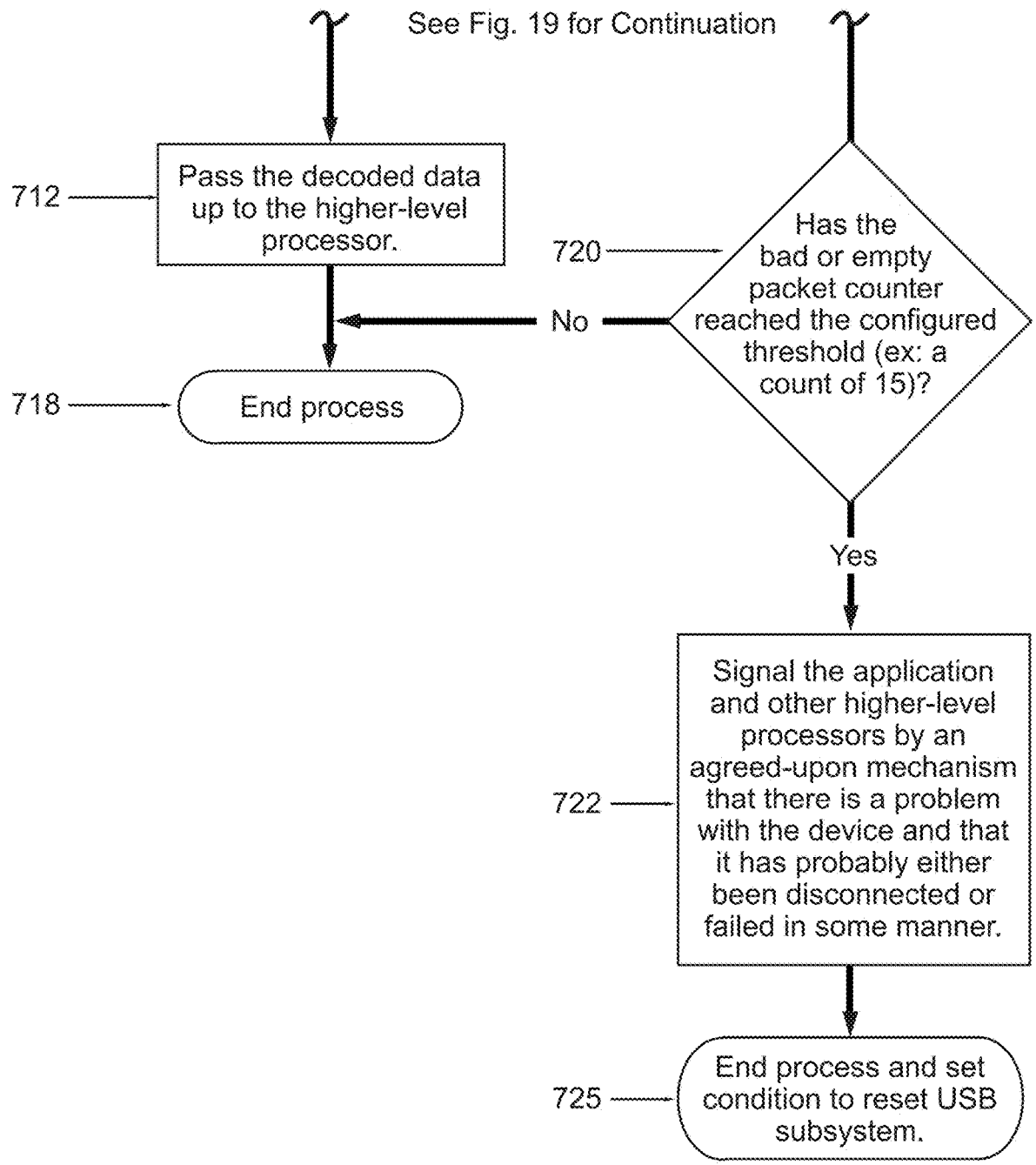
FIG. 20 is a continuation of the flowchart of FIG. 19, which illustrates additional steps of the procedure by which the signal loss alert feature of the measurement and testing system is carried out, according to an embodiment of the invention.

In accordance with this aspect of the illustrative embodiment, a flowchart illustrating the functionality of the measurement assembly disconnect/failure alert feature of the measurement and testing system 100 is set forth in FIGS. 19 and 20. The process described herein assumes that the USB communication system has already been established with the measurement assembly 102 (i.e., force plate), in accordance with the hardware chipset provider's specifications. In general, this requires the opening of a USB connection and looking for specific device signatures. All of the steps described below with reference to the flowcharts of FIGS. 19 and 20 are carried out by the data acquisition/processing device 104. Referring to this figure, the procedure commences at 700, and in step 702, an attempt is made to read a block of data (i.e., transmitted in one or more signals) from the one or more measurement devices (i.e., one or more force transducers) of the force measurement assembly 102. After which, at decision block 704, it is determined whether the data is able to be read in a predetermined amount of time (e.g., a predetermined timeout of 100 milliseconds). If the data is able to be read in a predetermined amount of time, then, in step 706, the received data is decoded and a checksum analysis is performed. The checksum analysis is performed in order to ensure the integrity of the raw data from the force measurement assembly 102. For example, the checksum analysis may utilize a particular cyclic redundancy check (CRC), such as a CRC-16. Conversely, if the data is not able to be read in the predetermined time period, the bad or empty packet counter is incremented in step 714. A bad packet is indicative of a bad checksum, whereas an empty packet counter signifies the receipt of empty data.

After the checksum analysis is performed in step 706, at decision block 708, it is determined whether the decoded checksum is valid. If the decoded checksum is determined to be valid, the bad or empty packet counter is reset in step 710. Then, in step 712 of FIG. 20, the decoded data is passed up to the higher level processor (i.e., a high level software program, such as the measurement and testing software program, which is a type of data collection and analysis software program), and the process ends at step 718. However, if the decoded checksum is determined to be invalid in step 708, the data block is discarded and the bad or empty packet counter is incremented in step 716.

Referring again to FIG. 19, if the bad or empty packet counter has been incremented in either step 714 or 716, it is determined, in decision block 720 of FIG. 20, whether or not the bad or empty packet counter has reached the configured threshold (e.g., a predetermined number of packets of data). The predetermined number of packets of data can be set based upon the amount of noise that is tolerable in the system 100. The predetermined number of packets of data may also set in accordance with the type of measurement assembly (e.g., force measurement assembly 102) that is operatively coupled to the data acquisition/data processing device 104. For example, if a complex force measurement assembly 102 (e.g., having a large number of separate plates or measurement surfaces) is connected to the data acquisition/data processing device 104, then a small predetermined number of packets may be set (e.g., 2 packets). In contrast, if a simpler force measurement assembly 102 is coupled to the data acquisition/data processing device 104, then a larger predetermined number of packets may be tolerable (e.g., 15 packets). If the bad or empty packet counter has not reached the configured threshold, the process ends at step 718. Otherwise, if the bad or empty packet counter has reached the configured threshold in step 720, the application and the other high-level processors (e.g., the measurement and testing software program) are signaled by an agreed-upon mechanism in step 722, which indicates that there is a problem with the force measurement assembly 102 and that it has probably either been disconnected or failed in some manner. After completing step 722, the process ends, and a condition is set to reset the USB subsystem at 725.

According to yet another aspect of the illustrative embodiment, referring to FIGS. 21-25, the data acquisition/data processing device 104 of the measurement and testing system 100 is configured and arranged to generate one or more subject global or progress reports (see e.g., the Forward Lunge Progress Report in FIG. 23) utilizing the output data acquired during one or more of the plurality of sessions, generate a subject information icon on the output screen of the visual display device, and assign the one or more subject global reports to the subject information icon. In this embodiment, the output data is arranged in a plurality of sessions, and output data that is acquired during the performance of a successive series of tests is arranged in a single session of the plurality of sessions. In general, the global/progress reports collect information (e.g., output data) from individual sessions and display the aggregate results in one overall report (e.g., the exemplary report illustrated in FIG. 23). As such, the information contained in a typical global/progress report is based upon output data collected on a plurality of different dates (i.e., the typical global/progress report spans across multiple days). While the global/progress reports may contain less detailed information than that which is available by accessing the reports for individual sessions themselves (i.e., by using the date icons of the timeline bar), the global/progress reports enable a system user to get an overall look at a particular subject's test performance over a period of time (e.g., over several days) without the need to laboriously click on each and every individual session in the date icons of the timeline bar. As such, the global/progress reports advantageously allow a system user to more quickly ascertain a subject's overall performance during a certain test by simply clicking on a single entry in a drop-down menu.

Figure 21:
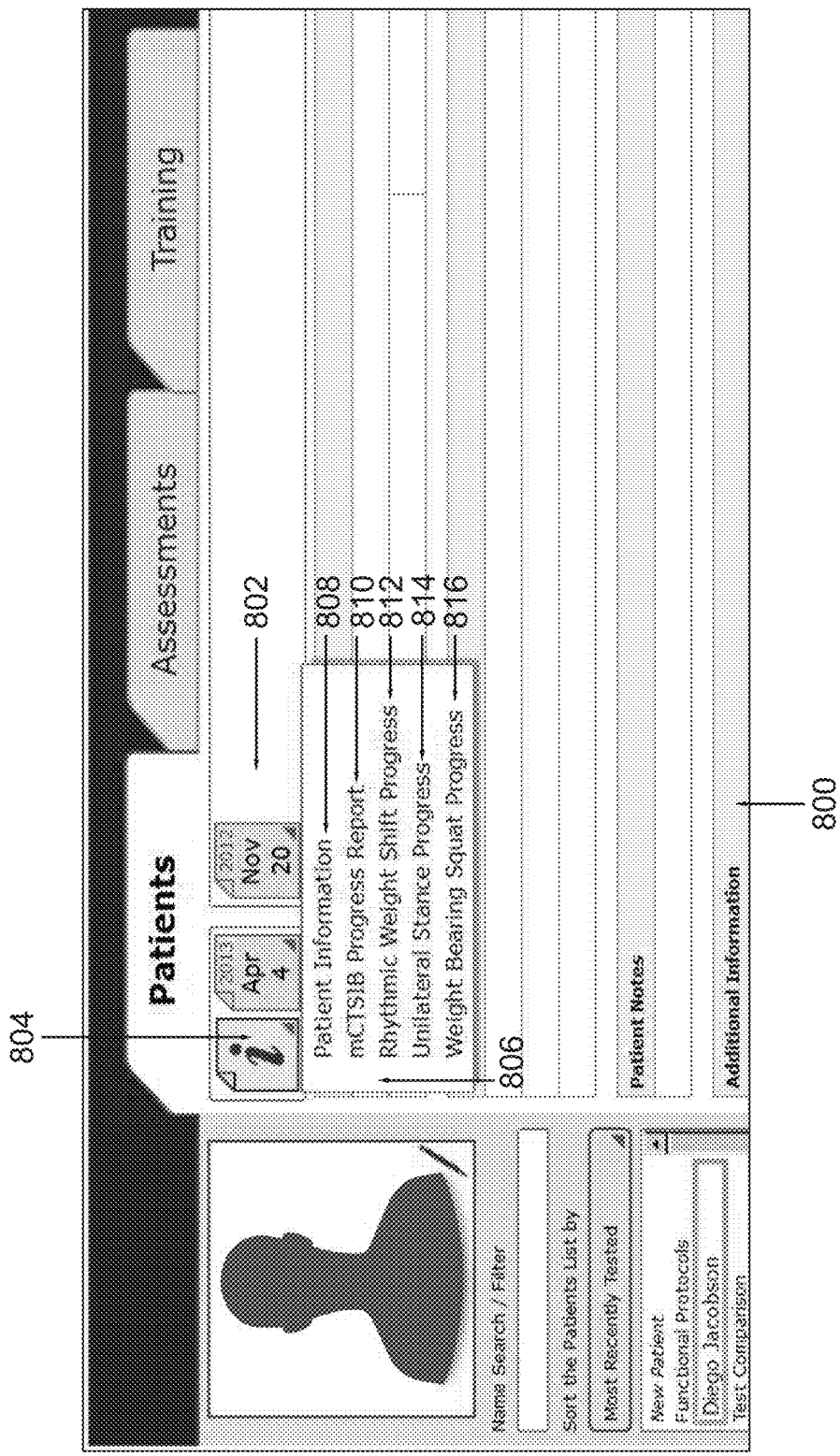
FIG. 21 is a partial screenshot displayed on the operator visual display device of the measurement and testing system illustrating a first plurality of global/progress reports that a system user is able to select, according to an embodiment of the invention.

With particular reference to FIG. 21, it can be seen that the data acquisition/data processing device 104 of the measurement and testing system 100 is configured and arranged to generate a screen image 800 that includes a timeline bar 802 with a subject (patient) information icon 804 having a plurality of entries 808-816 arranged in a drop-down menu 806. Specifically, as shown in the exemplary screenshot of FIG. 21, the entries in the drop-down menu 806 include: (i) patient information 808 (e.g., background information regarding the patient, such as height, weight, home address, contact information, name of physician, etc.), (ii) a first global/progress report 810 for a mCTSIB test (i.e., mCTSIB Progress Report), (iii) a second global/progress report 812 for a rhythmic weight shift test (i.e., Rhythmic Weight Shift Progress), (iv) a third global/progress report 814 for a unilateral stance test (i.e., Unilateral Stance Progress), and (v) a fourth global/progress report 816 for a weight bearing squat test (i.e., Weight Bearing Squat Progress). As shown in FIG. 21, each of the plurality of subject global/progress reports in the drop-down menu 806 is vertically spaced apart from the other reports included therein.

Figure 22:
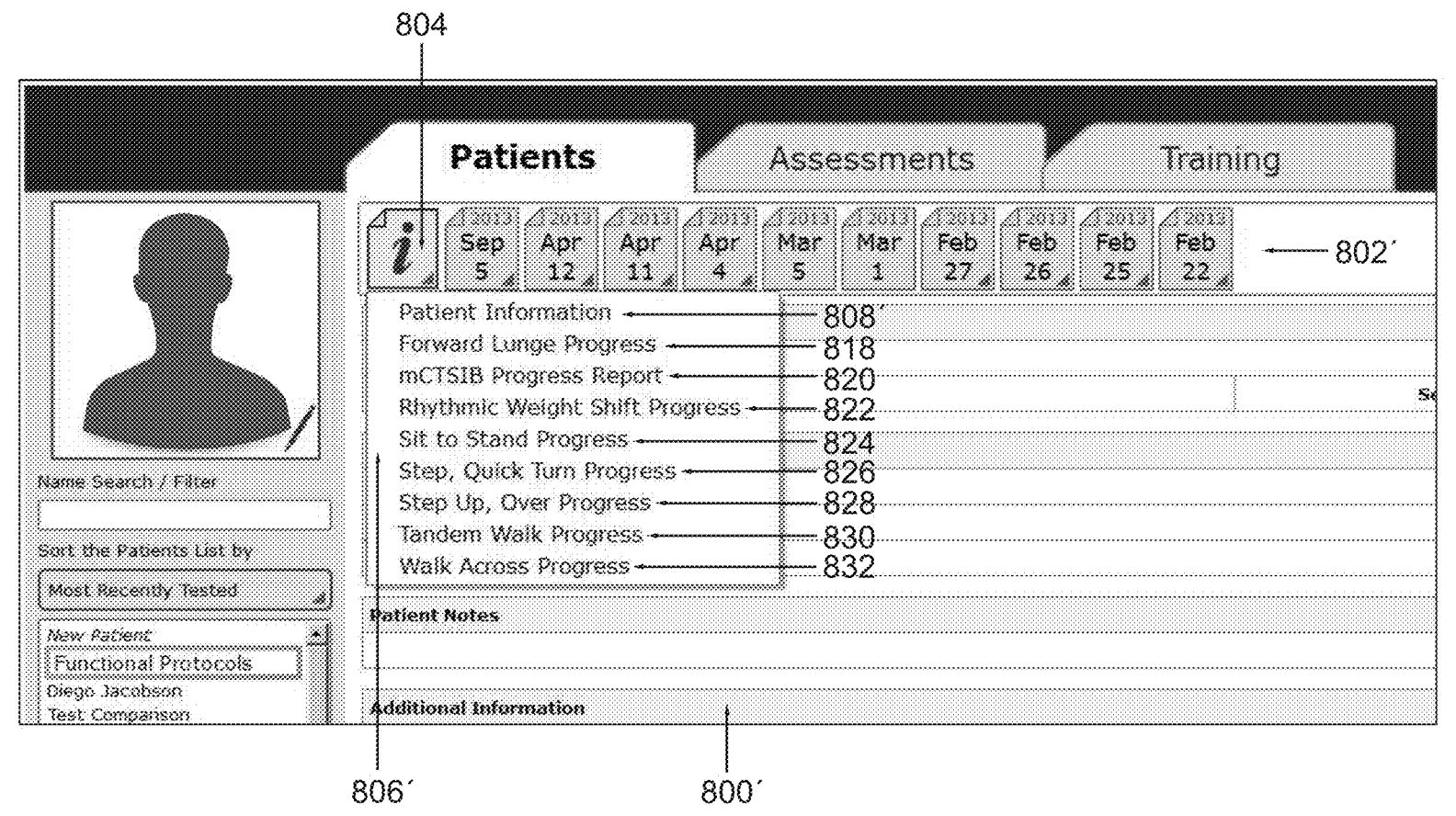

Another exemplary screenshot 800' is depicted in FIG. 22. Similar to the screenshot 800 illustrated in FIG. 21, the screenshot 800' of FIG. 22 includes a timeline bar 802' with a subject (patient) information icon 804 having a plurality of entries 808' and 818-832 arranged in a drop-down menu 806'. The drop-down menu 806' in the screenshot 800' contains significantly more global/progress report entries 818-832 than that illustrated in the screenshot 800 of FIG. 21. Specifically, in addition to the patient information 808', the drop-down menu 806' includes the following entries: (i) a first global/progress report 818 for a forward lunge test (i.e., Forward Lunge Progress), (ii) a second global/progress report 820 for a mCTSIB test (i.e., mCTSIB Progress Report), (iii) a third global/progress report 822 for a rhythmic weight shift test (i.e., Rhythmic Weight Shift Progress), (iv) a fourth global/progress report 824 for a sit to stand test (i.e., Sit to Stand Progress), (v) a fifth global/progress report 826 for a step, quick turn test (i.e., Step, Quick Turn Progress), (vi) a sixth global/progress report 828 for a step up, over test (i.e., Step Up, Over Progress), (vii) a seventh global/progress report 830 for a tandem walk test (i.e., Tandem Walk Progress), and (viii) an eighth global/progress report 832 for a walk across test (i.e., Walk Across Progress).

Figure 23:
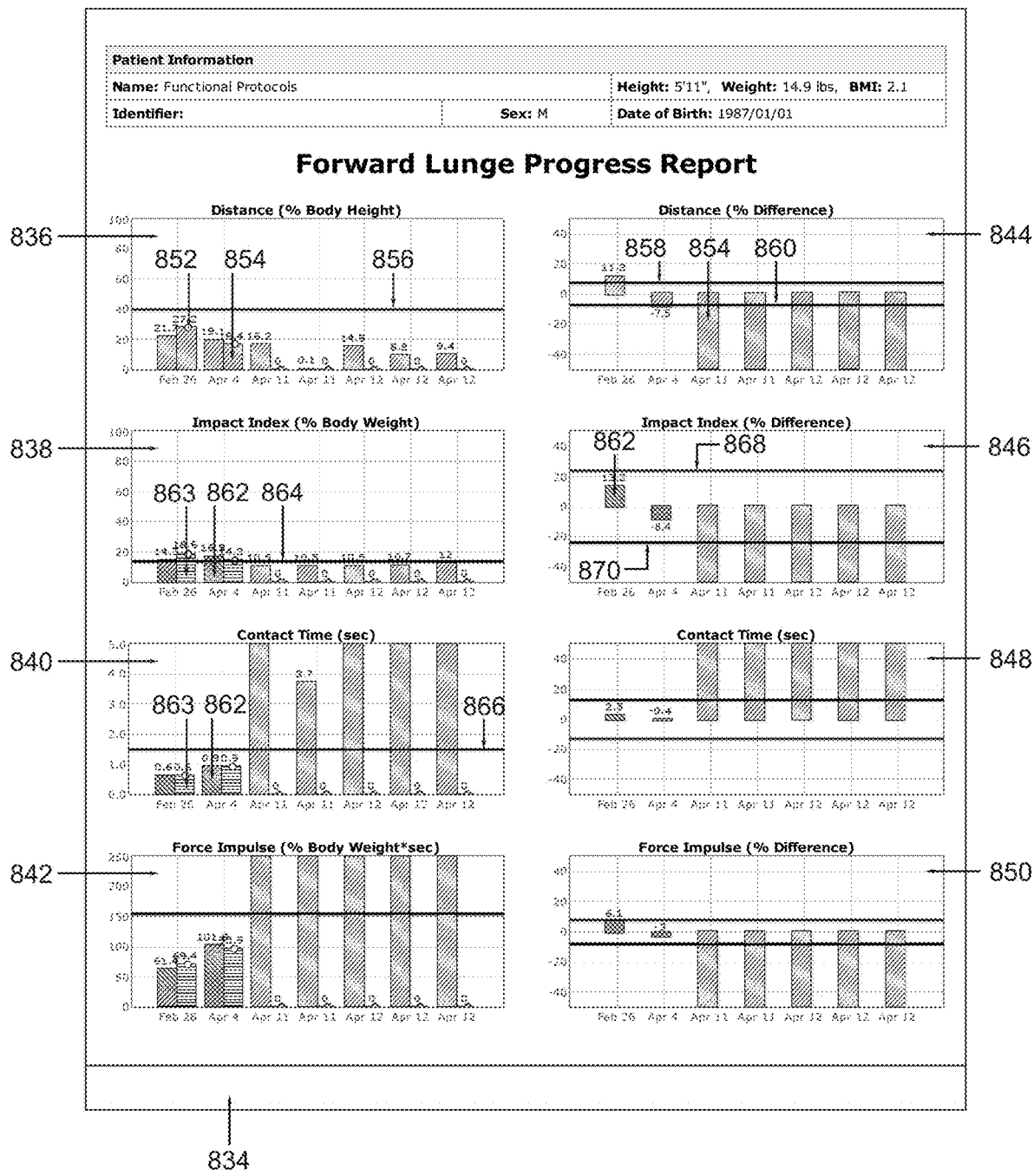
FIG. 23 is a screenshot displayed on the operator visual display device of the measurement and testing system illustrating an exemplary global/progress report generated by the measurement and testing system, according to an embodiment of the invention.

Next, with reference to FIG. 23, the content of an exemplary global/progress report will be described. In FIG. 22, if a system user were to click on the "Forward Lunge Progress" entry 818 in the drop-down menu 806', a report similar to that illustrated in FIG. 23 would be displayed on the screen. As shown in FIG. 23, the exemplary report 834 (i.e., the Forward Lunge Progress Report) contains a plurality of graphs 836-850 (i.e., eight (8) graphs arranged in four (4) rows and two (2) columns). Each of these graphs 836-850 includes output data that was acquired during a plurality of sessions on a plurality of days (e.g., February 26th, April 4th, April 11th, and April 12th). In each of the graphs 836-850, it can be seen that February 26th and April 4th are only listed once along the x-axis, while April 11th is listed twice, and April 12th is listed three times. This is because only a single session of the forward lunge test was performed on both February 26th and April 4th, while two sessions of the test were performed on April 11th, and three sessions of the test were performed on April 12th. The graphs disposed in the left-hand column of FIG. 23 include results for both the right and left legs of the subject or patient. The results for the right leg of the subject are differentiated from the results for the left leg of the subject by placement of a small circle 852 at the top of the bars pertaining to the right leg output results.

As illustrated by the exemplary report 834 of FIG. 23, the data acquisition/data processing device 104 is further configured and arranged to automatically alert a system user when one or more test results displayed in the one or more subject global reports are outside a predetermined range, below a normal value (e.g., below an average value for healthy subjects within a particular age group), or above a baseline value by generating a first visual indicator on the output screen of the visual display device. In general, the measurement and testing system 100 indicates that test results are outside a predetermined range, below a normal value, or above a baseline value by using a red color to display those results on the output screen of the visual display device. Although, because FIG. 23 is a black-and-white image, test results that are outside a predetermined range, below a normal value, or above a baseline value are indicated through the use of a first hatching pattern (i.e., a diagonal hatching pattern, to indicate those results that would appear in "red" on the output screen). For example, referring to graph 836 in FIG. 23 (entitled Distance (% Body Height)), it can be seen that all of the bars in this graph are denoted with the diagonal hatching pattern 854 to indicate that they are all below a normal value (i.e., 40%) indicated by the indicator line 856 extending generally horizontally across the graph 836 at the 40% value on the y-axis of the graph. The results displayed in the graph 836 indicate that the patient or subject performing the forward lunge test did not lunge forward the normal percentage distance for a person his or her age during any of the testing sessions. The 40% value (i.e., lunge distance as a percentage of body height), which is denoted using threshold line 856, represents the normal value for a person who is approximately the subject's same age (e.g., based on an average value for healthy subjects). As another example, referring to graph 844 in FIG. 23 (entitled Distance (% Difference)), it can be seen that all of the bars in this graph are denoted with the diagonal hatching pattern 854 to indicate that they are all outside a predetermined range or band (i.e., as indicated by the bounding lines 858, 860 extending generally horizontally across the graph 844). The results displayed in the graph 844 indicate that the patient or subject performing the forward lunge test had an abnormal percent difference in the distance achieved by his or her right leg as compared to his or her left leg for all of the testing sessions. The distance, expressed as a percent difference between the two legs, should have fallen within the band bounded by lines 858, 860 if the subject had results in the normal range. In general, it can be seen that the graphs 836-842 on the left-hand side of the report 834 are concerned with whether or not the patient or subject is above or below a single normal value, while the graphs 844-850 on the right-hand side of the report 834 are concerned with whether or not the patient or subject is within a normal percentage band of difference between the right and left legs. That is, each of the graphs 844-850 on the right-hand side of the report 834 focuses on the percentage difference between the two legs of the subject.

As also illustrated by the exemplary report 834 of FIG. 23, the data acquisition/data processing device 104 is additionally configured and arranged to automatically alert the user of the system when one or more test results displayed in the one or more subject global reports are within a predetermined range, above a normal value (e.g., above an average value for healthy subjects within a particular age group), or below a baseline value by generating a second visual indicator on the output screen of the visual display device, which is distinct from the first visual indicator. In general, the measurement and testing system 100 indicates that test results are within a predetermined range, above a normal value, or below a baseline value by using a green color to display those results on the output screen of the visual display device. Although, because FIG. 23 is a black-and-white image, test results that are within a predetermined range, above a normal value, or below a baseline value are indicated through the use of second and third hatching patterns (i.e., a criss-cross and horizontal line style hatching patterns, to indicate those results that would appear in "green" on the output screen). For example, referring to graph 838 in FIG. 23 (entitled Impact Index (% Body Weight)), it can be seen that the bars in this graph for the sessions occurring on February 26th and April 4th are denoted with a criss-cross style hatching pattern 862 (i.e., for the left foot of the subject) and a horizontal line style hatching pattern 863 (i.e., for the right foot of the subject) to indicate that they are all above a normal value (e.g., approximately 15%) indicated by the indicator line 864 extending generally horizontally across the graph 838 at the approximately 15% value on the y-axis of the graph. The results displayed in the graph 838 indicate that, on both February 26th and April 4th, the patient or subject performing the forward lunge test had an impact index that exceeded the normal value for a person who is approximately the subject's same age. As another example, referring to graph 840 in FIG. 23 (entitled Contact Time (sec)), it can be seen that the bars in this graph for the sessions occurring on February 26th and April 4th are denoted with the criss-cross style hatching pattern 862 (i.e., for the left foot of the subject) and the horizontal line style hatching pattern 863 (i.e., for the right foot of the subject) to indicate that they are below a baseline value (e.g., approximately 1.5 seconds) indicated by the indicator line 866 extending generally horizontally across the graph 840 at the approximately 1.5 second value on the y-axis of the graph. The results displayed in the graph 840 indicate that, on both February 26th and April 4th, the patient or subject performing the forward lunge test had a contact time that was below the baseline value for a person who is approximately the subject's same age. As yet another example, referring to graph 846 in FIG. 23 (entitled Impact Index (% Difference)), it can be seen that the bars in this graph for the sessions occurring on February 26th and April 4th are denoted with the criss-cross style hatching pattern 862 to indicate that they are both within a predetermined range or band (i.e., as indicated by the bounding lines 868, 870 extending generally horizontally across the graph 846). The results displayed in the graph 846 indicate that the patient or subject performing the forward lunge test had a normal percent difference in the impact index achieved by his or her right leg as compared to his or her left leg for the testing sessions performed on February 26th and April 4th. On these two days, the impact index, expressed as a percent difference between the two legs, fell within the normal band bounded by lines 868, 870 for results in a normal range.

Figure 24:
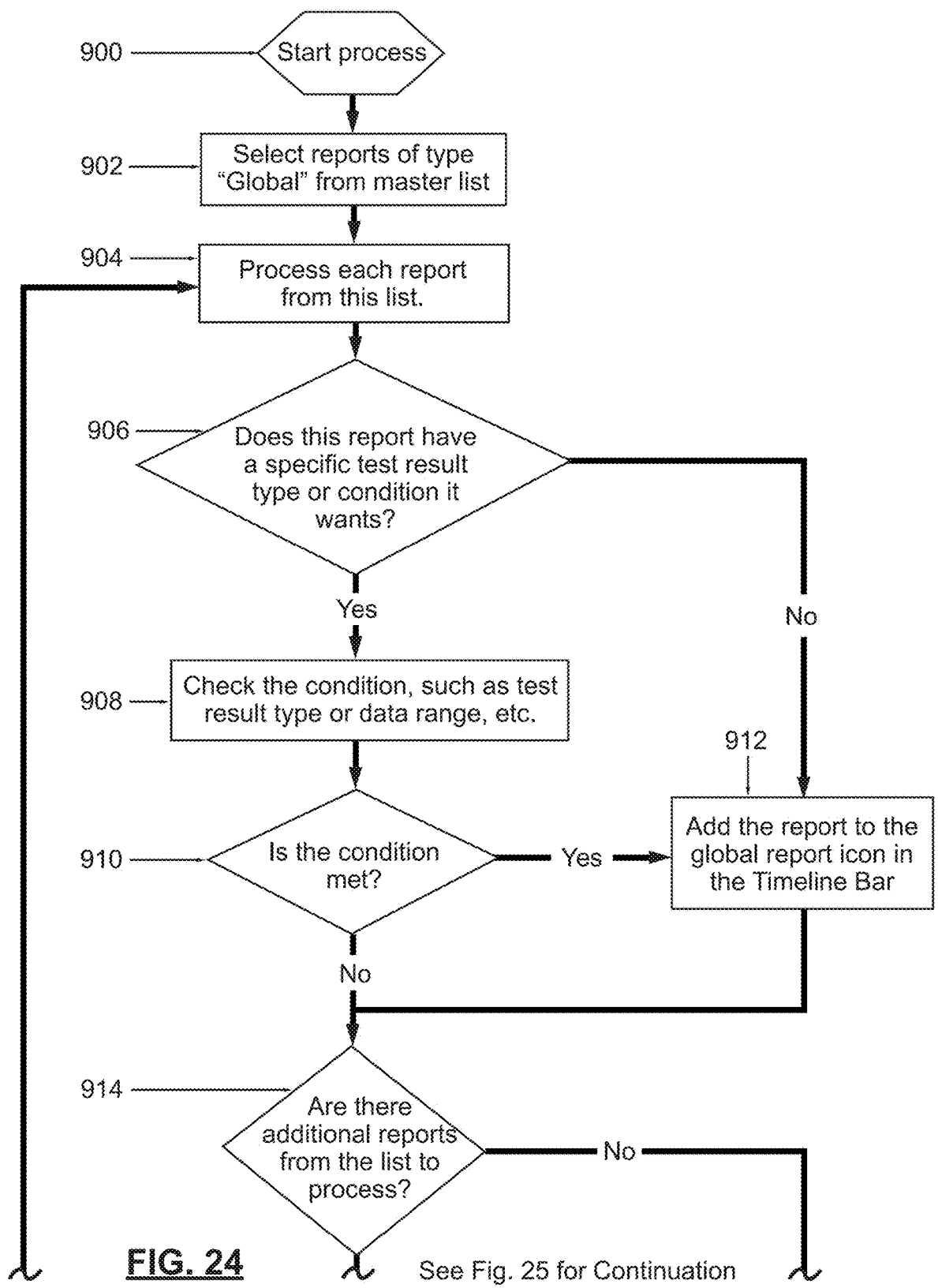
FIG. 24 is a partial flowchart illustrating a manner in which global/progress reports are generated by the measurement and testing system, according to an embodiment of the invention.
Figure 25:
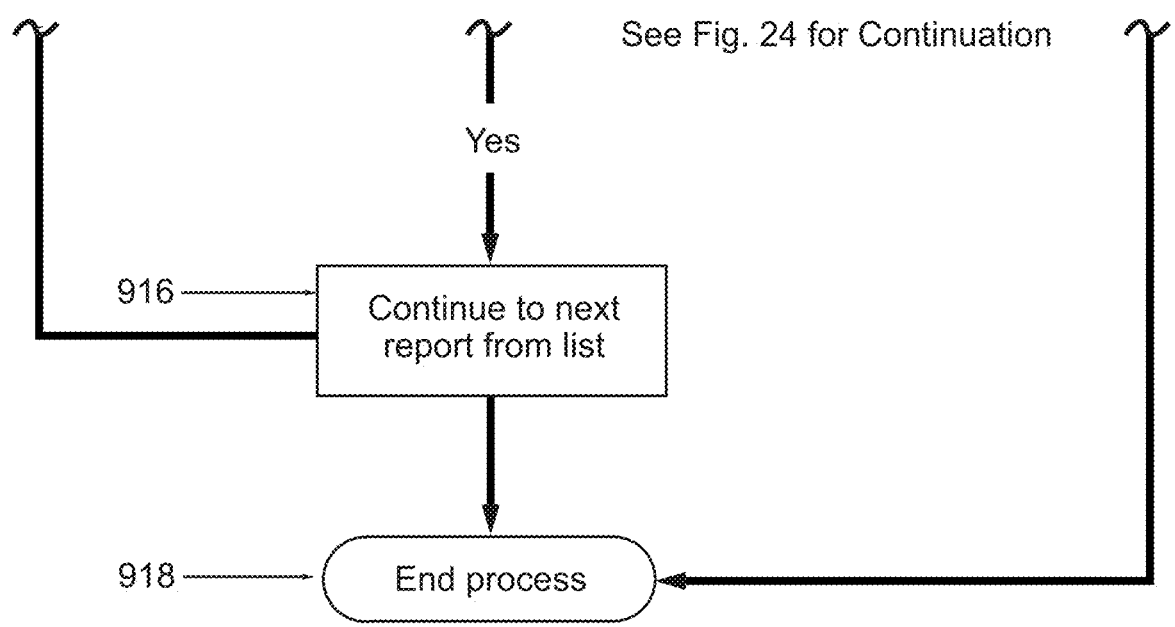
FIG. 25 is a continuation of the flowchart of FIG. 24, which illustrates additional steps of the global/progress report generation procedure, according to an embodiment of the invention.

In accordance with this aspect of the illustrative embodiment, a flowchart illustrating the functionality of the global/progress reports feature of the measurement and testing system 100 is set forth in FIGS. 24 and 25. All of the steps described below with reference to the flowcharts of FIGS. 24 and 25 are carried out by the data acquisition/processing device 104. Referring to this figure, the procedure commences at 900, and in step 902, reports of a "Global" type are selected from a master list. In step 902, a list of files is dynamically built by the measurement and testing software program (e.g., when the program is started by a user). Beginning with step 904 in FIG. 24, each report from the list is processed by the data acquisition/processing device 104. Initially, at decision block 906, it is determined whether the particular report that is being processed requires a specific test result type or condition. If the particular report being processed does not require a specific test result type or condition, then, in step 912, the report is added to the subject (patient) information icon 804 in FIGS. 21 and 22. For example, referring to the screenshots of FIGS. 21 and 22, the Patient Information report 808, 808' is always generated by the measurement and testing software program, and displayed under the subject (patient) information icon 804. As explained above, an exemplary Patient Information report 808, 808' comprises background information regarding the patient, such as height, weight, home address, contact information, name of physician, etc. Because the Patient Information report 808, 808' contains general information about the subject or patient that is not specific to any particular test, there is no need to apply a filter to this report. Conversely, if it is determined in decision block 906 that the particular report being processed does require a specific test result type to be present or a condition to be satisfied, then, in step 908, the requisite specific test type(s) or condition(s) are checked (i.e., conditions such as the data range, etc.). For example, a data range condition may stipulate that a particular report may only be displayed when test results exist for a predetermined date range (e.g., from May 4th to May 11th). Advantageously, the use of conditions allows the measurement and testing software program to filter the reports that are displayed under subject (patient) information icon 804.

Now, several exemplary conditions that are checked by the measurement and testing software program will be explained. Initially, each report file informs the system 100 of what it wants or needs. This starts out with a list of test GUIDs (e.g., BESS assessment test) that are grouped into the following lists, any or all of which can be empty or contain values: (i) Must Have List; (ii) Must Not Have List; (iii) Can Have List. In the Must Have List, the report is shown only if all of test GUIDs contained in this list exist in the overall list of test results that the subject or patient has performed. For example, suppose the report file comprises the following lines of code:

list=report:: mustHaveTheseGuids( )
if (list is not empty)
then
    if (resultsTestGuids contains all values in list) then
        return true #this will indicate do show report else
        return false #this will indicate do not show report In the above example, if the file, entitled resultsTestGuids, contains all of the GUID values in the list, then the report will be shown. However, if the file, entitled resultsTestGuids, does not contain all of the GUID values in the list, then the report will not be shown. For example, for a particular report to be displayed, it may be required that results from both a Limits of Stability (LOS) test and a Forward Lunge test are available. In the Must Not Have List, the report is not shown if one or more of these test GUIDs contained in this list exist in the overall list of test results that the subject or patient has performed. For example, suppose the report file comprises the following lines of code:

list=report::mustNOThaveTheseGuids( )
if (list is not empty)
then
    if (resultsTestGuids contains any value in list)
    then
        return false #this will indicate do not show report In the above example, if the file, entitled resultsTestGuids, contains any of the GUID values in the list, then the report will not be shown. However, if the file, entitled resultsTestGuids, does not contain any of the GUID values in the list, then the report will be shown. For example, for a particular report to be displayed, it may be required that results for a Limits of Stability (LOS) test are not contained within the same session as results for a Forward Lunge test. In the Can Have List, the report is shown only if one or more of these Test GUIDs exist in the list of test results that the subject or patient has performed. For example, suppose the report file comprises the following lines of code:

list=report::canHaveTheseGuids( )
if (list is not empty)
then
    if (resultsTestGuids contains any values in list)
    then
        return true #this will indicate do show report else
        return false #this will indicate do not show report
            return true #no list of anything, the report is always shown In the above example, if the file, entitled resultsTestGuids, contains any of the GUID values in the list, then the report will be shown. However, if the file, entitled resultsTestGuids, does not contain any of the GUID values in the list, then the report will not be shown. If the file does not contain a list of anything, then the report is always shown (e.g., the Patient Information report). As one example, the results from a Limits of Stability (LOS) test could be combined with the results from a Standing Stability test in a single report. Considering the three exemplary conditions described above, the Must Not Have List trumps the other two conditions.

In addition, the measurement and testing software program preferably has the following additional flags that determine how the above lists (i.e., conditions) are used: (i) tests must be in the same session, and (ii) tests must be in the same day. If it is true that the tests must be in the same session, then the abovedescribed three filtering lists (i.e., filtering conditions) are applied only to groups of test results that occur within the same session (a collection of test results that were performed logically together). For example, suppose that the above three rules state that both BESS and LOS are required (i.e., must-haves), then the report is only shown if both the Balance Error Scoring System (BESS) and Limits of Stability (LOS) test results are available in the same session. If the BESS test was done in one session, and the LOS test in another session, then the report is not available. If it is true that the tests must be in the same day, then the abovedescribed three filtering lists are applied only to groups of test results that occur within the same calendar day—this implies same session, but can be separate sessions in the same day. For example, suppose that the above three rules state that both BESS and LOS are required (i.e., must-haves), then the report is only shown if both BESS and LOS results are available in the same day. If BESS was done on one day, and LOS on another day, then the report is not available. If neither the Same Session or Same Day flags are set, then the abovedescribed three filtering lists are used without regard to the session or calendar day grouping. That is, the entire list of tests performed by the patient is used when examining each condition (i.e., each of the three lists).

In another alternative embodiment, the reports could be filtered in accordance with numerical values that are contained within the test results themselves. In this embodiment, a particular report could be displayed only when a subject's score for a particular test exceeds a certain predetermined value (e.g., when a subject's score is 50 or greater). Also, one or more reports could require two or more sessions of test results to exist before being displayed (e.g., results from BESS tests performed in two or more sessions). In addition, in some embodiments, the conditions described above could be combined with another (e.g., a particular report could only be displayed if test results for both a BESS test and Tandem Walk test exist but not those for a mCTSIB test.

Referring back to FIG. 24, at decision block 910, it is determined whether the condition is satisfied (i.e., one of the conditions described above). If the condition is satisfied, then, in step 912, the report is added to the subject (patient) information icon 804 in FIGS. 21 and 22. However, if the condition is not satisfied, then the process proceeds to step 914, wherein it is determined if there are additional reports from the list to process. If there are not additional reports from the list to process, the process ends at step 918 (see FIG. 25). However, if there are additional reports from the list to process, the process proceeds to step 916, wherein the data acquisition/processing device 104 continues to the next report from the list. As shown in FIGS. 24 and 25, after step 916, the process reverts back to step 904 in which the next report from the list is processed. It is to be understood that the procedure illustrated in FIGS. 24 and 25 will continue in the manner described above until all of the reports from the list have been processed. Advantageously, as a result of the filtering process described above, the measurement and testing software program does not generate any empty global/progress reports (i.e., global/progress reports that do not contain any numerical test results).

According to still another aspect of the illustrative embodiment, referring to FIGS. 26-33, the data acquisition/data processing device 104 of the measurement and testing system 100 is configured and arranged to automatically filter the tests that are available in accordance with the type of measurement assembly or assemblies 102 that are connected to the data acquisition/data processing device 104. In general, according to this aspect of the illustrative embodiment, the data acquisition and processing device 104 is configured and arranged to (i) assemble a list of tests that are capable of being performed utilizing the at least one measurement assembly 102; (ii) determine, for each of the tests in the list, whether the execution of each particular test in the list requires the use of a specific measurement assembly and/or requires that a predetermined condition be satisfied (i.e., requires the use of a specific measurement assembly, or that a predetermined condition be satisfied, or both the use of a specific measurement assembly and that a predetermined condition be satisfied); (iii) when it is determined that the execution of the particular test in the list requires the use of a specific measurement assembly and/or requires that a predetermined condition be satisfied, determine whether the at least one measurement assembly 102 comprises the specific measurement assembly that is required and/or whether the predetermined condition has been satisfied; and (iv) when it is determined that the at least one measurement assembly is the specific measurement assembly that is required and/or the predetermined condition has been satisfied, add the test name or icon for the particular test to a listing of available test names or icons that are displayed on the at least one visual display device 130 so that a system user is able to select the particular test. Advantageously, the measurement and testing software program loaded on, and executed by the data acquisition and processing device 104 automatically determines the test protocols that are available based on the type of measurement assembly 102 connected to the system 100.

Figure 26:
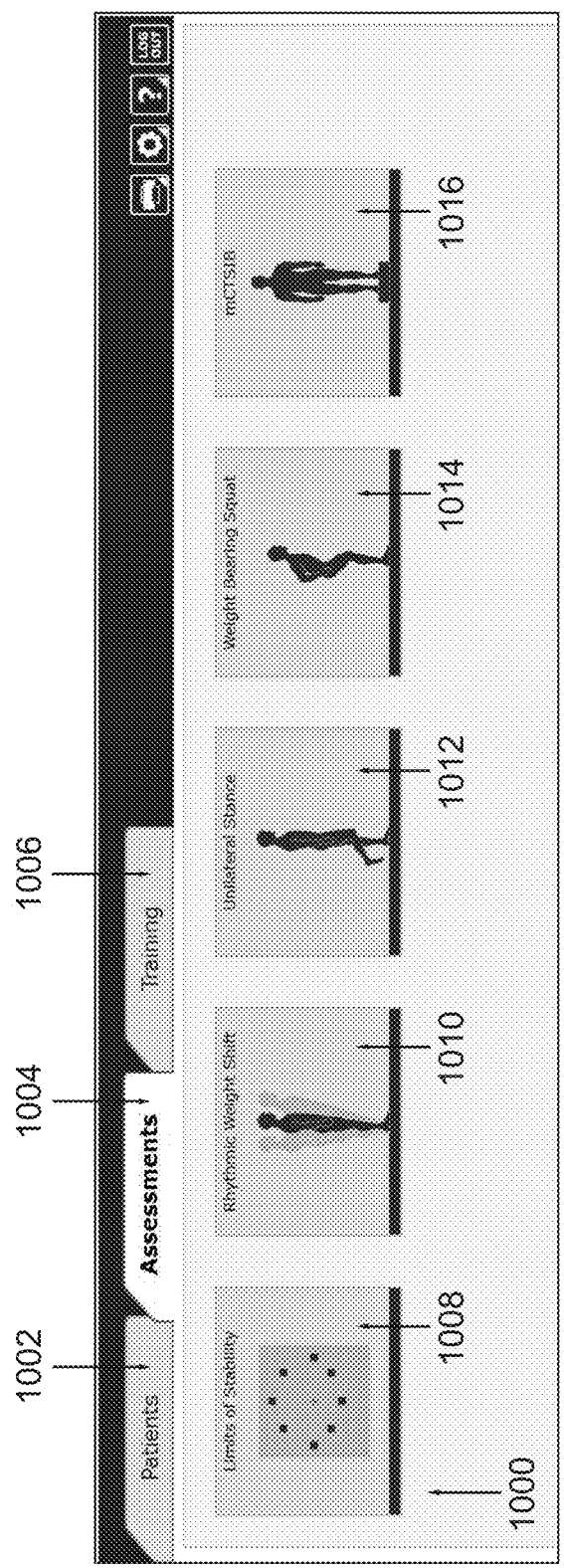
FIG. 26 is a partial screenshot displayed on the operator visual display device of the measurement and testing system illustrating a group of tests that are available when a first type of measurement assembly is connected to the data acquisition and processing device, according to an embodiment of the invention.

Initially, referring to FIG. 26, it can be seen that the data acquisition/data processing device 104 of the measurement and testing system 100 is configured and arranged to generate a screen image 1000 that includes a plurality of mode selection tabs 1002, 1004, and 1006. When a user selects the Assessments tab 1004, a plurality of test icons 1008-1016 are displayed on the visual display device 130. As shown in the screenshot of FIG. 26, these test icons include a first icon 1008 for a Limits of Stability (LOS) test, a second icon 1010 for a Rhythmic Weight Shift test, a third icon 1012 for a Unilateral Stance test, a fourth icon 1014 for a Weight Bearing Squat test, and a fifth icon 1016 for a mCTSIB test. In order to execute a particular test, a user merely selects the appropriate test icon (e.g., by clicking on one of the icons 1008-1016). In the illustrative embodiment, when a first type of measurement assembly 102 is connected to the data acquisition/data processing device 104, this group of tests is displayed. For example, the first type of measurement assembly 102 may comprise a dual force plate assembly having a particular footprint (e.g., a static dual force plate having a 18"×20" overall footprint). The test icons 1008-1016 in FIG. 26 represent the tests that are capable of being effectively performed using the first type of measurement assembly 102. The tests that are not capable of being performed using the first type of measurement assembly 102 are filtered out by the measurement and testing software program so they are not displayed on the visual display device 130, and thus, are not available for selection by a system user when the first type of measurement assembly 102 is connected.

It is to be understood that certain tests can only be effectively performed using certain measurement assemblies 102. For example, a particular test may require a measurement assembly 102 that has a minimum footprint size (i.e., dimensional area). Thus, if a measurement assembly 102 having a footprint size that is smaller than the minimum footprint size is the only one connected to the data acquisition/data processing device 104, the tests requiring the minimum footprint size would not be displayed on the visual display device 130. As another example, a particular test may require the measurement assembly to have dynamic functionality (e.g., the measurement assembly 102 comprises a force plate that is rotated, or translated, or both rotated and translated). Consequently, if a measurement assembly 102 which does not have the requisite dynamic functionality is the only one connected to the data acquisition/data processing device 104, the tests requiring the dynamic functionality would not be displayed on the visual display device 130.

Figure 27:
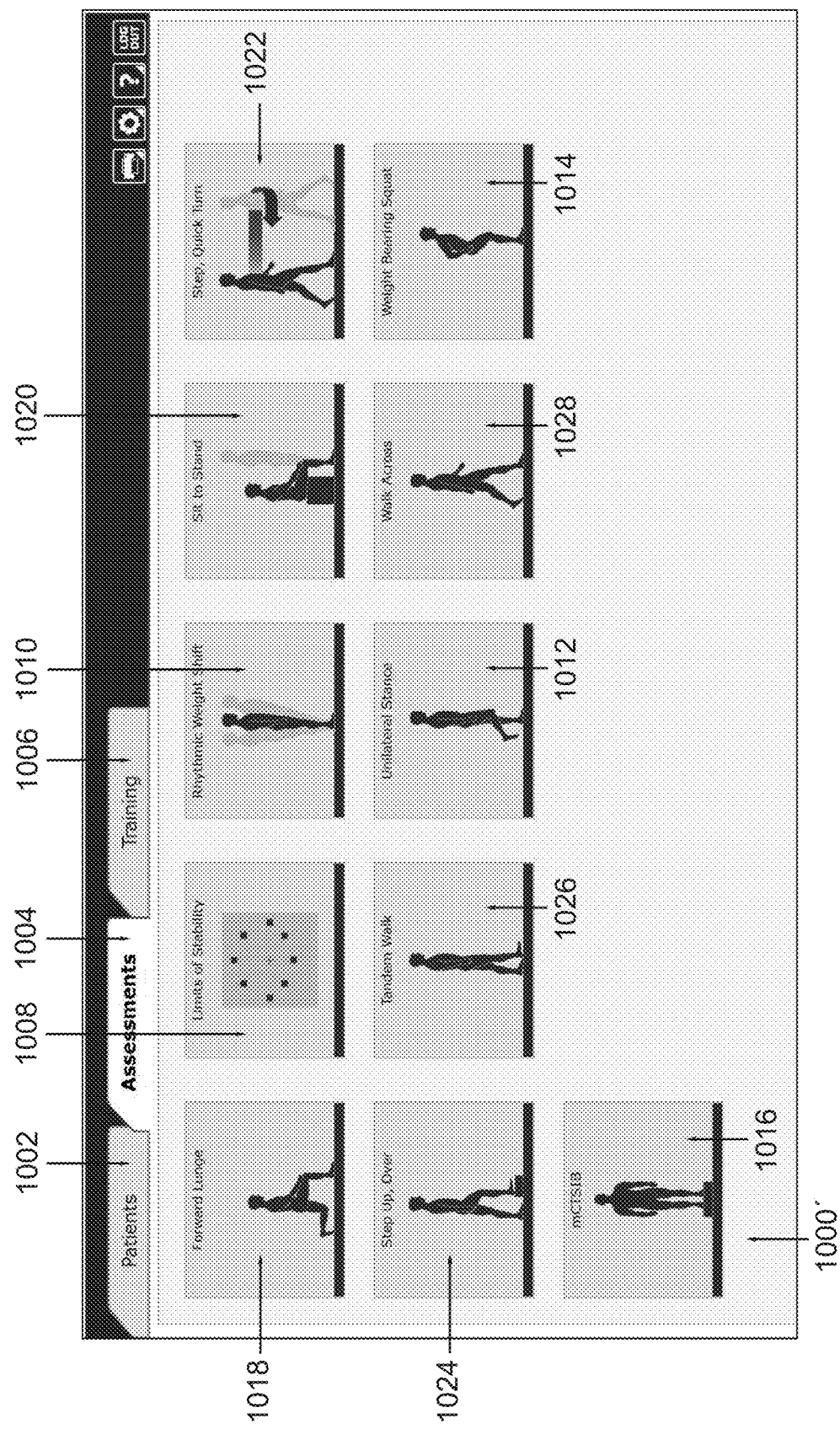
FIG. 27 is a partial screenshot displayed on the operator visual display device of the measurement and testing system illustrating a group of tests that are available when a second type of measurement assembly is connected to the data acquisition and processing device, according to an embodiment of the invention.

Another exemplary screenshot 1000' is depicted in FIG. 27. Similar to the screenshot 1000 illustrated in FIG. 26, the screenshot 1000' of FIG. 27 includes a plurality of mode selection tabs 1002, 1004, and 1006. However, when a user selects the Assessments tab 1004, a greater number of test icons 1008-1028 are displayed on the visual display device 130, as compared to that displayed in the screenshot of FIG. 26. As shown in the screenshot of FIG. 27, the test icons include an icon 1008 for a Limits of Stability (LOS) test, an icon 1010 for a Rhythmic Weight Shift test, an icon 1012 for a Unilateral Stance test, an icon 1014 for a Weight Bearing Squat test, an icon 1016 for a mCTSIB test, an icon 1018 for a Forward Lunge test, an icon 1020 for a Sit to Stand test, an icon 1022 for a Step, Quick Turn test, an icon 1024 for a Step Up, Over test, an icon 1026 for a Tandem Walk test, and an icon 1028 for a Walk Across test. As described above, in order to execute a particular test, a user merely selects the appropriate test icon (e.g., by clicking on one of the icons 1008-1028). In the illustrative embodiment, when a second type of measurement assembly 1402, 1404 (see FIGS. 36 and 37) is connected to the data acquisition/data processing device 104, this group of tests is displayed. For example, the second type of measurement assembly 1402, 1404 may comprise a dual force plate assembly having an overall footprint that is larger than the first type of measurement assembly (e.g., a static dual force plate having 20"×60"

overall footprint). The test icons 1008-1028 in FIG. 27 represent the tests that are capable of being effectively performed using the second type of measurement assembly 1402, 1404. The tests that are not capable of being performed using the second type of measurement assembly 1402, 1404 are filtered out by the measurement and testing software program so they are not displayed on the visual display device 130, and thus, are not available for selection by a system user when the second type of measurement assembly 1402, 1404 is connected.

Figure 28:
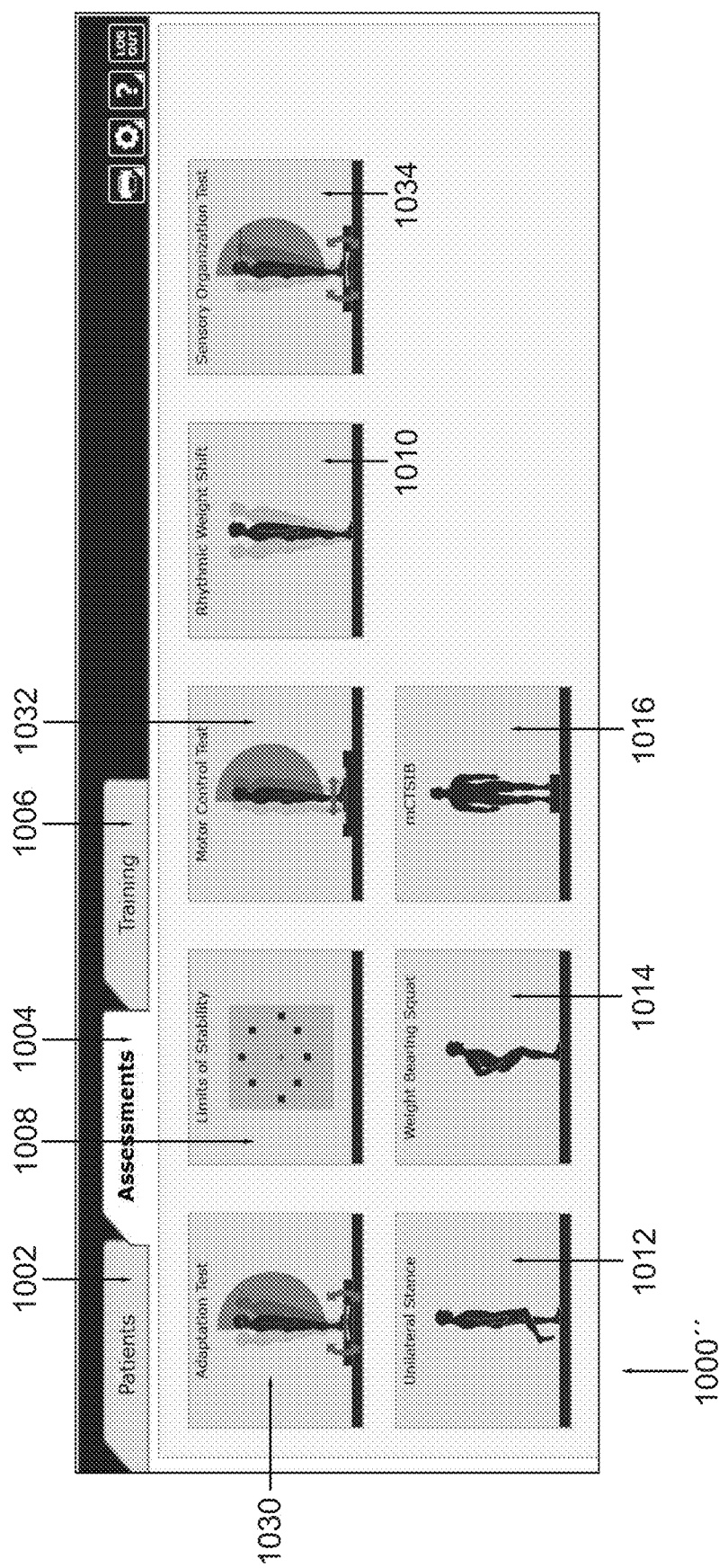
FIG. 28 is a partial screenshot displayed on the operator visual display device of the measurement and testing system illustrating a group of tests that are available when a third type of measurement assembly is connected to the data acquisition and processing device, according to an embodiment of the invention.

In FIG. 28, yet another exemplary screenshot 1000" is shown Like the screenshots 1000, 1000' illustrated in FIGS. 26 and 27, the screenshot 1000" of FIG. 28 includes a plurality of mode selection tabs 1002, 1004, and 1006. However, when a user selects the Assessments tab 1004, a different group of test icons 1008-1016 and 1030-1034 are displayed on the visual display device 130, as compared to that displayed in the screenshots of FIGS. 26 and 27. As shown in the screenshot of FIG. 28, the test icons include an icon 1008 for a Limits of Stability (LOS) test, an icon 1010 for a Rhythmic Weight Shift test, an icon 1012 for a Unilateral Stance test, an icon 1014 for a Weight Bearing Squat test, an icon 1016 for a mCTSIB test, an icon 1030 for an Adaption Test, an icon 1032 for a Motor Control Test, and an icon 1034 for a Sensory Organization Test (SOT). As explained above, in order to execute a particular test, a user merely selects the appropriate test icon (e.g., by clicking on one of the icons 1008-1016, 1030-1034). In the illustrative embodiment, when a third type of measurement assembly (e.g., a dynamic measurement assembly) is connected to the data acquisition/data processing device 104, this group of tests is displayed. For example, the third type of measurement assembly may comprise a dynamic force plate assembly, wherein a dual force plate is capable of being rotated, translated, or both rotated and translated while a subject or patient is disposed thereon. The dynamic force plate assembly may have a dual force plate that has a footprint similar to the first type of measurement assembly 102 (e.g., a dual force plate having a 18"×20" overall footprint). The test icons 1008-1016 and 1030-1034 in FIG. 28 represent the tests that are capable of being effectively performed using the third type of measurement assembly (i.e., the dynamic force measurement assembly). The tests that are not capable of being performed using the third type of measurement assembly are filtered out by the measurement and testing software program so they are not displayed on the visual display device 130, and thus, are not available for selection by a system user when the third type of measurement assembly is connected.

Figure 29:
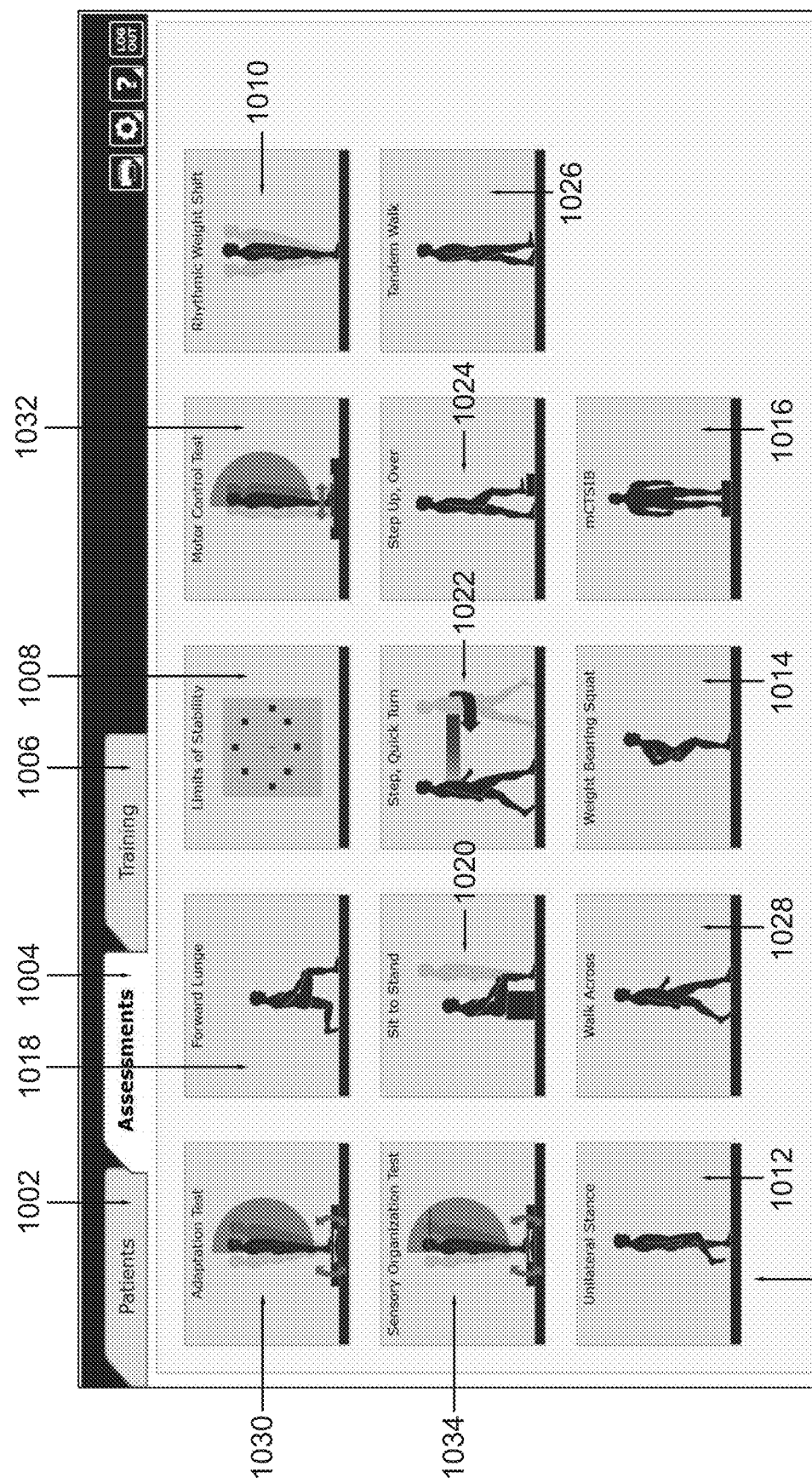
FIG. 29 is a partial screenshot displayed on the operator visual display device of the measurement and testing system illustrating a group of tests that are available when both the second and third types of measurement assemblies are connected to the data acquisition and processing device, according to an embodiment of the invention.
Figure 30:
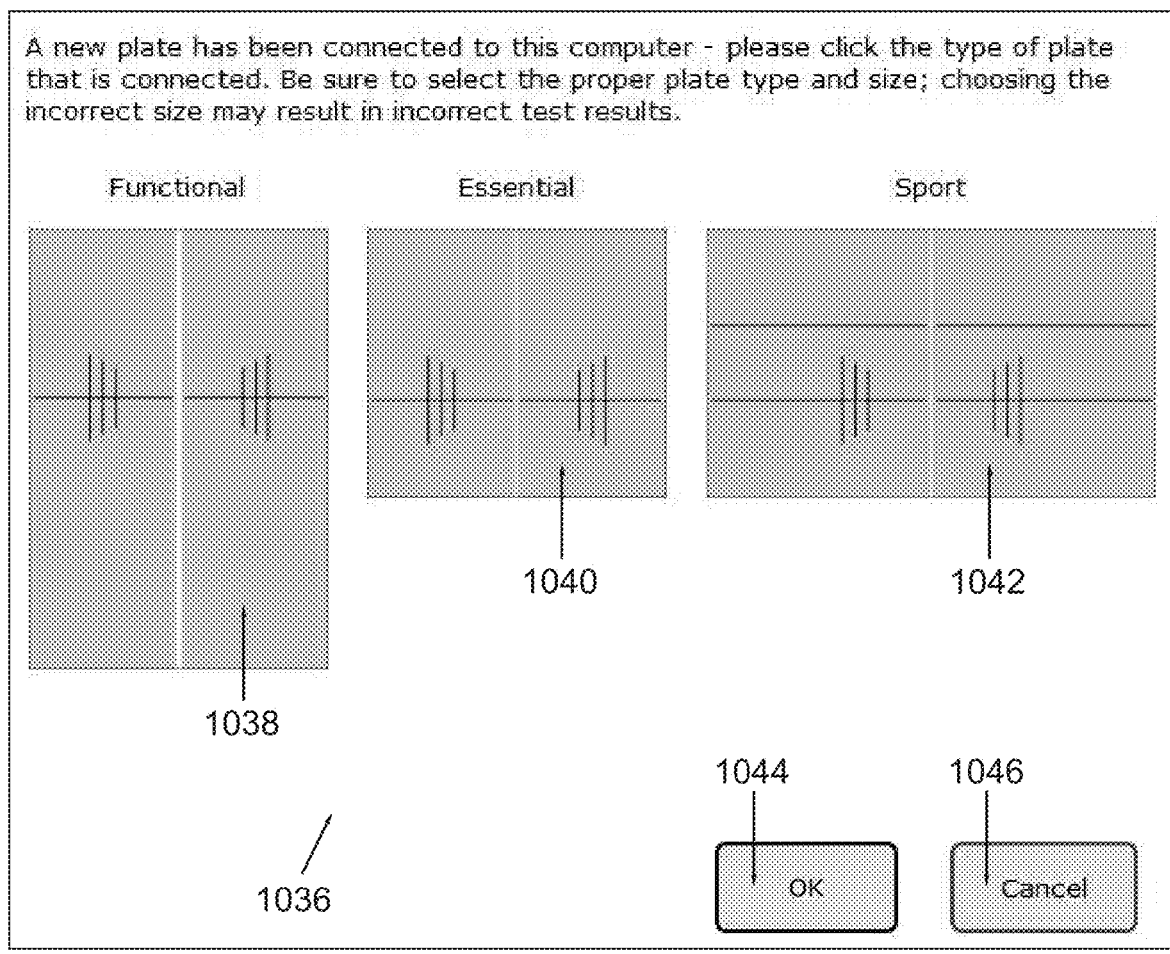
FIG. 30 is a partial screenshot displayed on the operator visual display device of the measurement and testing system illustrating a pop-up window that allows a system user to manually select the type of measurement assembly is connected to the data acquisition and processing device, according to an embodiment of the invention.
Figure 31:
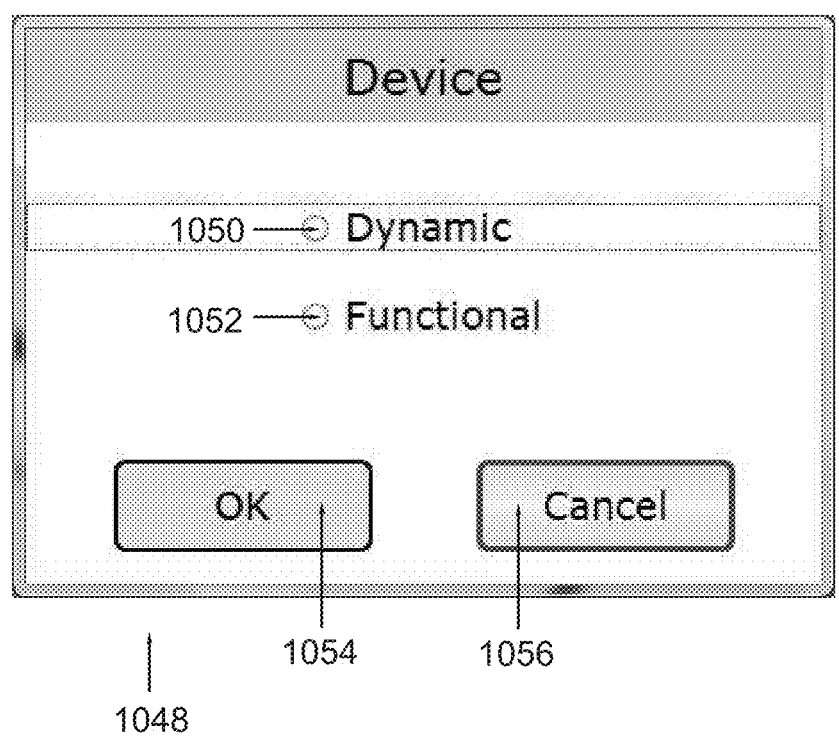
FIG. 31 is a partial screenshot displayed on the operator visual display device of the measurement and testing system illustrating a pop-up window that allows a system user to manually select the type of measurement assembly that he or she wants to utilize for performing a particular test, according to an embodiment of the invention.

With reference to FIG. 29, still another exemplary screenshot 1000''' is illustrated. Like the screenshots 1000, 1000', 1000" shown in FIGS. 26, 27, and 28, respectively, the screenshot 1000' of FIG. 29 includes a plurality of mode selection tabs 1002, 1004, and 1006. Although, when a user selects the Assessments tab 1004, a larger group of test icons 1008-1034 are displayed on the visual display device 130, as compared to that displayed in the screenshots of FIGS. 26-28. As shown in the screenshot of FIG. 29, the test icons include an icon 1008 for a Limits of Stability (LOS) test, an icon 1010 for a Rhythmic Weight Shift test, an icon 1012 for a Unilateral Stance test, an icon 1014 for a Weight Bearing Squat test, an icon 1016 for a mCTSIB test, an icon 1018 for a Forward Lunge test, an icon 1020 for a Sit to Stand test, an icon 1022 for a Step, Quick Turn test, an icon 1024 for a Step Up, Over test, an icon 1026 for a Tandem Walk test, and an icon 1028 for a Walk Across test, an icon 1030 for an Adaption Test, an icon 1032 for a Motor Control Test, and an icon 1034 for a Sensory Organization Test (SOT). As described above, in order to execute a particular test, a user merely selects the appropriate test icon (e.g., by clicking on one of the icons 1008-1034). In the illustrative embodiment, when both the second and third type of measurement assembly are connected to the data acquisition/data processing device 104, this group of tests is displayed. In other words, the test icons 1008-1034 depicted in the screenshot of FIG. 29 are representative of the combined set of tests that are available when both the static dual force plate with a 20"×60" overall footprint, and the dynamic force plate assembly, are both operatively coupled to the data acquisition/data processing device 104. The test icons 1008-1034 in FIG. 29 represent the tests that are capable of being effectively performed using at least one of the second and third types of measurement assemblies (i.e., at least one of the 20"×60" static dual force plate 1402, 1404 and the dynamic force measurement assembly). The tests that are not capable of being performed using one of these two types of measurement assemblies are filtered out by the measurement and testing software program so they are not displayed on the visual display device 130, and thus, are not available for selection by a system user when these measurement assemblies are connected.

When a measurement assembly (e.g., 102) is initially connected to the data acquisition/data processing device 104, the data acquisition/data processing device 104 reads the serial number from the firmware installed on the measurement assembly 102. If the serial number from the measurement assembly 102 is recognized by the data acquisition/data processing device 104, the measurement and testing software program automatically filters the tests that are displayed on the visual display device 130 in accordance with the type of device that is connected (e.g., if a particular serial number is already is associated with a 20"×60" static dual force plate, and this is the only plate in the system 100, then the measurement and testing software program automatically filters out all of the tests that cannot be performed on this plate). However, if the serial number from the measurement assembly 102 is not recognized by the data acquisition/data processing device 104 (e.g., because this is the first time that the plate has ever been connected to the data acquisition/data processing device 104), the data acquisition/data processing device 104 generates the pop-up window 1036 illustrated in FIG. 30. The pop-up window 1036 prompts the system user to manually select the type of measurement assembly 102 that is connected to the data acquisition/data processing device 104 by clicking on the appropriate one of the plate icons 1038, 1040, or 1042, and then, by pressing the "OK" button 1044 to complete his or her selection. Alternatively, if the user inadvertently selected the incorrect icon 1038, 1040, or 1042, he or she can always revise the selection by pressing the "Cancel" button 1046. Once the user manually selects the type of measurement assembly 102 that is connected to the data acquisition/data processing device 104 using the pop-up window 1036, the data acquisition/data processing device 104 equates the serial number of the connected device to the type of measurement assembly 102 that is operatively coupled to the data acquisition/data processing device 104 (e.g., Ser. No. 67899882 is a 18"×20" Essential force plate assembly because a user selected the Essential force plate icon 1040 in the pop-up window 1036). Once the serial number of the connected device has been equated to a particular type of measurement assembly 102, the pop-up window 1036 will not be subsequently displayed to the system user. Rather, after reading the recognized serial number from the firmware installed on the measurement assembly 102, the measurement and testing software program automatically filters the tests that are available for the connected device.

In another embodiment of the invention, rather than prompting the user to select the type of a newly connected device by displaying the pop-up window 1036, the data acquisition/data processing device 104 is specially programmed to automatically determine the type of the device by reading the force plate dimensional data from the firmware installed on the measurement assembly 102 (e.g., an 18"×20" footprint of the force plate assembly is embedded in the firmware). In this alternative embodiment, after retrieving the dimensional data from the firmware of the plate, the data acquisition/data processing device 104 is further configured to equate the dimensional data with a particular plate type (e.g., the data acquisition/data processing device 104 references tabular data that equates this dimensional data with an Essential-type force plate). Thus, in this embodiment, it is not necessary for the user to manually identify the type of plate that has been connected to the data acquisition/data processing device 104 when it is first utilized in the measurement and testing system 100.

Whenever two or more measurement assemblies 102 are connected to the data acquisition/data processing device 104, and a particular test is capable of being performed on each of these measurement assemblies 102, a user is automatically prompted to select which measurement assembly 102 is to be used for the particular test before the test is started. Specifically, the data acquisition/data processing device 104 is configured and arranged to generate the pop-up window 1048 illustrated in FIG. 31, which requires a user to select the type of device (i.e., force plate) that he or she wishes to use for the test. Initially, the user selects the radio button that is next to the desired device (e.g., radio button 1050 for a Dynamic force plate assembly with a displaceable force plate or radio button 1052 for a Functional static force plate with a 20"×60" overall footprint). After selecting the appropriate radio button 1050, 1052, the user then presses the "OK" button 1054 to complete his or her selection. Alternatively, if the user inadvertently selected the incorrect radio button 1050 or 1052, he or she can always revise the selection by pressing the "Cancel" button 1056. Once the user has selected the type of device that he or she wishes to utilize for performing the test, the user can then proceed with performing the desired test.

Figure 32:
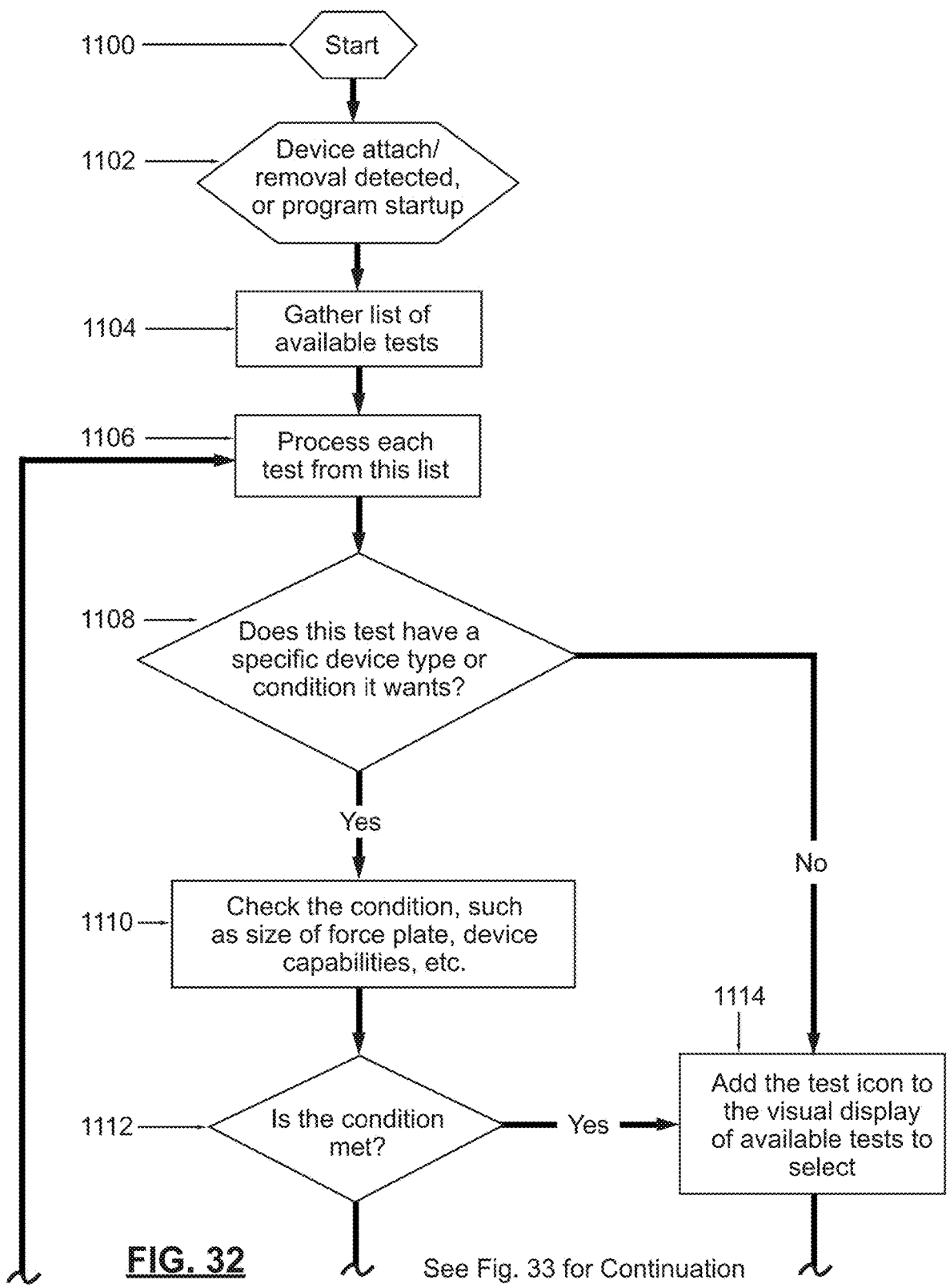
FIG. 32 is a partial flowchart illustrating a manner in which the availability of tests are determined based on the type of measurement assembly that is connected to the data acquisition and processing device, according to an embodiment of the invention.
Figure 33:
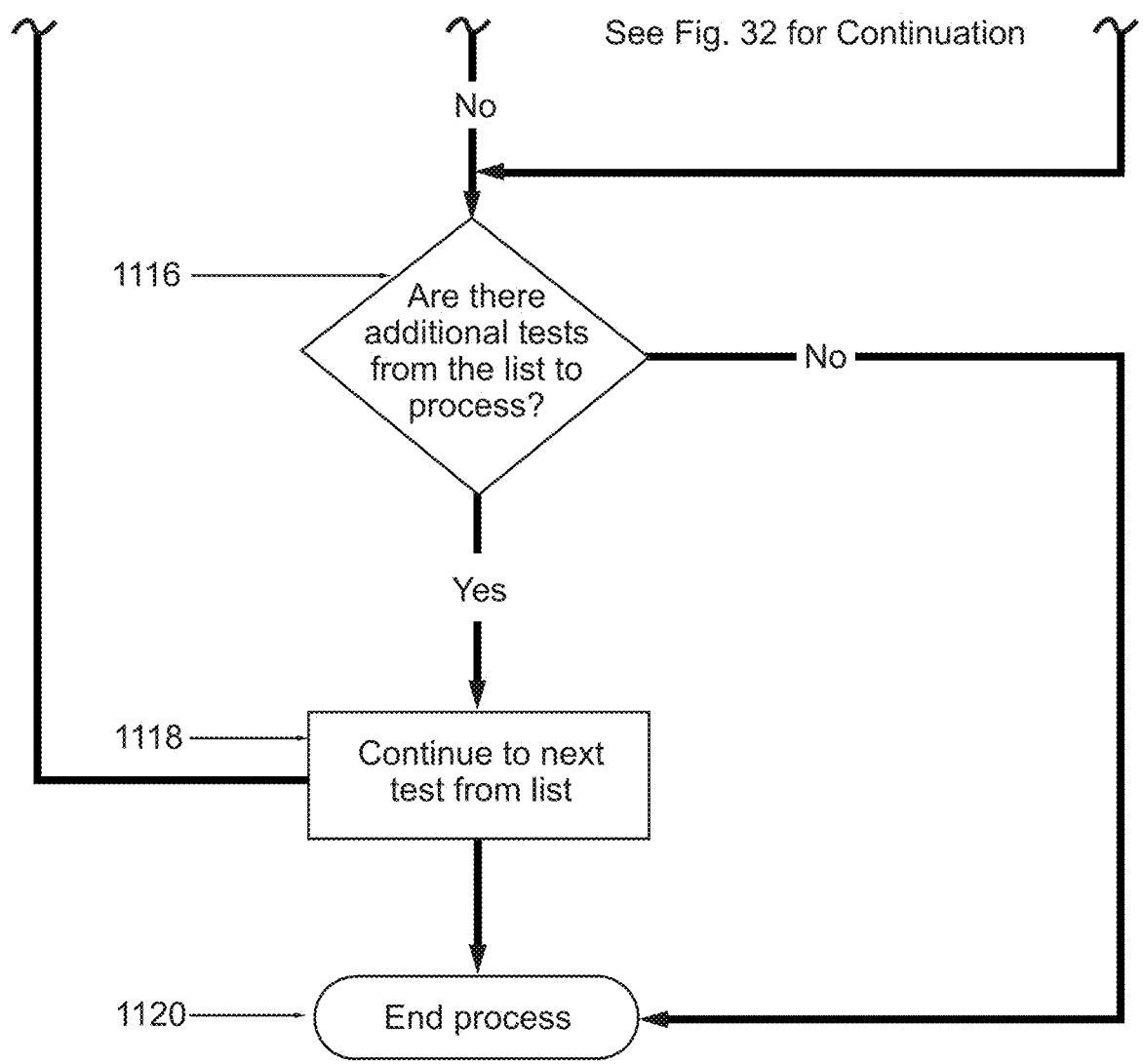
FIG. 33 is a continuation of the flowchart of FIG. 32, which illustrates additional steps of the procedure by which the availability of tests are determined based on the type of measurement assembly that is connected to the data acquisition and processing device, according to an embodiment of the invention.

In accordance with this aspect of the illustrative embodiment, a flowchart illustrating the functionality of the device test filter feature of the measurement and testing system 100 is set forth in FIGS. 32 and 33. All of the steps described below with reference to the flowcharts of FIGS. 32 and 33 are carried out by the data acquisition/processing device 104. Referring initially to FIG. 32, the procedure commences at 1100, and in step 1102, device (i.e., measurement assembly 102) attachment or removal is detected during the startup of the measurement and testing software program. That is, the data acquisition/processing device 104 reads the serial number of the device (e.g., a known or recognized measurement assembly 102) that is connected from the firmware of the device. Next, in step 1104, a list of the available tests are assembled by the data acquisition/processing device 104 (e.g., by reading a database list or a list of test files). Beginning with step 1106 in FIG. 32, each test from the list is processed by the data acquisition/processing device 104. Initially, at decision block 1108, it is determined whether the particular test that is being processed requires a specific type of device (i.e., type of measurement assembly 102) and/or whether it requires a certain condition to be satisfied. If the particular test that is being processed does not require a specific type of device or a condition to be satisfied, then, in step 1114, the test icon is added to the visual display of available tests that the user may select (e.g., as illustrated under the Assessments tab 1004 in FIGS. 26-29). For example, referring to the screenshots of FIGS. 26-29, the Limits of Stability (LOS) test, the Rhythmic Weight Shift test, the Unilateral Stance test, and the Weight Bearing Squat test are always available regardless of the type of device that is connected to the data acquisition/processing device 104, and thus, are always displayed under the Assessments tab 1004 in FIGS. 26-29. As such, these tests do not require any type of filtering. Conversely, if it is determined in decision block 1108 that the particular test being processed does require a specific device type or a condition to be satisfied, then, in step 1110, the requisite device type is evaluated or the requisite condition(s) is checked (i.e., conditions such as the size of the force plate, device capabilities, etc.). For example, a particular test may require a force plate with a minimum footprint (i.e., a minimum plate surface area) so that the subject or patient has adequate room to perform the test protocol (e.g., Forward Lunge test or Step Up, Over test). As another example, a certain test may require that the device is capable of displacing the force plate surface with the patient or subject disposed thereon while the test is being executed (e.g., Adaption Test, Motor Control Test, or Sensory Organization Test (SOT)). Advantageously, the use of conditions allows the measurement and testing software program to automatically filter the tests that cannot be effectively performed with the device or devices (i.e., measurement assembly or assemblies 102) that are connected to the data acquisition/processing device 104.

Referring again to the flowchart in FIG. 32, at decision block 1112, it is determined whether the condition is satisfied (e.g., one of the exemplary conditions described above). If the condition is satisfied, then, in step 1114, the test icon is added to the visual display of available tests that the user may select (e.g., as illustrated under the Assessments tab 1004 in FIGS. 26-29). However, if the condition is not satisfied, then the process proceeds to step 1116, wherein it is determined if there are additional tests from the list to process. If there are not additional tests from the list to process, the process ends at step 1120. However, if there are additional tests from the list to process, the process proceeds to step 1118, wherein the data acquisition/processing device 104 continues to the next test from the list. As shown in FIGS. 32 and 33, after step 1118, the process reverts back to step 1106 in which the next test from the list is processed. It is to be understood that the procedure illustrated in FIGS. 32 and 33 will continue in the manner described above until all of the tests from the list have been processed. Advantageously, as a result of the filtering process described above, the measurement and testing software program only permits a system user to select tests that can be effectively performed with the type of device (i.e., measurement assembly 102) that is connected to the data acquisition/processing device 104 (all other tests are filtered out by the abovedescribed process). Thus, inaccurate test results resulting from the use of an improper device are thereby automatically prevented by the measurement and testing system 100.

Figure 34:
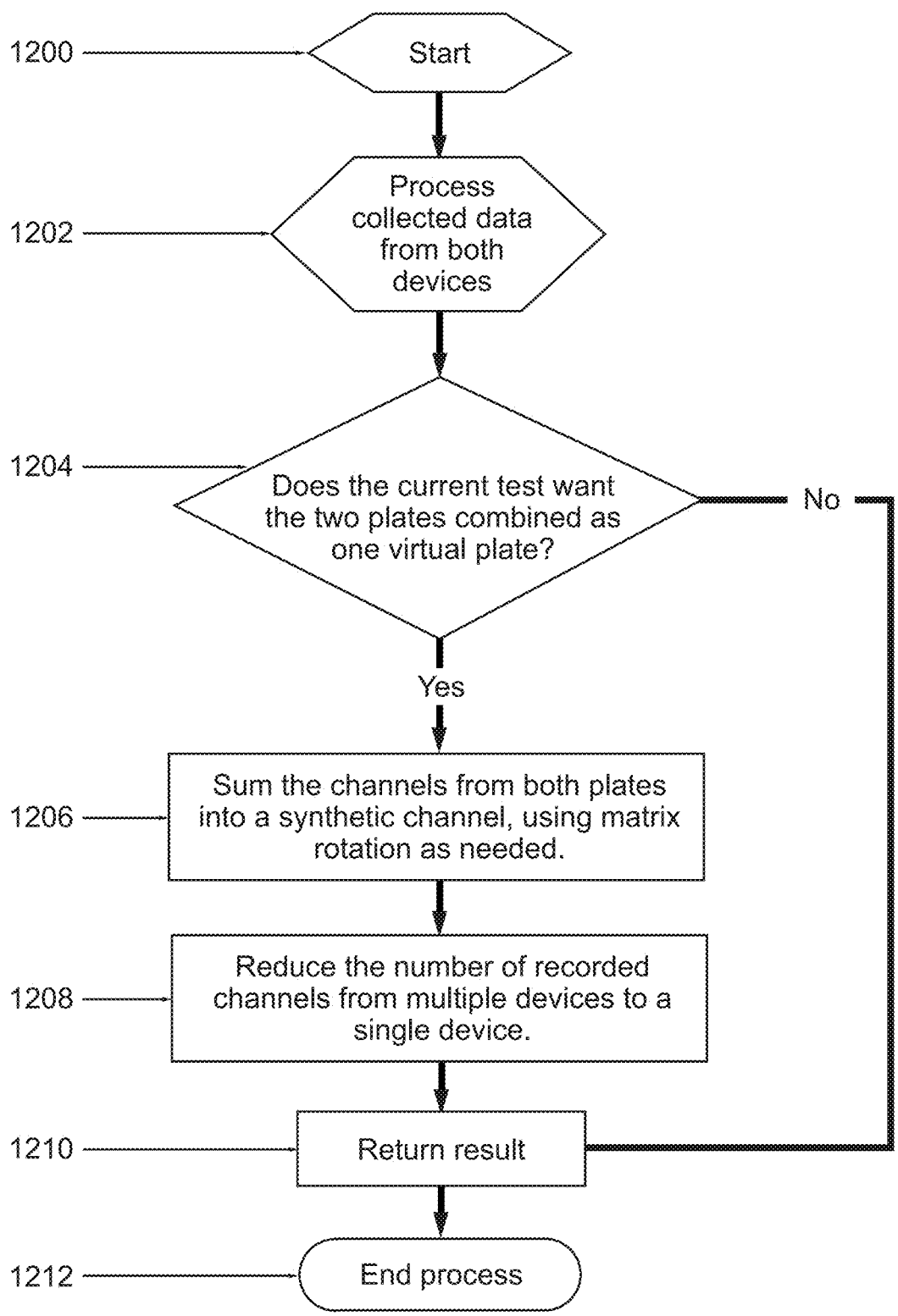
FIG. 34 is a flowchart illustrating the procedure by which output data from two measurement assemblies is combined by the data acquisition and processing device, according to an embodiment of the invention.
Figure 35:
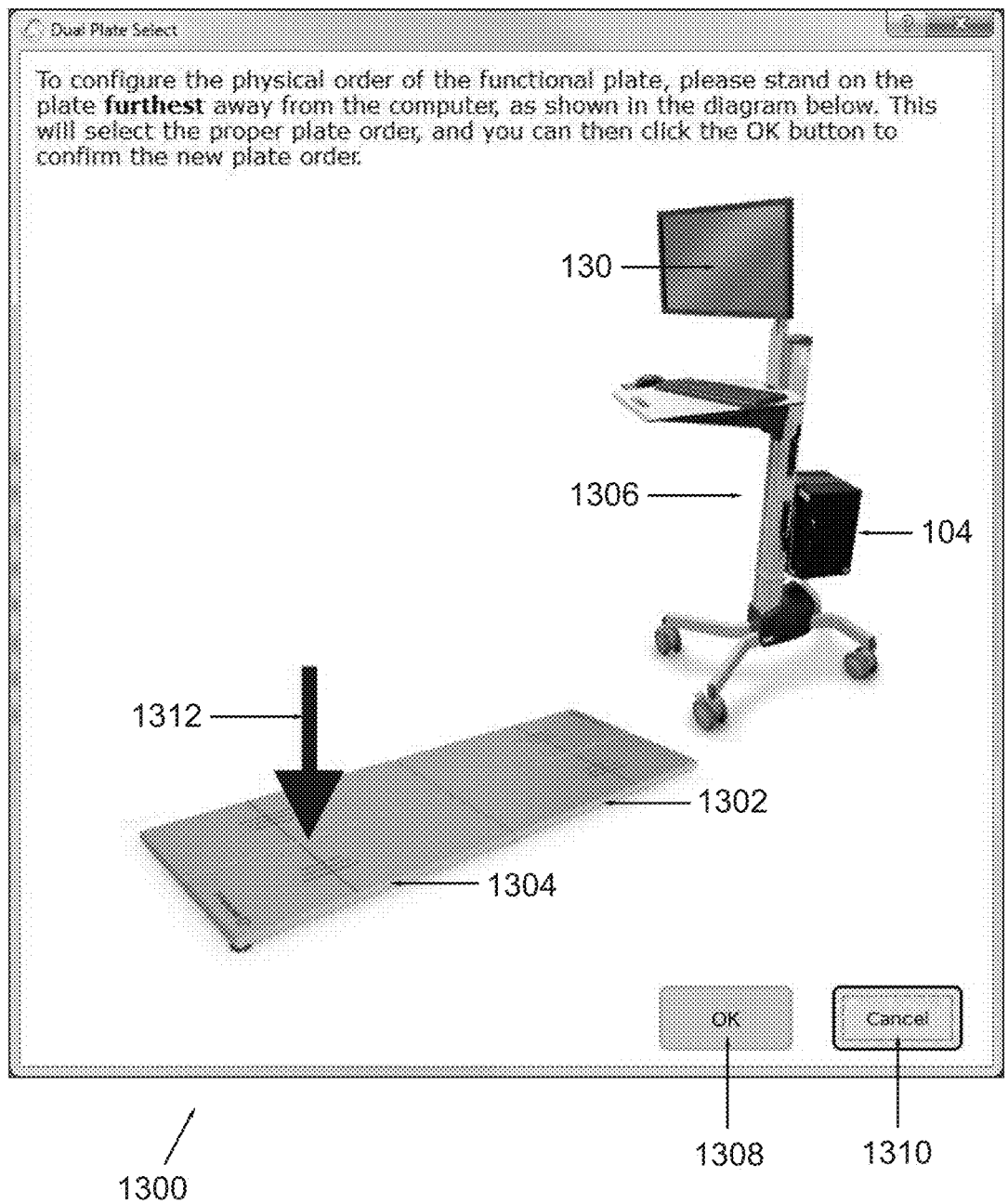
FIG. 35 is a partial screenshot displayed on the operator visual display device of the measurement and testing system illustrating a pop-up window that is used to determine the arrangement of a plurality of measurement assemblies that are connected to the data acquisition and processing device, according to an embodiment of the invention.
Figure 36:
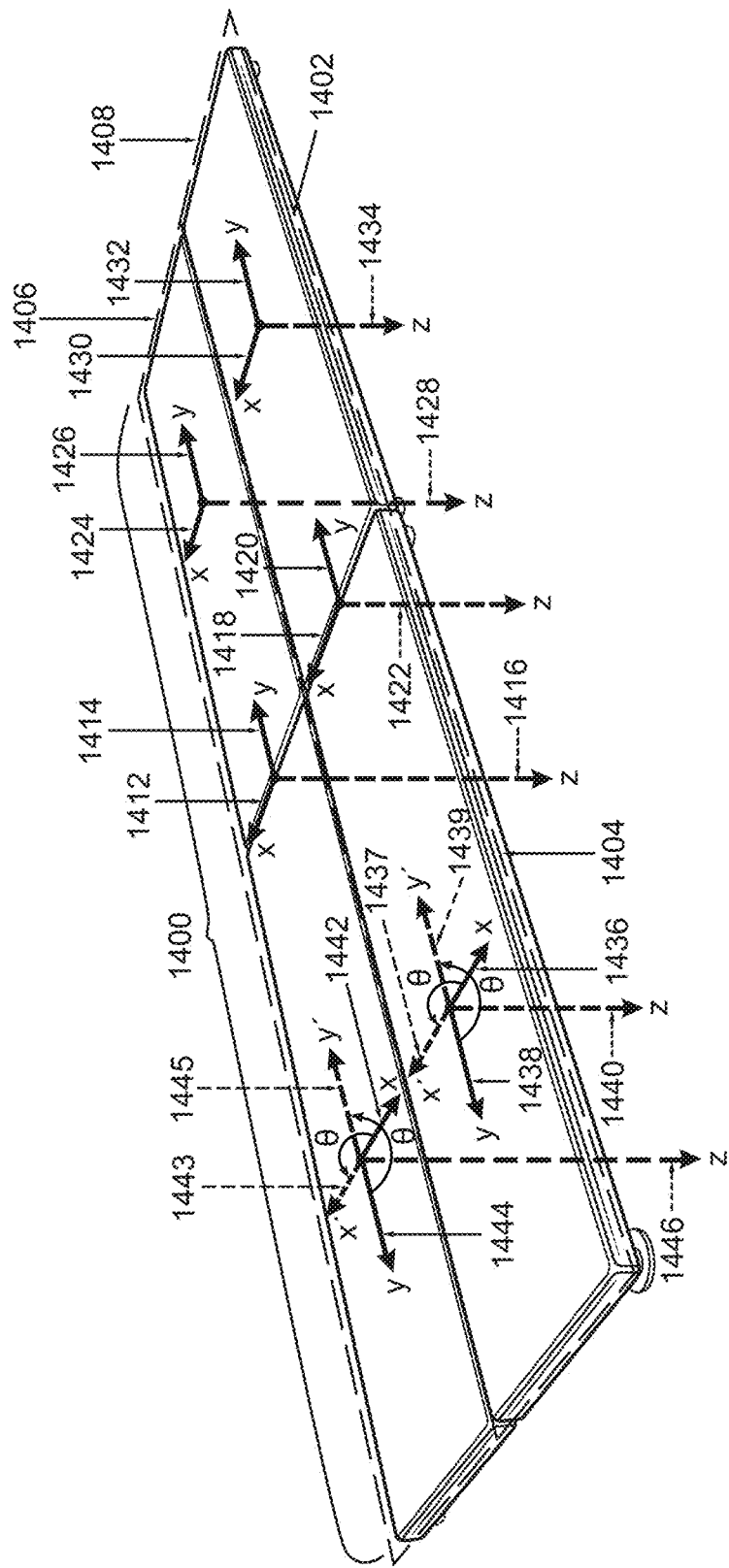
FIG. 36 is a perspective view of a plurality of measurement assemblies used in the measurement and testing system, according to an embodiment of the invention, wherein the measurement assemblies are combined as a single virtual measurement assembly with two measurement surfaces, and wherein a plurality of local and absolute coordinate axes are superimposed on each of the two measurement surfaces.
Figure 37:
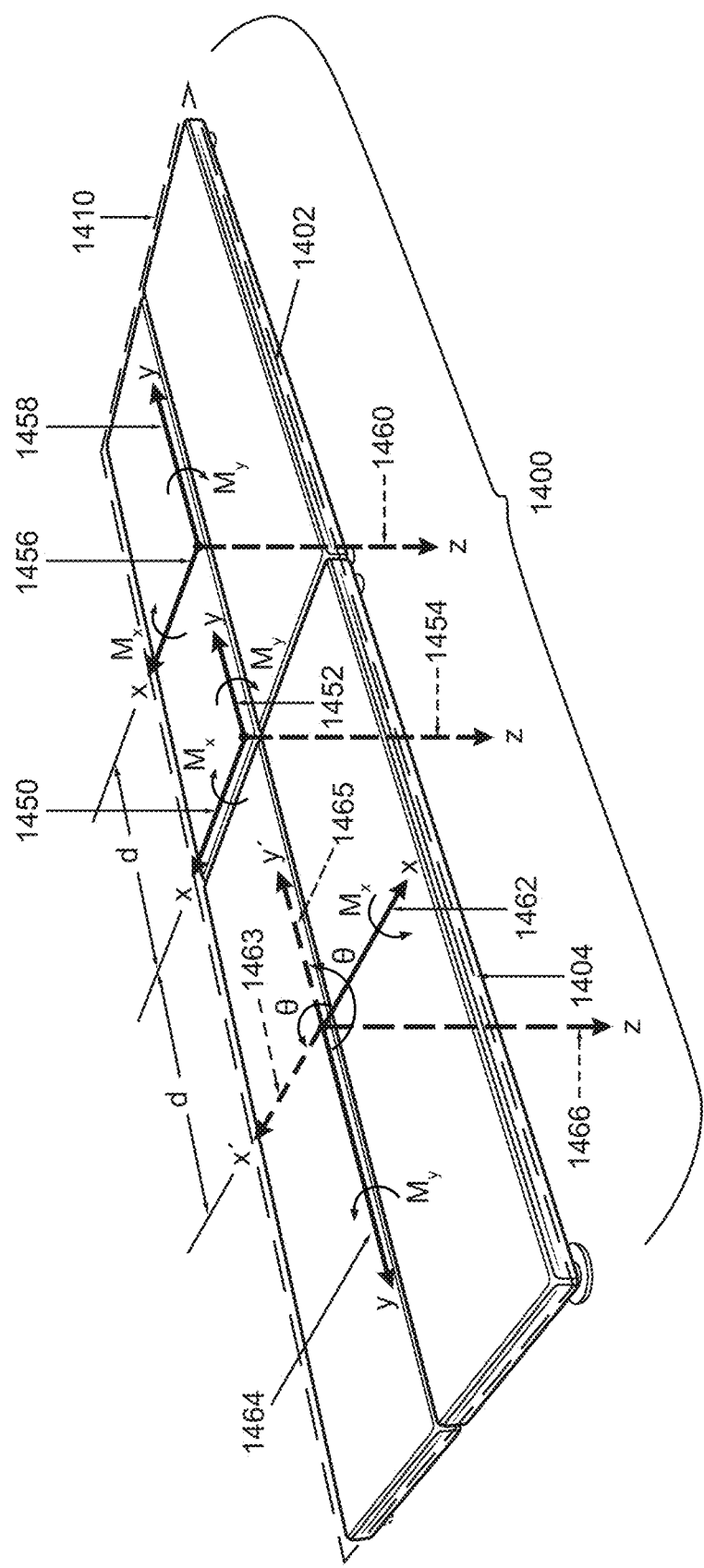
FIG. 37 is a perspective view of a plurality of measurement assemblies used in the measurement and testing system, according to an embodiment of the invention, wherein the measurement assemblies are combined as a single virtual measurement assembly with a single measurement surface, and wherein a plurality of local and absolute coordinate axes are superimposed on the single measurement surface.

According to yet another aspect of the illustrative embodiment, referring to FIGS. 34-37, the data acquisition/data processing device 104 is configured and arranged to mathematically combine the output for a plurality of measurement assemblies 1402, 1404—see FIGS. 36 and 37 (e.g., for a plurality of force plates) so as to create a virtual measurement assembly (e.g., a virtual force plate). Also, the data acquisition/data processing device 104 is configured and arranged to automatically correct the local coordinate system of one of the measurement assemblies 102 (e.g., one of the plurality of force plates) in order to account for the actual orientation of the measurement assembly 102 (e.g., force plate) relative to the other measurement assembly 102 (e.g., force plate). For example, in one particular arrangement, two measurement assemblies 102 (e.g., force plates) are placed in an end-to-end arrangement, wherein one of the two force plates is rotated 180 degrees relative to the other of the two force plates.

In accordance with this aspect of the illustrative embodiment, a flowchart illustrating the functionality of the virtual measurement assembly feature of the measurement and testing system 100 is set forth in FIG. 34. All of the steps described below with reference to the flowchart of FIG. 34 are carried out by the data acquisition/processing device 104. Referring to FIG. 34, the procedure commences at 1200, and in step 1202, collected data from a plurality of measurement assemblies or devices 102 (e.g., a plurality of force plates) is processed by the data acquisition/processing device 104. In one exemplary embodiment, two measurement assemblies 102 (e.g., force plates) are used to collect data from a subject or patient disposed thereon. In this embodiment, after the data acquisition/data processing device 104 receives a plurality of voltage signals (i.e., a plurality of channels of data) from the two measurement assemblies 102, it initially transforms the signals into output force and moment components by multiplying the voltage signals by a calibration matrix. For example, the voltage output signals received from the first force plate assembly are transformed into the vertical force component $F_{ZL1}$ exerted on the left plate of the assembly by the left foot of the subject, the vertical force component $F_{ZR1}$ exerted on the right plate of the assembly by the right foot of the subject, the moment component about the x axis $M_{XL1}$ exerted on the left plate of the assembly by the left foot of the subject, the moment component about the x axis $M_{XR1}$ exerted on the right plate of the assembly by the right foot of the subject, the moment component about the y axis $M_{YL1}$ exerted on the left plate of the assembly by the left foot of the subject, and the moment component about the y axis $M_{YR1}$ exerted on the right plate of the assembly by the right foot of the subject. Similarly, the voltage output signals received from the second force plate assembly are transformed into the vertical force component $F_{ZL2}$ exerted on the left plate of the assembly by the left foot of the subject, the vertical force component $F_{ZR2}$ exerted on the right plate of the assembly by the right foot of the subject, the moment component about the x axis $M_{XL2}$ exerted on the left plate of the assembly by the left foot of the subject, the moment component about the x axis $M_{XR2}$ exerted on the right plate of the assembly by the right foot of the subject, the moment component about the y axis $M_{YL2}$ exerted on the left plate of the assembly by the left foot of the subject, and the moment component about the y axis $M_{YR2}$ exerted on the right plate of the assembly by the right foot of the subject.

Next, at decision block 1204, it is determined whether the current subject or patient test wants or requires the two measurement assemblies 102 (e.g., force plates) to be combined as one virtual measurement assembly (e.g., one virtual force plate). If the particular test that is being performed does not want or require the two measurement assemblies 102 (e.g., force plates) to be combined as one virtual measurement assembly, the resultant separate force and moment components ($F_{ZL1}$, $F_{ZR1}$, $M_{XL1}$, $M_{XR1}$, $M_{YL1}$, $M_{YR1}$, $F_{ZL2}$, $F_{ZR2}$, $M_{XL2}$, $M_{XR2}$, $M_{YL2}$, $M_{YR2}$) are returned in step 1210. It is noted that, prior to returning the final computed result in step 1210, the separate force and moment components ($F_{ZL2}$, $F_{ZR2}$, $M_{XL2}$, $M_{XR2}$, $M_{YL2}$, $M_{YR2}$) for the second, rotated measurement assembly 102 (e.g., second force plate) are corrected in order to account for the actual orientation of the measurement assembly 102 (e.g., force plate) relative to the other measurement assembly 102 (e.g., force plate), as described hereinafter.

Conversely, if it is determined in decision block 1204 that the particular test that is being performed does want or requires the two measurement assemblies 1402, 1404 (e.g., force plates) to be combined as one virtual measurement assembly (e.g., one virtual force plate), the output signals (i.e., channels) are summed from both of the measurement assemblies 1402, 1404 (e.g., force plates) into a synthetic channel in step 1206, using matrix rotation to correct for the actual orientation of the second, rotated measurement assembly 1404 (e.g., force plate).

Initially, with reference to FIG. 36, the corrections that are performed for the second, rotated force plate 1404 will be explained. As shown in FIG. 36, two force plates 1402, 1404 are arranged end-to-end so as to form one overall force measurement assembly 1400 (or one virtual force plate 1400). The first force plate 1402, which is typically the force plate disposed closest to the data acquisition/processing device 104 and the operator visual display device 130, is disposed in a standard, non-rotated position. However, the second force plate 1404, which is typically the force plate disposed furthest from the data acquisition/processing device 104 and the operator visual display device 130, is disposed in a non-standard, rotated position (i.e., the second force plate 1404 is rotated 180 degrees relative to the first force plate 1402). As a result of the rotated orientation of the second force plate 1404, the left and right vertical force components $F_{ZL2}$, $F_{ZR2}$ must be swapped, the left and right moment components about the x axis $M_{XL2}$, $M_{XR2}$ must be swapped, and the left and right moment components about the y axis $M_{YL2}$, $M_{YR2}$ must be swapped. Also, in order to account for the 180 degree rotation of the second force plate 1404, the sign of the left and right moment components about the x axis $M_{XL2}$, $M_{XR2}$ must be flipped (e.g., −1 becomes +1), and the sign of the left and right moment components about the y axis $M_{YL2}$, $M_{YR2}$ must be flipped (e.g., −1 becomes +1). This sign change in the moment components $M_{XL2}$, $M_{XR2}$, $M_{YL2}$, $M_{YR2}$ for the second force plate 1404 can be generally explained with reference to the following rotation matrix:

$$R = \begin{bmatrix} \cos\theta & -\sin\theta \\ \sin\theta & \cos\theta \end{bmatrix} \quad (1)$$

In equation (1), when the angle θ is equal to 180 degrees, then the rotation matrix R is equal to:

$$R = \begin{bmatrix} -1 & 0 \\ 0 & -1 \end{bmatrix} \quad (2)$$

Thus, when the original values of the moment components $M_{XL2}$, $M_{XR2}$, $M_{YL2}$, $M_{YR2}$ are multiplied by a similar rotation matrix, wherein angle θ is equal to 180 degrees, the sign of the moment component values must be flipped.

Now, the manner in which the output signals from the individual force plates 1402, 1404 are summed in order to obtain the overall output values for the single virtual force plate 1400 with left and right measurement surfaces 1406, 1408 will be described (see FIG. 36). As illustrated in FIG. 36, the origin of the absolute coordinates axes 1412, 1414, 1416 for the left measurement surface 1406 is disposed between the two force plates 1402, 1404, and is centered in a lateral direction on the virtual left plate surface. Similarly, as also illustrated in FIG. 36, the origin of the absolute coordinates axes 1418, 1420, 1422 for the right measurement surface 1408 is disposed between the two force plates 1402, 1404, and is centered in a lateral direction on the virtual right plate surface. Initially, the overall left and right vertical force components $F_{ZL\_VP}$, $F_{ZR\_VP}$ for the virtual force plate 1400 are obtained as follows:

$$F_{ZL\_VP} = F_{ZL1} + F_{ZR1} \quad (3)$$

$$F_{ZR\_VP} = F_{ZR1} + F_{ZL2} \quad (4)$$

where:

$F_{ZL1}$: vertical force component exerted on the surface of the first force plate by the left foot of the subject;

$F_{ZR1}$: vertical force component exerted on the surface of the first force plate by the right foot of the subject;

$F_{ZL2}$: vertical force component exerted on the surface of the second force plate by the right foot of the subject (left and right force component values are switched for the second plate, i.e., plate signal for $F_{ZL2}$ actually measures $F_{ZR2}$); and $F_{ZR2}$: vertical force component exerted on the surface of the second force plate by the left foot of the subject (left and right force component values are switched for the second plate, i.e., plate signal for $F_{ZR2}$ actually measures $F_{ZL2}$).

The overall vertical force $F_{Z\_VP}$ for the virtual force plate 1400 can be obtained from the following summation equation:

$$F_{Z\_VP} = F_{ZL\_VP} + F_{ZR\_VP} \quad (5)$$

When the left and right vertical force components $F_{ZL\_VP}$, $F_{ZR\_VP}$ are summed in equation (5), the virtual force plate 1400 is considered to have a single measurement surface 1410 (see FIG. 37), without distinguishing between the vertical forces exerted by left and right legs of the subject or patient.

For the virtual force plate 1400, the overall left and right moment components about the x axis $M_{XL\_VP}$, $M_{XR\_VP}$ are obtained from the following equations:

$$M_{XL\_VP} = M_{XL1} + (F_{ZL1} \cdot -d) + (M_{XR2}) + (F_{ZR2} \cdot d) \quad (6)$$

$$M_{XR\_VP} = M_{XR1}(F_{ZR1} \cdot -d) + (M_{XL2}) + (F_{ZL2} \cdot d) \quad (7)$$

where:

$M_{XL1}$: moment component about the x-axis exerted on the surface of the first force plate by the left foot of the subject;

$M_{XR1}$: moment component about the x-axis exerted on the surface of the first force plate by the right foot of the subject;

$M_{XL2}$: moment component about the x-axis exerted on the surface of the second force plate by the right foot of the subject (left and right moment component values are switched for the second plate, i.e., plate signal for $M_{XL2}$ actually measures $M_{XR2}$);

$M_{XR2}$: moment component about the x-axis exerted on the surface of the second force plate by the left foot of the subject (left and right moment component values are switched for the second plate, i.e., plate signal for $M_{XR2}$ actually measures $M_{XL2}$); and d: distance (e.g., in meters) equal to one-half the length of the first force plate or one-half the length of the second force plate (illustrated force plates 1402, 1404 are the same physical size—see FIG. 37).

In equations (6) and (7) above, the parenthetical terms containing the distance value d are required in order to correct for the shifted position of the coordinate axes of the virtual force plate surfaces. Because the virtual plate coordinate axes (i.e., left surface coordinates axes 1412, 1414, 1416 and right surface coordinate axes 1418, 1420, 1422—see FIG. 36) are located between the first and second plates, rather than in the middle of the respective first and second plates, the computed values for the moment components about the x-axis must adjusted accordingly. In particular, as shown in FIG. 36, the origin of the local coordinate axes 1424, 1426, 1428 for the left plate surface of the first force plate 1402 is disposed in the center thereof, while the origin of the local coordinate axes 1430, 1432, 1434 for the right plate surface of the first force plate 1402 is disposed in the center thereof. As discussed above, the second force plate 1404 is rotated 180 degrees relative to the first force plate 1402. Consequently, the physical left and right measurement surfaces of the second force plate 1404 are flipped relative to the first force plate 1402. Referring again to FIG. 36, the origin of the local coordinate axes 1436, 1438, 1440 for the left plate surface of the second force plate 1404 is disposed in the center thereof, while the origin of the local origin of the coordinate axes 1442, 1444, 1446 for the right plate surface of the second force plate 1404 is disposed in the center thereof. In order to correct for the 180 degree rotation of the second force plate 1404, the x and y axes (1436, 1438 and 1442, 1444) of the left and right measurement surfaces, respectively, must be rotated by the angle θ (i.e., 180 degrees) such that respective corrected x' and y' axes (1437, 1439 and 1443, 1445) are obtained. The parenthetical terms containing the distance value d in equations (6) and (7) transform the plate output values measured in accordance with the local coordinate systems of the left and right plate surfaces of each force plate 1402, 1404 into output values based upon the absolute left and right coordinate systems disposed between the two force plates 1402, 1404 (see FIG. 36). The overall moment component about the x-axis $M_{X\_VP}$ for the virtual force plate 1400 can be obtained from the following summation equation:

$$M_{X\_VP} = M_{XL\_VP} + M_{XR\_VP} \quad (8)$$

The overall moment component about the x-axis $M_{X\_VP}$ in equation (8) is defined relative to the absolute coordinate axes 1450, 1452, 1454 in FIG. 37. When the first force plate 1402 is treated as a separate, single measurement surface, the moments acting thereon are defined relative to the local coordinate axes 1456, 1458, 1460 in FIG. 37. Similarly, when the second force plate 1404 is treated as a separate, single measurement surface, the moments acting thereon are defined relative to the local coordinate axes 1462, 1464, 1466 in FIG. 37 (with the corrected, rotated coordinate axes 1463, 1465 shown using dashed lines).

For the virtual force plate 1400, the overall left and right moment components about the y axis $M_{YL\_VP}$, $M_{YR\_VP}$ are obtained from the following equations:

$$M_{YL\_VP} = M_{YL1} + (-M_{YR2}) \quad (9)$$

$$M_{YR\_VP} = M_{YR1} + (-M_{YL2}) \quad (10)$$

where:

$M_{YL1}$: moment component about the y-axis exerted on the surface of the first force plate by the left foot of the subject;

$M_{YR1}$: moment component about the y-axis exerted on the surface of the first force plate by the right foot of the subject;

$M_{YL2}$: moment component about the y-axis exerted on the surface of the second force plate by the right foot of the subject (left and right moment component values are switched for the second plate, i.e., plate signal for $M_{YL2}$ actually measures $M_{YR2}$); and $M_{YR2}$: moment component about the y-axis exerted on the surface of the second force plate by the left foot of the subject (left and right moment component values are switched for the second plate, i.e., plate signal for $M_{YR2}$ actually measures $M_{YL2}$).

The overall moment component about the y-axis $M_{Y\_VP}$ for the virtual force plate 1400 can be obtained from the following summation equation:

$$M_{Y\_VP} = M_{YL\_VP} + M_{YR\_VP} \quad (11)$$

Similar to that described above for equation (8), the overall moment component about the y-axis $M_{Y\_VP}$ in equation (11) is defined relative to the absolute coordinate axes 1450, 1452, 1454 in FIG. 37.

Once the overall vertical force and moment components $F_{Z\_VP}$, $M_{X\_VP}$, $M_{Y\_VP}$ are computed for the virtual force plate 1400, the center of pressure of the vertical force can be computed as follows:

$$x_{P\_VP} = \frac{-M_{Y\_VP}}{F_{Z\_VP}} \quad (12)$$

$$y_{P\_VP} = \frac{M_{X\_VP}}{F_{Z\_VP}} \quad (13)$$

where:

$x_{P\_VP}$, $y_{P\_VP}$: coordinates of the point of application for the vertical force (i.e., center of pressure) on the virtual force plate.

In addition, the data acquisition/data processing device 104 may also determine x and y values for the center-of-gravity (COG) of the subject or patient using the computed center of pressure (COP) values from equations (12) and (13). In one embodiment, the data acquisition/data processing device 104 converts the computed center of pressure (COP) to a center of gravity (COG) for the subject using a Butterworth filter. For example, in this embodiment, a second-order Butterworth filter with a 0.75 Hz cutoff frequency is used. In another embodiment, the center-of-gravity (COG) can be computed in the manner described in pending, commonly-owned U.S. patent application Ser. No. 14/015,535, the entire disclosure of which is incorporated herein by reference.

Now, returning to the flowchart in FIG. 34, after the output signals (i.e., channels) from both measurement assemblies 1402, 1404 (e.g., force plates) are summed in step 1206, the number of recorded channels from multiple devices (e.g., multiple measurement assemblies 1402, 1404 in the form of force plates) are reduced to a single device (e.g., a single measurement assembly in the form of a virtual force plate) in step 1208. Once the final computed result (e.g., the overall vertical force and moment components $F_{Z\_VP}$, $M_{X\_VP}$, $M_{Y\_VP}$) is returned in step 1210, the process ends at step 1212.

In order to execute the calculations described above in equations (1)-(13), the data acquisition/data processing device 104 must be able to identify each of the two measurement assemblies 1402, 1404 that are connected thereto (i.e., the data acquisition/data processing device 104 must be able to distinguish the first force plate from the second force plate). If the data acquisition/data processing device 104 is not able to differentiate between the first and second force plates (e.g., because this is the first time that the first and second force plates have ever been connected to the data acquisition/data processing device 104), the data acquisition/data processing device 104 generates the pop-up window 1300 illustrated in FIG. 35. As diagrammatically indicated by the downwardly-directed arrow 1312, the pop-up window 1300 prompts the system user to manually select the force plate 1304 that is located furthest away from the operator computer system 1306 by standing on the surface of the force plate 1304. When the user stands on the surface of the force plate 1304, the data acquisition/data processing device 104 detects a positive weight in excess of a set value (e.g., 1 Newton) for a predetermined number of seconds (e.g., 2 seconds). After standing on the plate 1304, the user is then instructed to press the "OK" button 1308 to complete his or her selection, and confirm the proper plate order. Alternatively, if the user inadvertently selected the incorrect force plate (e.g., force plate 1302, which is closest to the operator computer system 1306), he or she can always revise the selection by pressing the "Cancel" button 1310. Once the user manually selects the force plate 1304 that is located furthest from the operator computer system 1306 using the pop-up window 1300, the data acquisition/data processing device 104 designates the force plates 1302, 1304 as the first and second force plates, respectively, for the purpose of the calculations described above in equations (1)-(13). Thus, because the second force plate 1304 is rotated 180 degrees relative to the designated standard orientation of the plate coordinate axes, the matrix rotation calculations explained above are performed on the output values from the second force plate 1304 in order to compensate for its rotated position. Once the furthest force plate 1304 has been configured as the second force plate 1304 by the data acquisition/data processing device 104 (e.g., by equating its serial number with the second force plate designation), the pop-up window 1300 will not be subsequently displayed to the system user when the system user utilizes the measurement and testing software program at a later date or time.

It is readily apparent that the embodiments of the measurement and testing system 100 described above offer numerous advantages and benefits. In one or more embodiments, the measurement and testing system 100 discussed herein employs inventive filtering techniques in order to create a single, easily understandable report from data acquired on a plurality of different dates, thereby facilitating the analysis of the data by a user of the system. Moreover, in one or more embodiments, the measurement and testing system 100 includes a data acquisition and processing device which is specially programmed to automatically regulate the availability of tests in accordance with the type of measurement assembly or assemblies that is being utilized in the measurement system by filtering the tests that cannot be executed properly on a particular measurement assembly or assemblies. Furthermore, in one or more embodiments, the measurement and testing system 100 has a data acquisition and processing device which is specially programmed to create one or more virtual measurement assemblies from a plurality of physical measurement assemblies that are operatively coupled thereto in different orientations, such that the system is capable of having a large measurement surface area, while still being readily portable.

Figure 38:
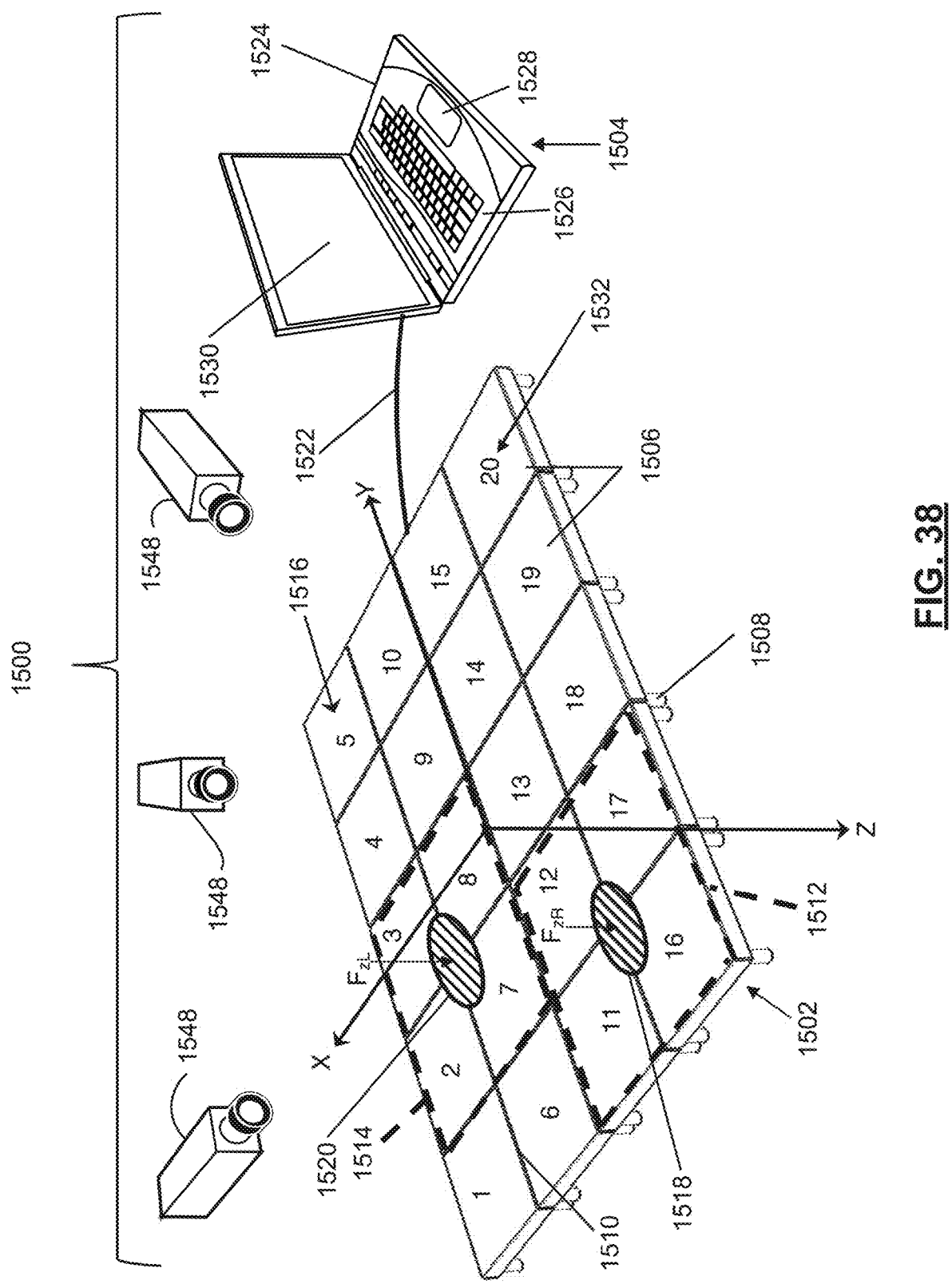
FIG. 38 is a perspective view of a measurement and testing system comprising a force plate array that utilizes virtual force plates, according to another embodiment of the invention.

According to still another aspect of the illustrative embodiment, with initial reference to FIG. 38, the data acquisition/data processing device is specially programmed to determine one or more subsets of a plurality of measurement assemblies experiencing a load from one or more body portions of the subject, to construct one or more virtual measurement assemblies from the one or more respective subsets, and to determine output forces and/or moments for the one or more virtual measurement assemblies using the signals from the measurement devices of the measurement assemblies in the one or more subsets.

An illustrative embodiment of a measurement and testing system utilizing virtual force plates is seen generally at 1500 in FIG. 38. The force plate system 1500 generally comprises a force plate array 1502 operatively coupled to a data acquisition and processing device 1504 by virtue of an electrical cable 1522. In one or more embodiments, the electrical cable 1522 is used for data transmission, as well as for providing power to the force plates of the force plate array 1502. Preferably, the electrical cable 1522 contains a plurality of electrical wires bundled together, with at least one wire being used for power and at least another wire being used for transmitting data. The bundling of the power and data transmission wires into a single electrical cable 1522 advantageously creates a simpler and more efficient design. In addition, it enhances the safety of the testing environment when human subjects are being tested on the force plate array 1502. However, it is to be understood that the force plate array 1502 can be operatively coupled to the data acquisition and processing device 1504 using other signal transmission means, such as a wireless data transmission system. If a wireless data transmission system is employed, it is preferable to provide the force plate array 1502 with a separate power supply in the form of an internal power supply or a dedicated external power supply.

Referring again to FIG. 38, it can be seen that the force plate array 1502 according to the illustrated embodiment of the invention includes a plurality of measurement assemblies in the form of force plates 1506 that are disposed adjacent to one another, and each being separated by a narrow gap 1510. As depicted in FIG. 38, each force plate 1506 of the force plate array 1502 is preferably provided with at least four (4) measurement devices (i.e., force transducers 1508 thereunder). Also, each force plate 1506 has a measurement surface (i.e., top surface 1516) that is configured to receive at least one portion of a body of a subject (e.g., a foot/leg of a subject). In one or more embodiments, a subject stands in an upright position on the force plate array 1502 and each foot of the subject is placed on one or more top surfaces 1516 of one or more force plates 1506 in the force plate array 1502 (e.g., in FIG. 38, the left foot 1520 of the subject, as represented by the first hatched area, is disposed on the top surfaces 1516 of force plate nos. 2, 3, 7, 8, whereas the right foot 1518 of the subject, as represented by the second hatched area, is disposed on the top surfaces 1516 of force plate nos. 11, 12, 16, 17). In FIG. 38, each force plate 1506 of the force plate array 1502 is identified by a corresponding identification number 1532 (i.e., force plate no. 1, 2, 3, 4, 5, etc.).

As shown in FIG. 38, the data acquisition and processing device 1504 (e.g., in the form of a laptop digital computer) generally includes a base portion 1524 with a central processing unit (CPU) disposed therein for collecting and processing the data that is received from the force plate array 1502, and a plurality of devices 1526-1530 operatively coupled to the central processing unit (CPU) in the base portion 1524. Preferably, the devices that are operatively coupled to the central processing unit (CPU) comprise user input devices 1526, 1528 in the form of a keyboard 1526 and a touchpad 1528, as well as a graphical user interface in the form of a laptop LCD screen 1530. While a laptop type computing system is depicted in the embodiment of FIG. 38, one of ordinary skill in the art will appreciate that another type of data acquisition and processing device 1504 can be substituted for the laptop computing system such as, but not limited to, a palmtop computing device (i.e., a PDA) or a desktop type computing system having a plurality of separate, operatively coupled components (e.g., a desktop type computing system including a main housing with a central processing unit (CPU) and data storage devices, a remote monitor, a remote keyboard, and a remote mouse, as depicted in FIGS. 1 and 35). The laptop computing system 1504 in FIG. 38 comprises the same constituent hardware components as those described above with regard to data acquisition and processing device 104 (e.g., a microprocessor 104a for processing data, memory 104b (e.g., random access memory or RAM) for storing data during the processing thereof, and data storage device(s) 104c).

As diagrammatically illustrated in FIG. 38, the data acquisition and processing device 1504 is specially programmed to determine a first subset of the plurality of measurement assemblies (i.e., force plates nos. 11, 12, 16, 17) experiencing a load (e.g., vertical force $F_{zR}$) from a first portion of the body of the subject (i.e., right foot/leg 1518) and a second subset of the plurality of measurement assemblies (i.e., force plates nos. 2, 3, 7, 8) experiencing a load (e.g., vertical force $F_{zL}$) from a second portion of the body of the subject (i.e., left foot/leg 1520). The data acquisition and processing device 1504 is further specially programmed to construct a first virtual measurement assembly 1512 from the first subset (i.e., force plates nos. 11, 12, 16, 17) and a second virtual measurement assembly 1514 from the second subset (i.e., force plates nos. 2, 3, 7, 8), and to determine respective output forces and moments for the first and second virtual measurement assemblies 1512, 1514 using the respective signals from the measurement devices of the measurement assemblies (i.e., force plates) in the first and second subsets. Also, the data acquisition and processing device 1504 may be specially programmed to compute a load center of pressure for each of the first and second virtual measurement assemblies 1512, 1514 using the respective signals from the measurement devices of the measurement assemblies (i.e., force plates) in the first and second subsets. The output forces and moments for the virtual measurement assemblies 1512, 1514 may be determined in a manner similar to that described above with regard to equations (3), (4), (6), (7), (9), and (10) by mathematically combining the individual forces and moments for force plates nos. 11, 12, 16, 17, and by mathematically combining the individual forces and moments for force plates nos. 2, 3, 7, 8. The load centers of pressures for the virtual measurement assemblies 1512, 1514 may be determined in a manner similar to that described above with regard to equations (12) and (13).

As shown in FIG. 38, each of the measurement surfaces 1516 of the plurality of measurement assemblies 1506 has a footprint that is substantially equal to the first and second feet 1518, 1520 of the subject such that each of the first and second feet 1518, 1520 generally lands on a different one of the measurement surfaces 1516 of the plurality of measurement assemblies 1506 when the subject traverses the force plate array 1502 comprising the plurality of measurement assemblies 1506. In another embodiment, each of the measurement surfaces of the plurality of measurement assemblies may have a footprint that is smaller than each of the first and second feet 1518, 1520 of the subject so that each foot of the subject also generally lands on a different one of the measurement surfaces 1516 of the plurality of measurement assemblies 1506 when the subject traverses the force plate array 1502.

Figure 42:
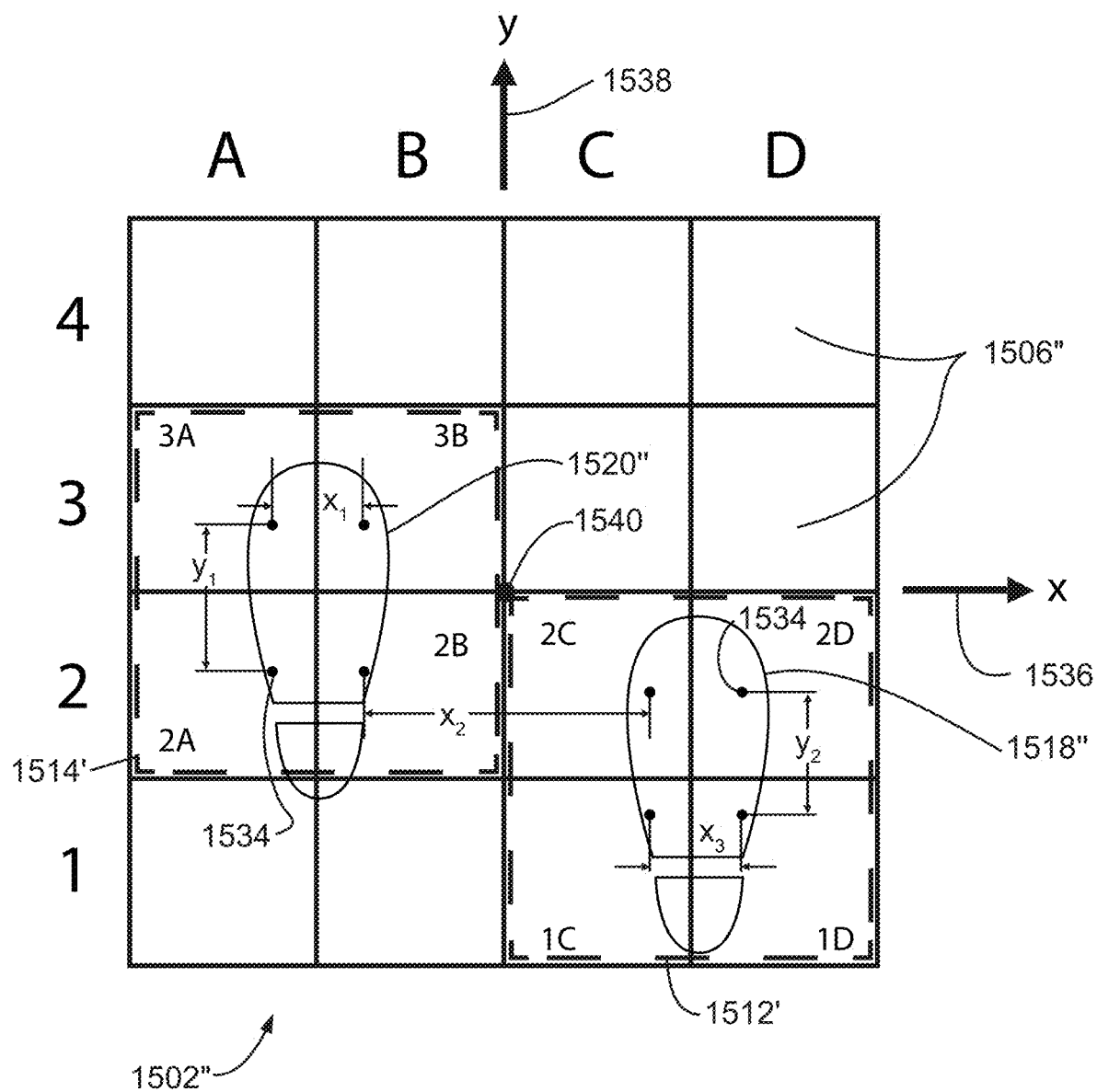
FIG. 42 is a top view of yet another force plate array of another alternative measurement and testing system that illustrates the manner in which distances are computed between the centers of pressure for each foot of the subject, according to still another embodiment of the invention.

In an illustrative embodiment, with reference to the top view of the force plate array 1502" of FIG. 42, the data acquisition and processing device 1504 is specially programmed to use a calculated distance between load centers of pressure in order to determine whether each measurement assembly 1506" in a pair of measurement assemblies (i.e., a pair of force plates) is to be assigned to a same one of the first and second subsets or a different one of the first and second subsets. Initially, the data acquisition and processing device 1504 is specially programmed to compute a local load center of pressure (i.e., points 1534 in FIG. 42) for each measurement assembly (i.e., force plates 1C, 1D, 2A, 2B, 2C, 2D, 3A, 3B) in the plurality of measurement assemblies (i.e., force plate array 1502") experiencing a load from the subject. In FIG. 42, it can be seen that the right foot 1518" of the subject exerts a load (i.e., a force and/or moment) on force plates 1C, 1D, 2C, 2D, while the left foot 1520" of the subject exerts a load (i.e., a force and/or moment) on force plates 2A, 2B, 3A, 3B. In the manner described above, the local load center of pressure is computed individually for each of the force plates 1C, 1D, 2A, 2B, 2C, 2D, 3A, 3B experiencing a load from either the subject's right foot 1518" or the subject's left foot 1520" relative to the force plate's local coordinate axes (i.e., the origins of the local coordinate axes may be disposed in the middle of each force plate). Then, the local center of pressure coordinates determined for each of the force plates 1C, 1D, 2A, 2B, 2C, 2D, 3A, 3B are converted to global center of pressure coordinates. As shown in FIG. 42, the origin 1540 of the x-axis 1536 and the y-axis 1538 of the global coordinate system of the force plate array 1502" may be disposed in the middle of the array 1502", and at the corners of force plates 2B, 2C, 3B, 3C. Once all of the local center of pressure coordinates have been converted to global center of pressure coordinates by the data acquisition and processing device 1504, the data acquisition and processing device 1504 is specially programmed to calculate distances between the load centers of pressure. For example, referring again to FIG. 42, the distance $x_1$ is computed between the load center of pressure points on force plates 3A and 3B, the distance $x_2$ is computed between the load center of pressure points on force plates 2B and 2C, and the distance $x_3$ is computed between the load center of pressure points on force plates 1C and 1D. Similarly, distance $y_1$ is computed between the load center of pressure points on force plates 2A and 3A and the distance $y_2$ is computed between the load center of pressure points on force plates 1D and 2D. After which, as will be explained hereinafter, the data acquisition and processing device 1504 uses the calculated distances $x_1$, $x_2$, $x_3$, $y_1$, $y_2$ between the load centers of pressure 1534 in order to determine whether each measurement assembly 1506" in a pair of measurement assemblies is to be assigned to a same one of the first and second subsets (i.e., a same one of virtual force plates 1512', 1514') or a different one of the first and second subsets (i.e., a different one of virtual force plates 1512', 1514').

Referring again to FIG. 42, in the illustrated embodiment, the data acquisition and processing device 1504 is specially programmed to compare the calculated distances $x_1$, $x_2$, $x_3$, $y_1$, $y_2$ between the load centers of pressure 1534 to at least one foot size parameter (i.e., a foot width of the subject or foot length) of the subject in order to determine whether each measurement assembly 1506" in a pair of measurement assemblies is to be assigned to a same one of the first and second subsets (i.e., a same one of virtual force plates 1512', 1514') or to a different one of the first and second subsets (i.e., a different one of virtual force plates 1512', 1514'). For example, suppose the subject has a foot width of approximately 3.5 inches and a foot length of approximately 11.0 inches. Also, suppose, for example, that the distance $x_1$ is approximately equal to 2.75 inches, the distance $x_2$ is approximately equal to 4.3 inches, the distance $x_3$ is approximately equal to 2.85 inches, the distance $y_1$ is approximately equal to 9.0 inches, and the distance $y_2$ is approximately equal to 9.25 inches. Using these exemplary numerical values, the data acquisition and processing device 1504 determines that the center of pressure coordinates 1534 that are located on force plates 3A and 3B each correspond to a load generated by the same foot (i.e., the left foot 1520") of the subject because the distance $x_1$ between these two center of pressure points is approximately equal to 2.75 inches, which is less than the approximate foot width of the subject, namely 3.5 inches. Similarly, the data acquisition and processing device 1504 determines that the center of pressure coordinates 1534 that are located on force plates 1C and 1D each correspond to a load generated by the same foot (i.e., the right foot 1518") of the subject because the distance $x_3$ between these two center of pressure points is approximately equal to 2.85 inches, which is less than the approximate foot width of the subject, namely 3.5 inches. In contrast, the data acquisition and processing device 1504 determines that the center of pressure coordinates 1534 that are located on force plates 2B and 2C each correspond to a load generated by different feet of the subject, namely the right and left feet 1518", 1520", because the distance $x_2$ between these two center of pressure points is approximately equal to 4.3 inches, which is significantly greater than the approximate foot width of the subject (i.e., 3.5 inches), and thus, the respective loads corresponding to these two points must have been applied by separate feet. In addition, the data acquisition and processing device 1504 determines that the center of pressure coordinates 1534 that are located on force plates 2A and 3A each correspond to a load generated by the same foot (i.e., the left foot 1520") of the subject because the distance $y_1$ between these two center of pressure points is approximately equal to 9.0 inches, which is less than the approximate foot length of the subject, namely 11.0 inches. Similarly, the data acquisition and processing device 1504 determines that the center of pressure coordinates 1534 that are located on force plates 1D and 2D each correspond to a load generated by the same foot (i.e., the right foot 1518") of the subject because the distance $y_2$ between these two center of pressure points is approximately equal to 9.25 inches, which also is less than the approximate foot length of the subject, namely 11.0 inches. Because the intent of creating the virtual force plates 1512', 1514' in the force plate array 1502" is to track the change in the center of pressure for each of the subject's feet 1518", 1520" independently from one another, when load center of pressure points disposed on a subset of force plates are created by the same foot, each of these force plates in the subset will be assigned to a single virtual plate by the data acquisition and processing device 1504. In the illustrated example described above with reference to FIG. 42, force plates 1C and 1D and force plates 2C and 2D will be assigned to the same virtual force plate 1512' because the loads acting thereon are all applied by the right foot 1518" of the subject. Similarly, force plates 2A and 2B and force plates 3A and 3B will be assigned to the same virtual force plate 1514' because the loads acting thereon are all applied by the left foot 1520" of the subject. In contrast, the force plates 2B and 2C will be assigned to different virtual force plate 1512', 1514' because the loads acting thereon are applied by different feet 1518", 1520" of the subject.

Also, in the illustrated embodiment of FIG. 42, the data acquisition and processing device 1504 is specially programmed to additionally compare the calculated distances $x_1$, $x_2$, $x_3$, $y_1$, $y_2$ between the load centers of pressure 1534 to at least one step size parameter (i.e., the step width or the step length) of the subject in order to determine whether each measurement assembly 1506" in a pair of measurement assemblies is to be assigned to a same one of the first and second subsets (i.e., a same one of virtual force plates 1512', 1514') or to a different one of the first and second subsets (i.e., a different one of virtual force plates 1512', 1514'). For example, suppose the subject has a step width of approximately 4.35 inches and a step length of approximately 30.0 inches. Also, as described above, suppose the distance $x_1$ is approximately equal to 2.75 inches, the distance $x_2$ is approximately equal to 4.3 inches, the distance $x_3$ is approximately equal to 2.85 inches, the distance $y_1$ is approximately equal to 9.0 inches, and the distance $y_2$ is approximately equal to 9.25 inches. Using these exemplary numerical values, the data acquisition and processing device 1504 determines that the center of pressure coordinates 1534 that are located on force plates 3A and 3B each correspond to a load generated by the same foot (i.e., the left foot 1520") of the subject because the distance $x_1$ between these two center of pressure points is approximately equal to 2.75 inches, which is less than the approximate step width of the subject, namely 4.35 inches. Similarly, the data acquisition and processing device 1504 determines that the center of pressure coordinates 1534 that are located on force plates 1C and 1D each correspond to a load generated by the same foot (i.e., the right foot 1518") of the subject because the distance $x_3$ between these two center of pressure points is approximately equal to 2.85 inches, which is less than the approximate step width of the subject, namely 4.35 inches. In contrast, the data acquisition and processing device 1504 determines that the center of pressure coordinates 1534 that are located on force plates 2B and 2C each correspond to a load generated by different feet of the subject, namely the right and left feet 1518", 1520", because the distance $x_2$ between these two center of pressure points is approximately equal to 4.3 inches, which is significantly greater than the approximate foot width of the subject (i.e., 3.5 inches) and is approximately equal to the average step width of the subject of 4.35 inches, and thus, the respective loads corresponding to these two points must have been applied by separate feet. In the illustrated example described above, with reference to FIG. 42, force plates 1C and 1D will be assigned to the same virtual force plate 1512' because the loads acting thereon are all applied by the right foot 1518" of the subject. Similarly, force plates 3A and 3B will be assigned to the same virtual force plate 1514' because the loads acting thereon are all applied by the left foot 1520" of the subject. In contrast, force plates 2B and 2C will be assigned to different virtual force plate 1512', 1514' because the loads acting thereon are applied by different feet 1518", 1520" of the subject.

Figure 43:
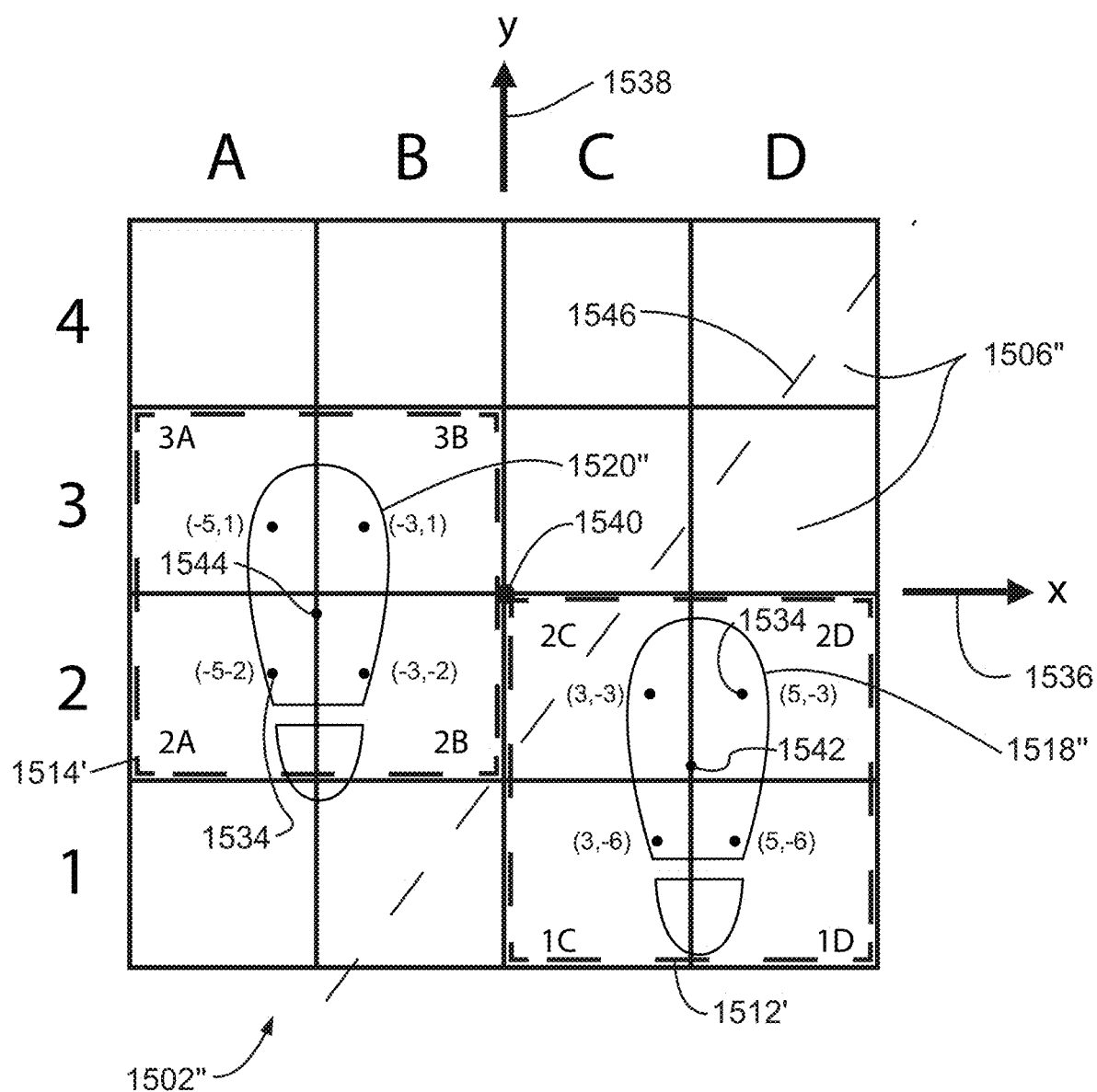
FIG. 43 is another top view of the force plate array of FIG. 42 illustrating the manner in which a cluster computational analysis is applied to the centers of pressure for each foot of the subject, according to yet another embodiment of the invention.

In the illustrated embodiment, with reference to the top view of the force plate array 1502" of FIG. 43, the data acquisition and processing device 1504 is specially programmed to compare each of the computed load centers of pressure to one another using a cluster computational method so as to determine whether particular measurement assemblies 1506" are to be assigned to a same one of the first and second subsets or to a different one of the first and second subsets. As described above, the data acquisition and processing device 1504 initially is specially programmed to compute a local load center of pressure (i.e., points 1534 in FIG. 43) for each measurement assembly (i.e., force plates 1C, 1D, 2A, 2B, 2C, 2D, 3A, 3B) in the plurality of measurement assemblies (i.e., force plate array 1502") experiencing a load from the subject. In FIG. 43, it can be seen that the right foot 1518" of the subject exerts a load (i.e., a force and/or moment) on force plates 1C, 1D, 2C, 2D, while the left foot 1520" of the subject exerts a load (i.e., a force and/or moment) on force plates 2A, 2B, 3A, 3B. In the manner described above, the local load center of pressure is computed individually for each of the force plates 1C, 1D, 2A, 2B, 2C, 2D, 3A, 3B experiencing a load from either the subject's right foot 1518" or the subject's left foot 1520" relative to the force plate's local coordinate axes (i.e., the origins of the local coordinate axes may be disposed in the middle of each force plate). Then, the local center of pressure coordinates determined for each of the force plates 1C, 1D, 2A, 2B, 2C, 2D, 3A, 3B are converted to global center of pressure coordinates. As shown in FIG. 43, the origin 1540 of the x-axis 1536 and the y-axis 1538 of the global coordinate system of the force plate array 1502" may be disposed in the middle of the array 1502", and at the corners of force plates 2B, 2C, 3B, 3C. Once all of the local center of pressure coordinates have been converted to global center of pressure coordinates by the data acquisition and processing device 1504, the data acquisition and processing device 1504 is specially programmed to carry out a cluster computational method (e.g., a k-means cluster computational method).

Referring to FIG. 43, it can be seen that there are total of eight (8) sets of load center of pressure coordinates 1534 that are to be organized into two groups (i.e., one for the right foot of the subject 1518" and one for the left foot of the subject 1520") using the cluster computation method. For example, based upon the absolute coordinates axes 1536, 1538 in FIG. 43, the load center of pressure coordinates 1534 are (3, −3), (5, −3), (3, −6), (5, −6), (−3, 1), (−5, 1), (−3, −2), (−5, −2). First of all, the data acquisition and processing device 1504 determines an initial best-guess for the coordinate values of each of the centroids for the two groups. For example, suppose that the first two load center of pressure coordinates, namely (3, −3), (5, −3), are used by the data acquisition and processing device 1504 as the first guesses for the centroids (i.e., $C_1$=(3, −3), $C_2$=(5, −3)). After initial values of the centroids are established, the data acquisition and processing device 1504 computes the distance between each of the cluster/group centroids $C_1$, $C_2$ and each of the load center of pressure coordinates 1534 using the following distance formula:

$$d=\sqrt{(x_2-x_1)^2+(y_2-y_1)^2} \qquad (14)$$

where:

$x_2$: x-coordinate of the centroid;
$x_1$: x-coordinate of the load center of pressure;
$y_2$: y-coordinate of the centroid; and
$y_1$: y-coordinate of the load center of pressure.

After computing the distance between each of the cluster/group centroids $C_1$, $C_2$ and each of the load center of pressure coordinates 1534 using equation (14) above, the data acquisition and processing device 1504 assigns each of the load center of pressure coordinates 1534 to either the first group or the second group based upon whether the minimum distance was computed for the first centroid or the second centroid. For example, based upon the first guesses for the centroids above, the load center of pressure coordinates (3, −3), (3, −6), (−3, 1), (−5, 1), (−3, −2), and (−5, −2) are closer to the first centroid $C_1=(3, -3)$, and thus are assigned to the first group (i.e., Group I). Conversely, based upon the first guesses for the centroids above, the load center of pressure coordinates (5, −3), (5, −6), are closer to the second centroid $C_2=(5, -3)$, and thus are assigned to the second group (i.e., Group II). Now that the members of each group have been determined by the data acquisition and processing device 1504, the new centroids for each group are computed based upon these new group memberships. The first group has six members, and thus the first centroid is computed as follows:

$$C_1 = \left(\left(\frac{3+3+(-3)+(-5)+(-3)+(-5)}{6}\right),\right. \tag{15}$$
$$\left.\left(\frac{(-3)+(-6)+1+1+(-2)+(-2)}{6}\right)\right)$$
$$C_1 = \left(\left(\frac{-10}{6}\right),\left(\frac{-11}{6}\right)\right) = (-1.67, -1.83)$$

The second group has two members, and thus the second centroid is computed as follows:

$$C_2 = \left(\left(\frac{5+5}{2}\right),\left(\frac{(-3)+(-6)}{2}\right)\right) = \left(\left(\frac{10}{2}\right),\left(\frac{-9}{2}\right)\right) = (5, -4.5) \tag{16}$$

After the new centroids are computed, the data acquisition and processing device 1504 is specially programmed to use equation (14) above in order to compute the distance between each of the new cluster/group centroids $C_1$, $C_2$ and each of the load center of pressure coordinates 1534. Then, the data acquisition and processing device 1504 once again assigns each of the load center of pressure coordinates 1534 to either the first group or the second group based upon whether the minimum distance was computed for the first centroid or the second centroid. After the data acquisition and processing device 1504 determines the revised members of each group, the new centroids for each group are once again computed based upon these new group memberships. These same series of steps described above are iterated until the members of each group remain constant (i.e., none of the load center of pressure coordinates 1534 move from one group to the other). After the load center of pressure coordinates 1534 no longer switch groups, the computation of the k-means clustering has reached its stability and no more iterations are needed. At this point, the data acquisition and processing device 1504 determines the final groupings and the final centroids for each group. In the illustrated embodiment, referring again to FIG. 43, the load center of pressure coordinates (3, −3), (5, −3), (3, −6), and (5, −6) are assigned to the first group (i.e., group I), which has a centroid located at point 1542 (i.e., the centroid for group I is (4, −4.5)). The load center of pressure coordinates (−3, 1), (−5, 1), (−3, −2), and (−5, −2) are assigned to the second group (i.e., group II), which has a centroid located at point 1544 (i.e., the centroid for group I is (−4, −0.5)). The diagonal dividing line 1546 is used to diagrammatically separate the two groups of load center of pressure coordinates in FIG. 43.

As such, based upon the results of the cluster computational method described above, the data acquisition and processing device 1504 determines that the center of pressure coordinates (3, −3), (5, −3), (3, −6), and (5, −6), which are located on force plates 2C, 2D, 1C, and 1D respectively, each correspond to a load generated by the same foot (i.e., the right foot 1518") of the subject because each of these center of pressure coordinates 1534 are members of the same group (i.e., group I). Similarly, the data acquisition and processing device 1504 determines that the center of pressure coordinates (−5, 1), (−3, 1), (−5, −2), and (−3, −2), which are located on force plates 3A, 3B, 2A, and 2B respectively, each correspond to a load generated by the same foot (i.e., the left foot 1520") of the subject because each of these center of pressure coordinates 1534 are members of the same group (i.e., group II). In the illustrated example described above, with reference to FIG. 43, force plates 1C, 1D, 2C, and 2D will be assigned to the same virtual force plate 1512' because the loads acting thereon are all applied by the right foot 1518" of the subject. Similarly, force plates 2A, 2B, 3A, and 3B will be assigned to the same virtual force plate 1514' because the loads acting thereon are all applied by the left foot 1520" of the subject.

Also, with reference again to FIG. 38, the illustrated embodiment of the measurement and testing system 1500 utilizing virtual force plates may further include a motion capture system. As shown in FIG. 38, the motion capture system includes a plurality of motion capture devices (i.e., video cameras 1548) that capture the motion of the first body portion of the subject (i.e., right foot/leg 1518) and the second body portion of the subject (i.e., left foot/leg 1520). The video cameras 1548 of the motion capture system generate motion capture data representative of the captured motion (i.e., video images) of the first body portion of the subject 1518 and the second body portion of the subject 1520. While three (3) cameras 1548 are depicted in FIG. 38, one of ordinary skill in the art will appreciate that more or less cameras can be utilized, provided that at least two cameras 1548 are used. The motion capture data may be used by the data acquisition and processing device 1504 to make a supplementary determination of applied load positions on each of the measurement assemblies (i.e., force plates 1506) in the first and second subsets so as to correct for measurement errors resulting from a single measurement assembly 1506 experiencing loads from both the first and second limbs 1518, 1520 of the subject. That is, when a single force plate 1506 is experiencing loads from both the first and second limbs 1518, 1520 of the subject (i.e., double contact on the force plate 1506 by both limbs 1518, 1520), the motion capture data may be used by the data acquisition and processing device 1504 to determine the relative positions of the two limbs 1518, 1520 on that force plate 1506. The data acquisition and processing device 1504 may also utilize the motion capture data in conjunction with the distance measurements and/or the cluster computational method described above in order to accurately determine the force plates 1506 that are being contacted by each limb 1518, 1520 of the subject. In addition, the motion capture data may be utilized by the data acquisition and processing device 1504 to determine whether a load that is being applied to the particular one of the plurality of measurement assemblies 1506 is being applied by the first body portion of the subject 1518 or the second body portion of the subject 1520.

The motion capture system illustrated in FIG. 38 is a markerless-type motion detection/motion capture system. That is, the motion capture system of FIG. 38 uses a plurality of high speed video cameras to record the motion of a subject without requiring any markers to be placed on the subject. However, in another embodiment, a marker-based motion capture system is utilized. In this embodiment, the subject is provided with a plurality of markers disposed thereon. These markers are used to record the position of the limbs of the subject in 3-dimensional space. In this embodiment, the plurality of cameras 1548 are used to track the position of the markers as the subject moves his or her limbs in 3-dimensional space. For example, the subject may have a plurality of single markers applied to anatomical landmarks (e.g., the iliac spines of the pelvis, the malleoli of the ankle, and the condyles of the knee), or clusters of markers applied to the middle of body segments. As the subject executes particular movements on the force plate array 1502, the data acquisition/data processing device 1504 calculates the trajectory of each marker in three (3) dimensions. Then, once the positional data is obtained using the motion capture system, the position of the subject's limbs 1518, 1520 may be determined, and inverse kinematics may be employed in order to determine the joint angles of the subject. Both of the aforementioned markerless and marker-based motion capture systems are optical-based systems. In one embodiment, the optical motion capture systems utilize visible light, while in another alternative embodiment, the optical motion capture system employs infrared light (e.g., the system could utilize an infrared (IR) emitter to project a plurality of dots onto objects in a particular space as part of a markerless motion capture system). For example, a motion capture device with one or more cameras, one or more infrared (IR) depth sensors, and one or more microphones may be used to provide full-body three-dimensional (3D) motion capture, facial recognition, and voice recognition capabilities. It is also to be understood that, rather than using an optical motion capture system, a suitable magnetic or electromechanical motion detection/capture system may also be employed in the measurement and testing system described herein, or a motion capture system that utilizes a plurality of inertial measurement units (IMUs) disposed on the limbs of the subject.

In a further embodiment of the measurement and testing system of FIG. 38, the data acquisition and processing device 1504 is specially programmed to use a predetermined time delay in order to determine whether each measurement assembly 1506 in a pair of measurement assemblies is to be assigned to a same one of the first and second subsets (i.e., a same one of virtual force plates 1512, 1514) or to a different one of the first and second subsets (i.e., a different one of virtual force plates 1512, 1514). For example, the predetermined time delay utilized by the data acquisition and processing device 1504 may constitute the average time duration (e.g., 0.30 seconds) of the right or left swing phase of the subject (i.e., from left toe off to left heel contact, or from right toe off to right heel contact).

Figure 39:
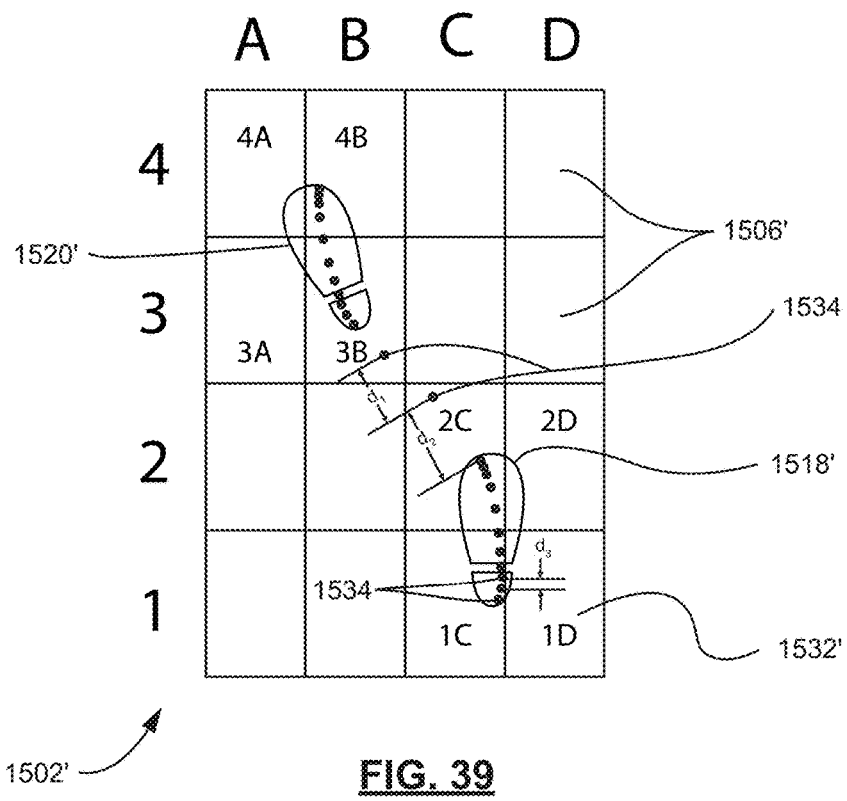
FIG. 39 is a top view of another force plate array of an alternative measurement and testing system that illustrates the manner in which distances are computed between the varying subject's center of pressure over time, according to yet another embodiment of the invention.

In yet a further embodiment of the measurement and testing system of FIG. 38, the data acquisition and processing device 1504 is specially programmed to compute, by using the output data, a series of load centers of pressure 1534 for the subject (see FIG. 39). In FIG. 39, the points 1534 represent the path of the subject's center of pressure over time as the subject traverses the force plate array 1502'. The force plate array 1502' of FIG. 39 comprises a plurality of measurement assemblies in the form of rectangular force plates 1506' (i.e., force plates 1A-4D) with identification numbers 1532'. As shown in FIG. 39, the subject's right foot 1518' is disposed on force plates 1C, 1D, 2C, 2D, while the subject's left foot 1520' is disposed on force plates 3A, 3B, 4A, 4B. In FIG. 39, the force plates 1A-4D forming the force plate array 1502' are being treated as a single overall virtual force plate with the progression of the subject's center of pressure over time being represented by the series of points or dots 1534. When the points or the dots 1534 are close together (e.g., as those illustrated under the right foot 1518' and the left foot 1520' of the subject), there is a small change in the subject's center of pressure over time. Conversely, when the points or the dots 1534 are far apart (e.g., those spaced apart by distances $d_1$ and $d_2$), there is a large change in the subject's center of pressure over time.

The data acquisition and processing device 1504 is specially programmed to compare each of the computed load centers of pressure 1534 to one another so as to determine a substantial incremental increase in a magnitude of the computed load center of pressure that corresponds to double stance in a gait cycle of the subject. For example, with reference to FIG. 39, the data acquisition and processing device 1504 is specially programmed to compare the load centers of pressure 1534 separated by the large distances $d_1$ and $d_2$ to the load centers of pressure 1534 separated by only small distances between one another (e.g., distance $d_3$ in FIG. 39) in order to determine the double stance phase of the subject's gait cycle. Because a rapid change in a person's center of pressure is experienced during the double stance phase of the gait cycle, the large distances $d_1$ and $d_2$ between the subject's centers of pressure on force plates 2C and 3B clearly indicates that the double stance phase of the subject's gait cycle is occurring during this time. The data acquisition and processing device 1504 is specially programmed to utilize the determined substantial incremental increase in the magnitude of the computed load center of pressure (e.g., as indicated by the large spacing distances $d_1$ and $d_2$ in FIG. 39) in order to determine whether the load that is being applied to the particular one of the plurality of measurement assemblies 1506' is being applied by the first body portion of the subject (i.e., right foot/leg 1518') or the second body portion of the subject (i.e., left foot/leg 1520'). In addition, the data acquisition and processing device 1504 is specially programmed to compare each of the computed load centers of pressure 1534 to one another so as to determine differences in magnitude between successive computed load centers of pressure 1534 for a predetermined time increment, and to compare the determined differences in magnitude between successive computed load centers of pressure 1534 in order to determine whether the load that is being applied to the particular one of the plurality of measurement assemblies is being applied by the first body portion of the subject (i.e., right foot/leg 1518') or the second body portion of the subject (i.e., left foot/leg 1520'). In particular, once the load center of pressure points 1534 corresponding to the double stance phase of the gait cycle are identified, the data acquisition and processing device 1504 determines that the closely spaced-apart points 1534 disposed on force plates 1C and 2C correspond to the same foot of the subject (i.e., the right foot 1518' of the subject), whereas the closely spaced-apart points 1534 disposed on force plates 3B and 4B correspond to the same foot of the subject (i.e., the left foot 1520' of the subject). Also, based upon the coordinate values of each load center of pressure point 1534, the data acquisition and processing device 1504 determines that the closely spaced-apart points 1534 disposed on force plates 1C and 2C correspond to the right foot 1518' of the subject, while the closely spaced-apart points 1534 disposed on force plates 3B and 4B correspond to the left foot 1520' of the subject (i.e., the center of pressure points corresponding to the left foot 1520' of the subject will have x-coordinate values that are either less than (if the x-axis is pointing to the right), or greater than (if the x-axis is pointing to the left) the x-coordinate values of the center of pressure points corresponding to the right foot 1518' of the subject).

Figure 40:
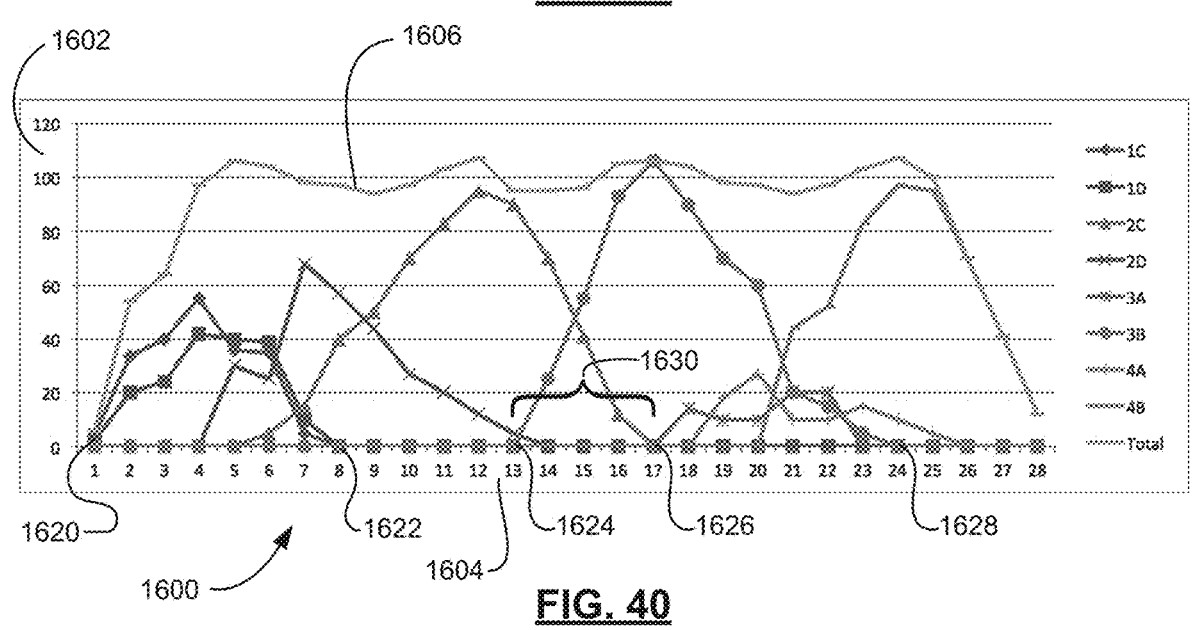
FIG. 40 is a graph illustrating a magnitude of a vertical force being applied to each of the force plates in the force plate array of FIG. 39 by a subject.

In still a further embodiment of the measurement and testing system, the data acquisition and processing device 1504 is specially programmed to compare, by using the output data for the force plates 1A-4D in the force plate array 1502', forces applied to measurement surfaces of respective ones of the plurality of measurement assemblies 1506' as each of the plurality of measurement assemblies 1506' are activated so as to determine whether the load that is being applied to the particular one of the plurality of measurement assemblies 1506' is being applied by the first body portion of the subject (i.e., right foot/leg 1518) or the second body portion of the subject (i.e., left foot/leg 1520). In FIG. 40, the vertical forces ($F_z$) being applied to each of the active measurement assemblies (i.e., force plates 1506') in the force plate array 1502' of FIG. 39 are plotted as function of time. As such, the y-axis 1602 of the graph 1600 of FIG. 40 corresponds to the vertical reaction force (e.g., as listed in the percentage of the subject's weight), and the x-axis 1604 of the graph 1600 of FIG. 40 corresponds to time (e.g., in seconds). In addition to the forces being applied to each of the active measurement assemblies (i.e., force plates 1506') in the force plate array 1502', the graph 1600 of FIG. 40 also includes a curve 1606 of the total vertical force being applied to the force plates of the force plate array 1502'.

Now, with reference to FIG. 40, the manner in which the data acquisition and processing device 1504 determines whether the load is being applied by the first body portion of the subject (i.e., right foot/leg 1518') or the second body portion of the subject (i.e., left foot/leg 1520') will be explained. In FIG. 40, the right foot heel down position occurs at point 1620, while the right foot heel up position occurs at point 1622. Between these two points 1620, 1622, force plates 1C, 1D, 2C, 2D of the force plate array 1502' (see FIG. 39) are experiencing a load. Turning again to FIG. 40, the left foot heel down position occurs at point 1624, while the left foot heel up position occurs at point 1628. Between these two points 1624, 1628, force plates 2C, 3A, 3B, 4A, 4B of the force plate array 1502' (see FIG. 39) are experiencing a load. In FIG. 40, the double stance phase 1630 of the gait cycle (i.e., when both feet of the subject are in contact with the force plate array 1502') occurs between points 1624 and 1626. By identifying the double stance phase of the gait cycle, the data acquisition and processing device 1504 determines that the vertical forces occurring prior to the double stance phase in time are associated with the first of the subject's two feet (i.e., between points 1620 and 1622 in FIG. 40), and further determines that the vertical forces occurring after the double stance phase in time are associated with the second of the subject's two feet (i.e., between points 1626 and 1628 in FIG. 40), because only a single foot of the subject is in contact with the force plate array surface during these two time increments. As explained above, the particular foot of the subject that is applying the forces before, and after the double stance phase of the gait cycle may be determined by comparing the x-coordinates of the load centers of pressure.

In addition, the data acquisition and processing device 1504 may be further specially programmed to compute, by using the output data, a summation of forces applied to measurement surfaces of respective ones of the plurality of measurement assemblies 1506' as each of the plurality of measurement assemblies 1506' are activated so as to determine whether the load that is being applied to the particular one of the plurality of measurement assemblies 1506' is being applied by only a single foot of the subject or both feet of the subject. For example, referring again to FIG. 40, if the force curve associated with force plate 2C is added to the force curve associated with force plate 3B, the data acquisition and processing device 1504 determines that forces applied to these two force plates 2C, 3B must have been generated by two separate feet of the subject, rather only a single foot of the subject, because the summation of the peak forces applied to force plates 2C, 3B greatly exceeds the weight of the subject (i.e., when the force curves associated with the force plates 2C, 3B are added together, their peak summation greatly exceeds the value of the total force curve 1606 in FIG. 40).

Figure 41:
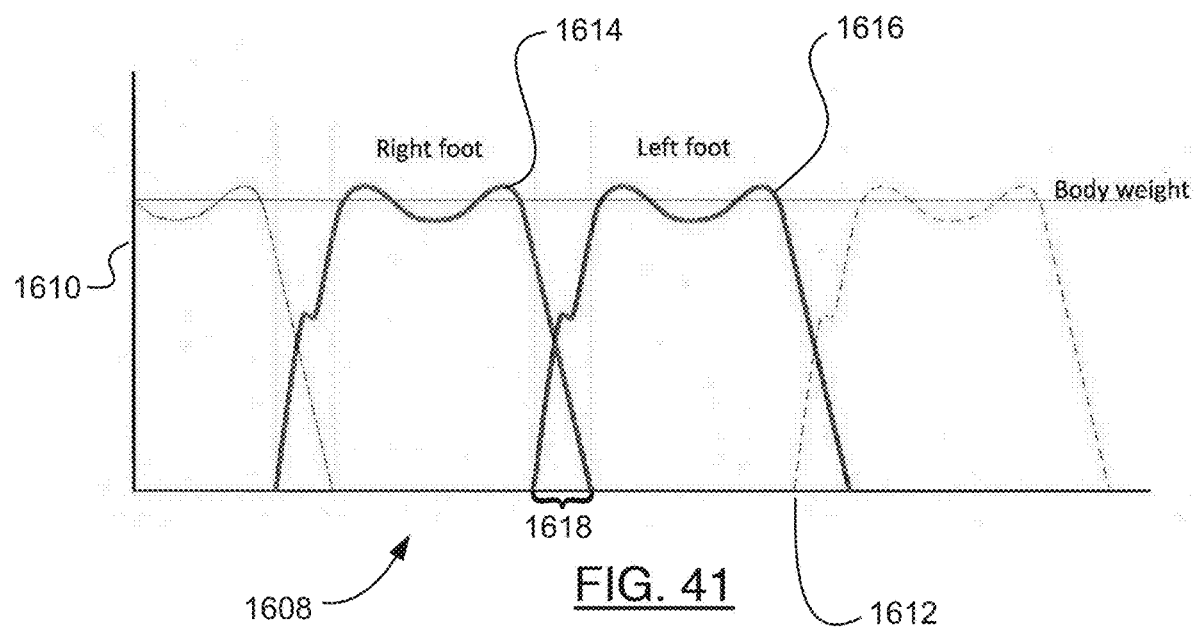
FIG. 41 is another graph illustrating a magnitude of a vertical force being separately applied by a right foot and a left foot of a subject during a gait cycle.

Now, turning to FIG. 41, a graphical illustration of force curves corresponding to the right and left foot of the subject will be explained. In FIG. 41, the separate vertical forces ($F_t$) being applied by the subject's feet are plotted as function of time. As such, the y-axis 1610 of the graph 1608 of FIG. 41 corresponds to the vertical force, and the x-axis 1612 of the graph 1608 of FIG. 41 corresponds to time (e.g., in seconds). The curve 1614 in FIG. 41 illustrates the vertical force generated by the right foot of the subject on the force plate array, while the curve 1616 in FIG. 41 illustrates the vertical force generated by the left foot of the subject on the force plate array (e.g., the force plate array of FIG. 39). Similar to that described above for FIG. 40, the double stance phase of the gait cycle (i.e., when both feet of the subject are in contact with the force plate array 1502') occurs in the region 1618 of FIG. 41.

It is apparent from the above detailed description that the measurement and testing systems 1500 with the force plate arrays 1502, 1502', 1502" significantly advance the field of human balance assessment and human gait analysis. For example, the measurement and testing systems 1500 with the force plate arrays 1502, 1502', 1502" described herein utilize a large measurement surface area that enables the movement of the individual legs of the subject disposed thereon to be separately analyzed. As another example, the measurement and testing systems 1500 with the force plate arrays 1502, 1502', 1502" described herein include a data acquisition and processing device that is specially programmed to determine the movement generated by each of the legs separately. As yet another example, the measurement and testing systems 1500 with the force plate arrays 1502, 1502', 1502" described herein have a data acquisition and processing device which is specially programmed to create one or more virtual measurement assemblies from one or more subsets of a plurality of measurement assemblies. As still another example, the measurement and testing systems 1500 with the force plate arrays 1502, 1502', 1502" described herein are capable of accurately producing force and moment output data for situations where the subject's feet are overlapping more than one of the separate measurement surfaces forming the overall large measurement surface area. As yet another example, the measurement and testing systems 1500 with the force plate arrays 1502, 1502', 1502" described herein may comprise a plurality of measurement assemblies that are dimensioned and sized to prevent both feet of the subject from landing on the same one of the separate measurement surfaces comprising the array, thereby enabling the separate analysis of the movement generated by each of the two legs to be accurately performed.

Another illustrative embodiment of a measurement and testing system in the form of a force measurement system is illustrated in FIGS. 44-49. Initially, referring to the perspective view of FIG. 49, it can be seen that, in the illustrative embodiment, the force measurement system may comprise a force plate array 1730 formed by a plurality of force plate modules 1700 connected to one another. Similar to that described above for the force plate system 1500, the force plate modules 1700 of the force plate array 1730 may be operatively coupled to a data acquisition and processing device 1740 (i.e., a computing device 1740) by virtue of a plurality of electrical cables 1734 (see e.g., FIGS. 50 and 51). In one or more embodiments, the electrical cables 1734 are used for data transmission, as well as for providing power to the force plate modules 1700 of the force plate array 1730. Preferably, the electrical cables 1734 contain a plurality of electrical wires bundled together, with at least one wire being used for power and at least another wire being used for transmitting data. The bundling of the power and data transmission wires into a single electrical cable 1734 to each force plate module 1700 advantageously creates a simpler and more efficient design. In addition, it enhances the safety of the testing environment when human subjects are being tested on the force plate array 1730. However, it is to be understood that the force plate array 1730 can be operatively coupled to the data acquisition and processing device 1740 using other signal transmission means, such as a wireless data transmission system. If a wireless data transmission system is employed, it is preferable to provide the force plate array 1730 with a separate power supply in the form of an internal power supply or a dedicated external power supply.

Figure 44:
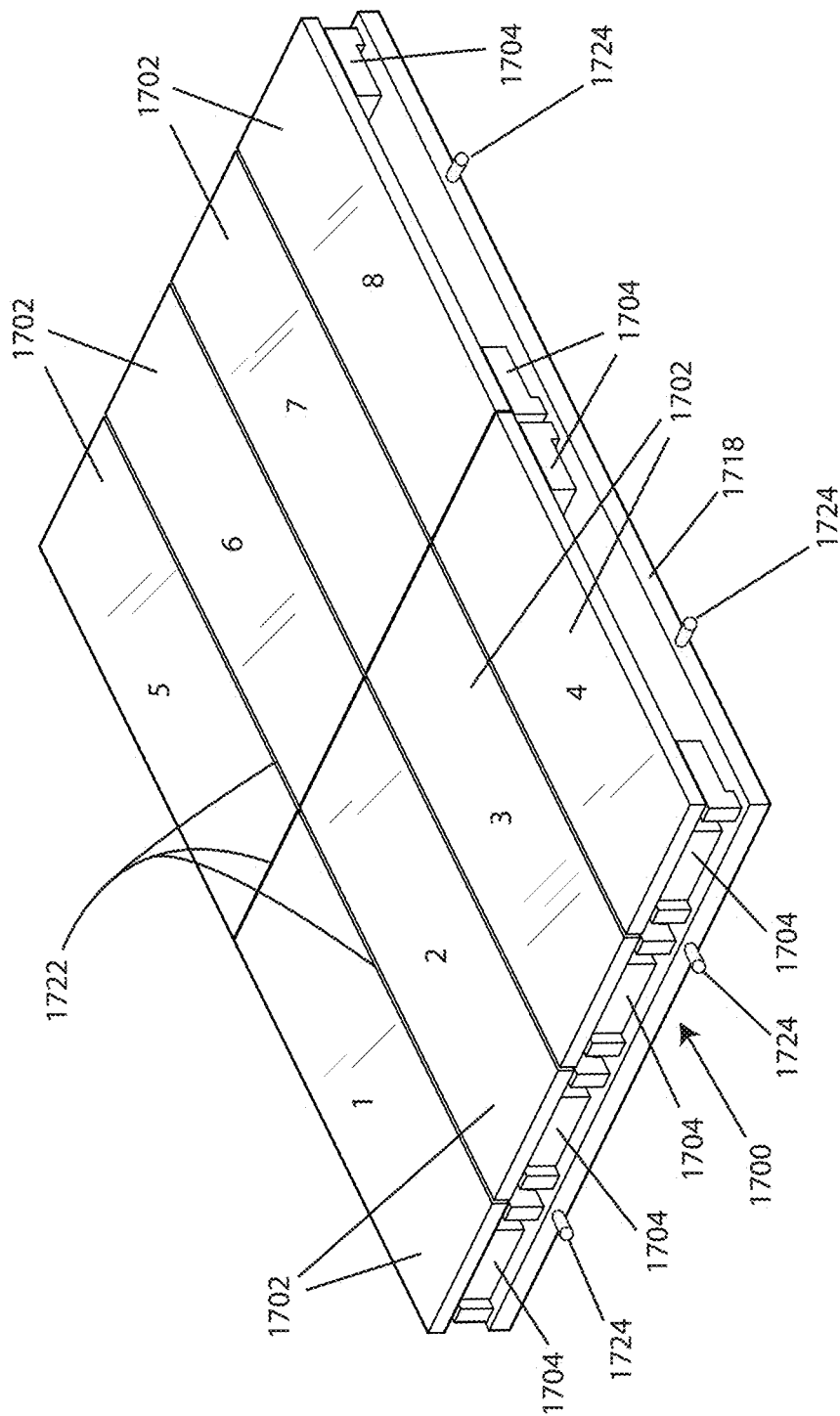
FIG. 44 is a perspective view of a force plate module of a force measurement system, according to yet another embodiment of the invention.
Figure 45:
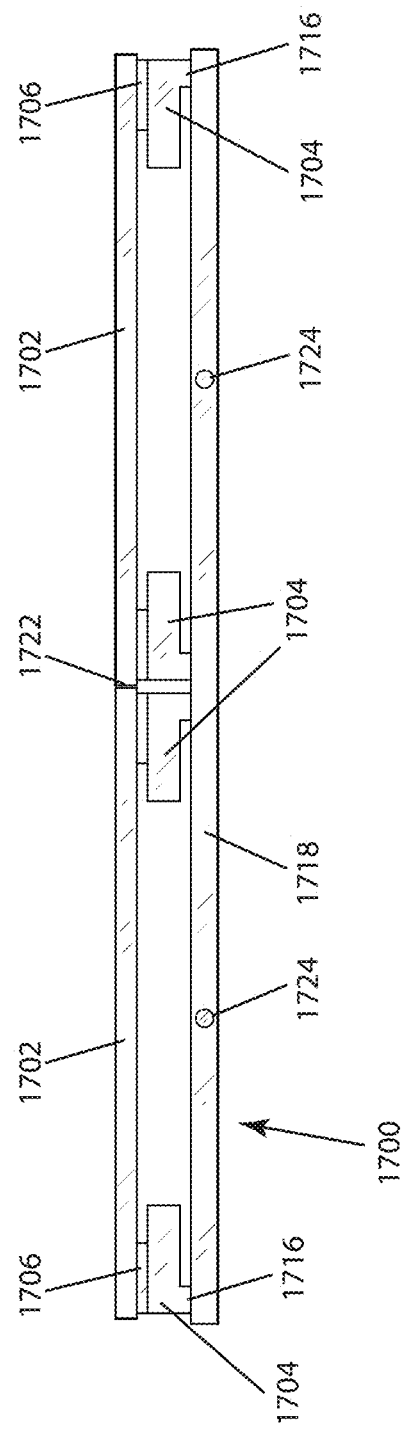
FIG. 45 is a side elevational view of the force plate module of FIG. 44.
Figure 46:
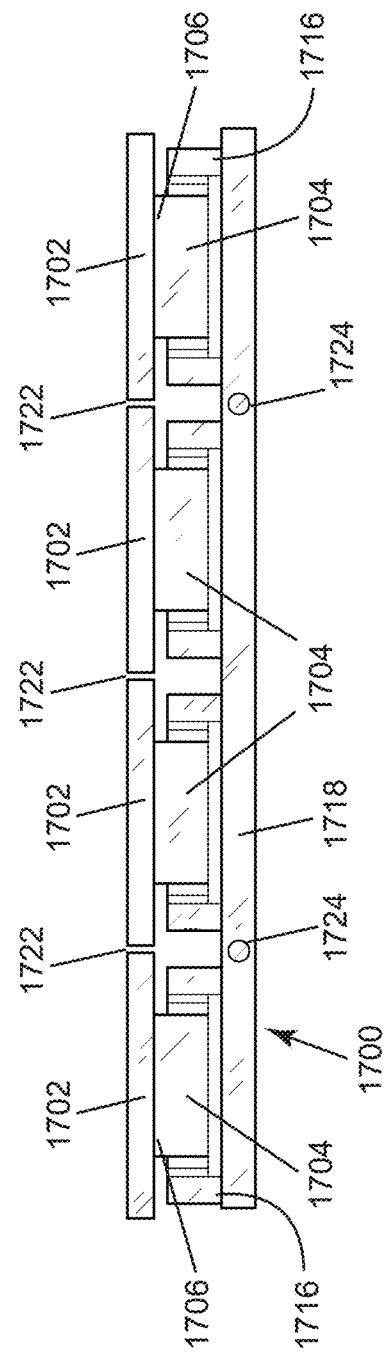
FIG. 46 is an end elevational view of the force plate module of FIG. 44.
Figure 47:
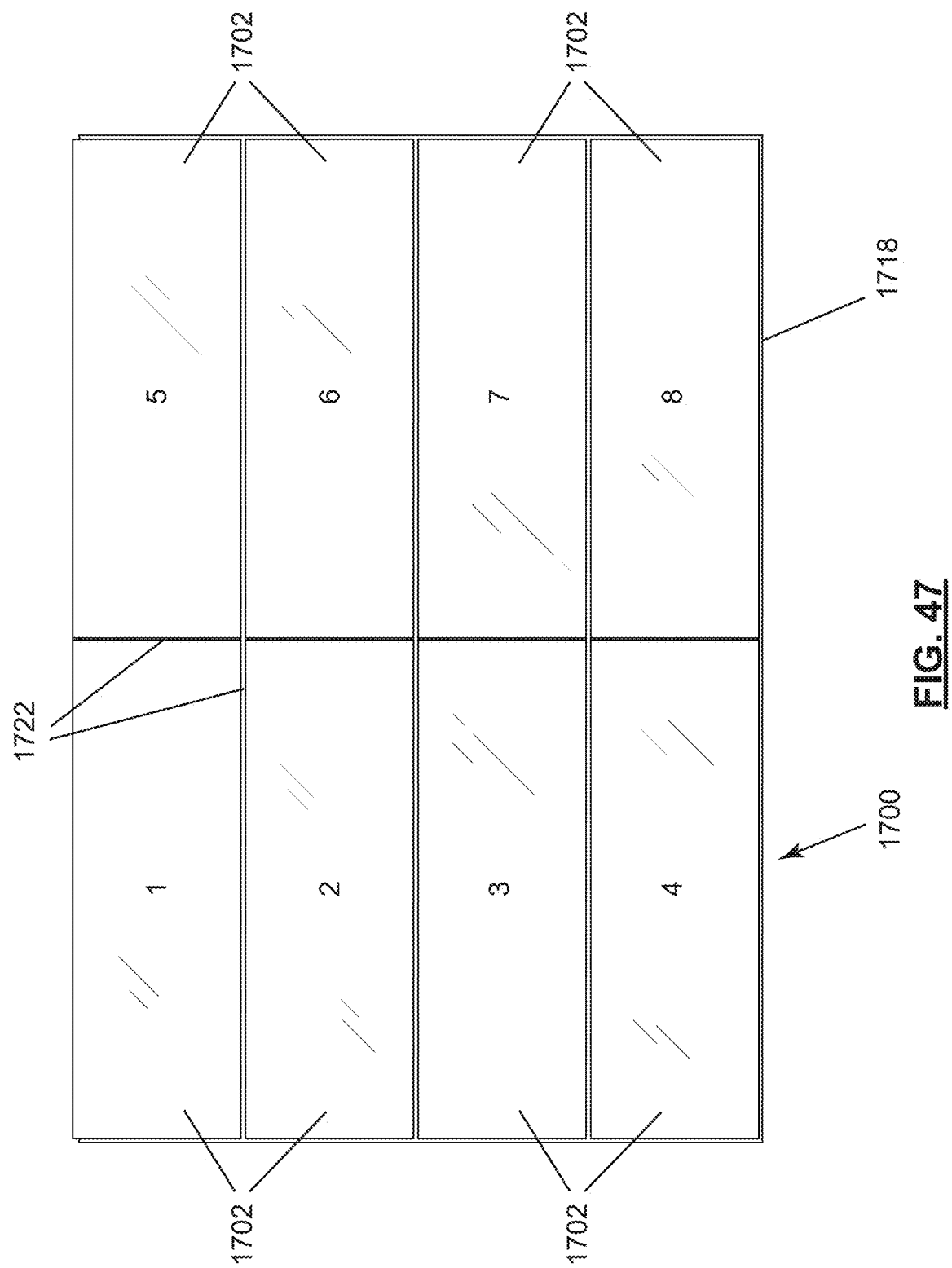
FIG. 47 is a top plan view of the force plate module of FIG. 44.
Figure 48:
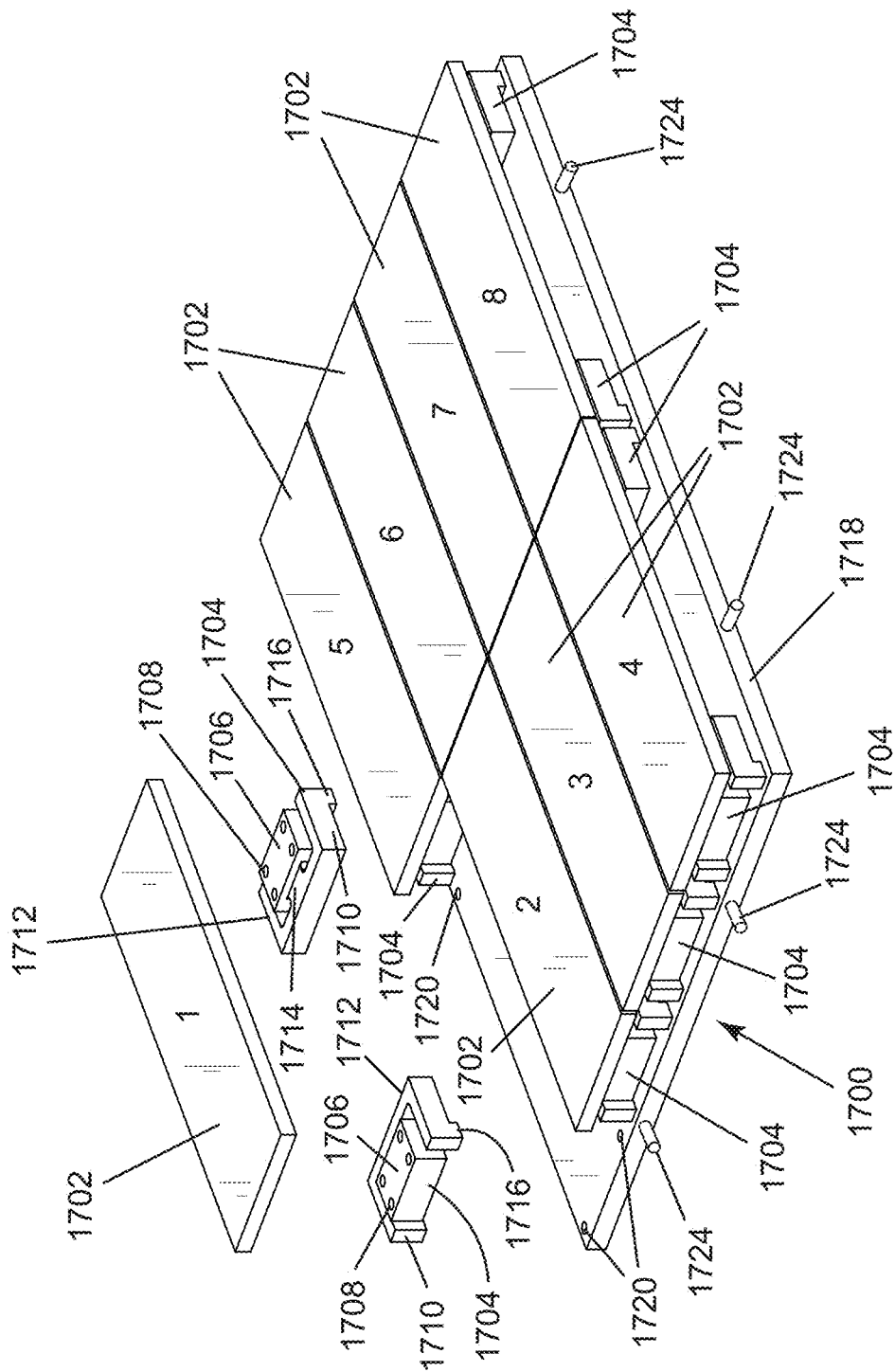
FIG. 48 is a partially exploded perspective view of the force plate module of FIG. 44.

Now, turning to FIGS. 44-48, it can be seen that, in the illustrative embodiment, each of the force plate modules 1700 of the force plate array 1730 includes a plurality of force plate assemblies in the form of force plates that are disposed adjacent to one another, and each being separated by a narrow gap 1722 (see FIG. 44). As depicted in FIGS. 44-45, the plurality of force plate assemblies of the force plate module 1700 are supported on a common base component 1718, which is in the form of a continuous base plate that extends underneath all of the module force plate assemblies in the illustrated embodiment. Also, in the illustrated embodiment, each of the force plate assemblies includes a top plate component 1702 having an upper surface, the upper surface of each top plate component 1702 forming a force measurement surface for receiving at least one portion of a body of a subject (e.g., a foot/leg of a subject). In addition, each of the illustrated module force plate assemblies is provided with a plurality of force transducers 1704 (e.g., a pair of transducer beams) disposed underneath, and supporting the top plate component 1702. The force transducers of the force plate assemblies are configured to sense one or more measured quantities and output one or more signals that are representative of the one or more measured quantities (i.e., force and/or moments). In one or more embodiments, a subject stands in an upright position on the force plate array 1730 in FIG. 49, and each foot of the subject is placed on one or more top surfaces of the force plate modules 1700 in the force plate array 1730. In FIGS. 44, 47, and 48, each force plate assembly of the force plate module 1700 is identified by a corresponding identification number (i.e., force plate no. 1, 2, 3, 4, 5, 6, 7, and 8).

With reference primarily to FIG. 48 of the illustrative embodiment, the force transducers 1704 of each force plate assembly of the force plate module 1700 will be described in detail. As shown in the exploded view of FIG. 48, each of the pair of force transducers 1704 is disposed proximate to one of the opposite longitudinal ends of the top plate component 1702 of each force plate assembly. Each of the force transducers 1704 generally comprises a central rectangular body portion 1706 with an upper standoff portion, first and second L-shaped transducer beam portions 1710, 1712 that wrap around a portion of the outer periphery of the rectangular body portion 1706, and a beam connector portion 1714 that connects each of the first and second L-shaped transducer beam portions 1710, 1712 to a common side of the rectangular body portion 1706. As shown in FIG. 48, each of the first and second L-shaped transducer beam portions 1710, 1712 is oppositely disposed with respect to one another, and, except for the connector portion 1714, each of the first and second L-shaped transducer beam portions 1710, 1712 is spaced apart from the outer side surfaces of the rectangular body portion 1706 by a continuous narrow gap. Each of the L-shaped transducer beam portions 1710, 1712 comprises two transducer beam sections perpendicularly disposed relative to one another, namely a proximal beam section connected to the connector portion 1714 and a distal beam section with a lower standoff portion 1716. The upper standoff portion (i.e., the raised top surface) of rectangular body portion 1706 elevates the top plate component 1702 above the top surfaces of the L-shaped transducer beam portions 1710, 1712 so as to create a gap between the top surfaces of the L-shaped transducer beam portions 1710, 1712 and the bottom surface of the top plate component 1702, whereas the lower standoff portions 1716 of the distal beam sections elevate the bottom surfaces of the L-shaped transducer beam portions 1710, 1712 above the top surface of the base plate component 1718 so as to create a gap between the top surface of the base plate component 1718 and the bottom surfaces of the L-shaped transducer beam portions 1710, 1712. As such, in the illustrative embodiment, the structural components 1702, 1718 to which the force transducers 1704 are mounted are connected only to the upper standoff portion of the rectangular body portion 1706 and the lower standoff portions 1716 of the distal beam sections so as to ensure that the total load applied to the force transducers 1704 is transmitted through the transducer beam portions 1710, 1712. The compact structural configuration of the force transducers 1704 enables the force transducers 1704 to be effectively utilized in the force plate module 1700, which comprises the plurality of small force plate assemblies (i.e., force plate nos. 1, 2, 3, 4, 5, 6, 7, and 8).

In the illustrative embodiment, each of the L-shaped transducer beam portions 1710, 1712 may comprises a plurality of strain gages for detecting the deformation in the beam sections of the L-shaped transducer beam portions 1710, 1712 resulting from the applied load. For example, in the illustrative embodiment, the force transducers 1704 of each force plate assembly of the force plate module 1700 may be sensitive to the vertical force ($F_z$) and the moments in the x and y directions ($M_x$, $M_y$). Alternatively, the force transducers 1704 of each force plate assembly of the force plate module 1700 may be sensitive to all six (6) force and moment components ($F_x$, $F_y$, $F_z$, $M_x$, $M_y$, $M_z$). Because the manner in which the forces and/or moments are determined by the data acquisition and processing device 1740 from the output signals of the force transducers 1704 is generally the same as that described above with regard to FIG. 3, an explanation of this functionality does not need to repeated in conjunction with this embodiment.

Similar to the data acquisition/data processing device 104 described above with reference to FIG. 2, the data acquisition and processing device 1740 (i.e., computing device 1740) may comprise a microprocessor for processing data from the force plate modules 1700, memory (e.g., random access memory or RAM) for storing data during the processing thereof, and data storage device(s), such as one or more hard drives, compact disk drives, floppy disk drives, flash drives, or any combination thereof. Also, the data acquisition and processing device 1740 may comprise user input devices in the form of a keyboard, mouse, and touchpad or touchscreen.

Turning again to the partially exploded perspective view of FIG. 48, it can be seen that the rectangular body portion 1706 of each force transducer 1704 is provided with a plurality of mounting apertures 1708 disposed therethrough (i.e., four (4) mounting apertures 1708 arranged in a rectangular configuration) for receiving fasteners (e.g., mounting screws) that secure the force transducer 1704 to the top plate component 1702. Also, as shown in FIG. 48, it can be seen that the base plate component 1718 is provided with a plurality of mounting apertures 1720 disposed therethrough (i.e., four (4) mounting apertures 1720 corresponding to each force plate assembly) for receiving fasteners (e.g., mounting screws) that secure the lower standoff portions 1716 of the force transducers 1704 to the base plate component 1718.

Figure 49:
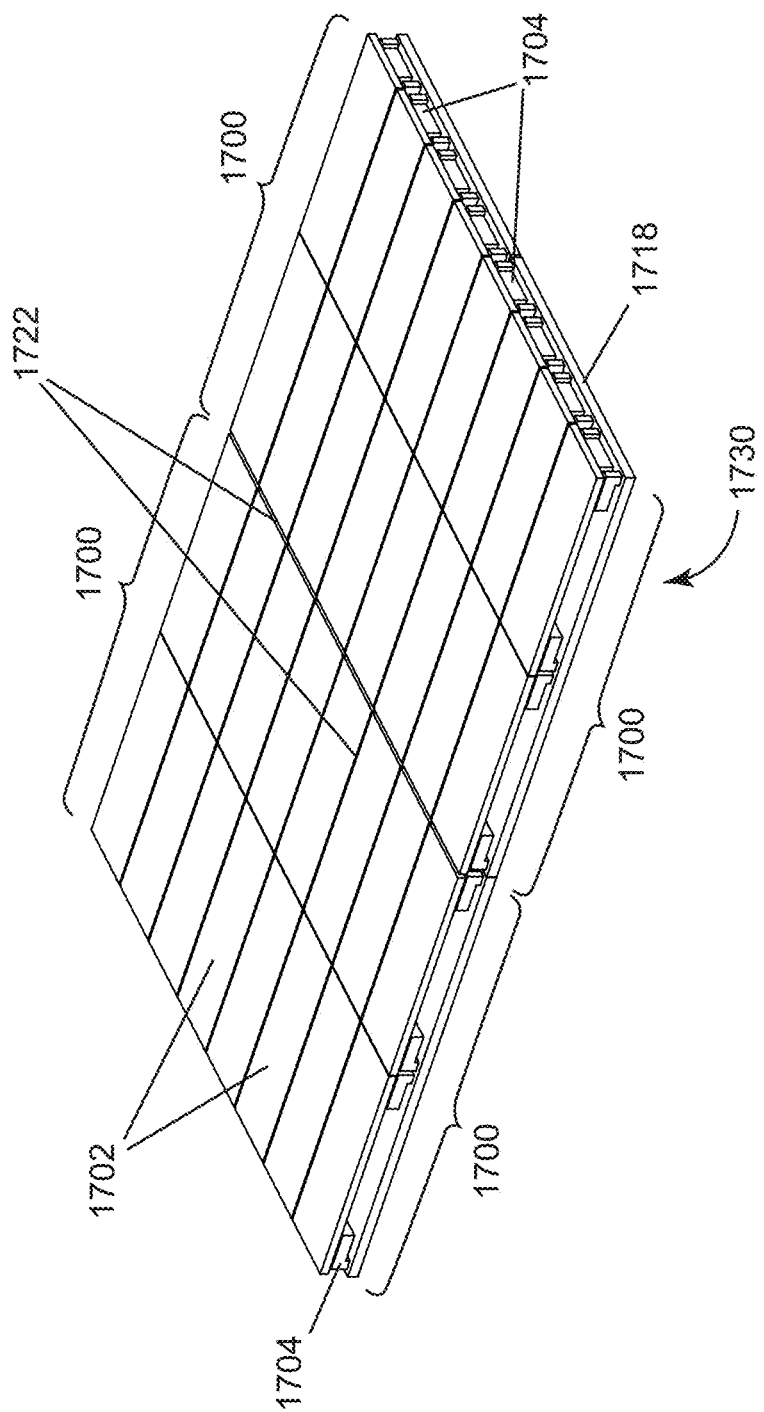
FIG. 49 is a perspective view of a force measurement system comprising a plurality of force plate modules of FIG. 44 connected together.

With combined reference to FIGS. 44-46 and 48, it can be seen that, in the illustrative embodiment, the force plate module 1700 comprises a plurality of alignment/securement devices 1724 (i.e., combination alignment and latching devices) for attaching and aligning the force plate module 1700 to the one or more additional force plate modules 1700 in the force plate array 1730 (as depicted in FIG. 49). That is, each force plate module 1700 in the force plate array 1730 of FIG. 49 is provided with a plurality of alignment/securement devices 1724 to connect the force plate module 1700 to one or more adjacent force plate modules 1700 in the modular force plate array 1730. For example, as best shown in the perspective views of FIGS. 44 and 48, a pair of spaced-apart alignment/securement devices 1724 is provided on two (2) perpendicularly disposed sides of the base plate component 1718. In the illustrative embodiment of FIGS. 44-46 and 48, each of the plurality of alignment/securement devices 1724 may comprise a cylindrical pin-like member (or cylindrical boss member) projecting outward from a side of the base plate component 1718. Each of the pin-like alignment/securement devices 1724 may be received within a corresponding cylindrical bore or recess in an adjacent force plate module 1700 of the force plate array 1730. As such, the adjacent force plate modules 1700 of the force plate array 1730 are capable of being both aligned with one another, and fixed relative to one another, by the mating engagement between the pin-like alignment/securement devices 1724 and their corresponding cylindrical bores or recesses. In the illustrative embodiment, the alignment/securement devices 1724 are configured to be removably engaged and disengaged without the use of any tools (e.g., no tools are required to engage the pin-like member with its corresponding cylindrical bore or recess). For example, the pin-like member may be spring-loaded so that it snaps into place within its corresponding cylindrical bore or recess. Also, in the illustrative embodiment, the alignment/securement devices 1724 of each force plate module 1700 may be top accessible so that a person disposed on the top surface of the force plate module 1700 may engage and disengage the pin-like members from their corresponding cylindrical bores or recesses without being required to access the bottom or side of the force plate module 1700. The top accessibility of the alignment/securement devices 1724 greatly facilitates the installation of the force plate modules 1700 forming the force plate array 1730 because the sides and bottom of the force plate modules 1700 may be generally inaccessible in typical force plate array installations.

Advantageously, the modular configuration of the force measurement system allows the components of the individual force plate modules 1700 to be completely assembled at the factory in a closely-controlled manner, and then the individual force plate modules 1700 to be easily secured to one another on site using the alignment/securement devices 1724 so as to form the overall force plate array 1730. For example, in one or more embodiments, the force plate modules 1700 may be assembled in an array on mounting surface, such as the floor of a building or a metal mounting plate. The modular construction of the force plate system allows the force plate array 1730 to be easily adapted to specific room configurations in a building (i.e., the individual force plate modules 1700 may be fastened together so as to form a myriad of different force plate array geometries.

Figure 50:
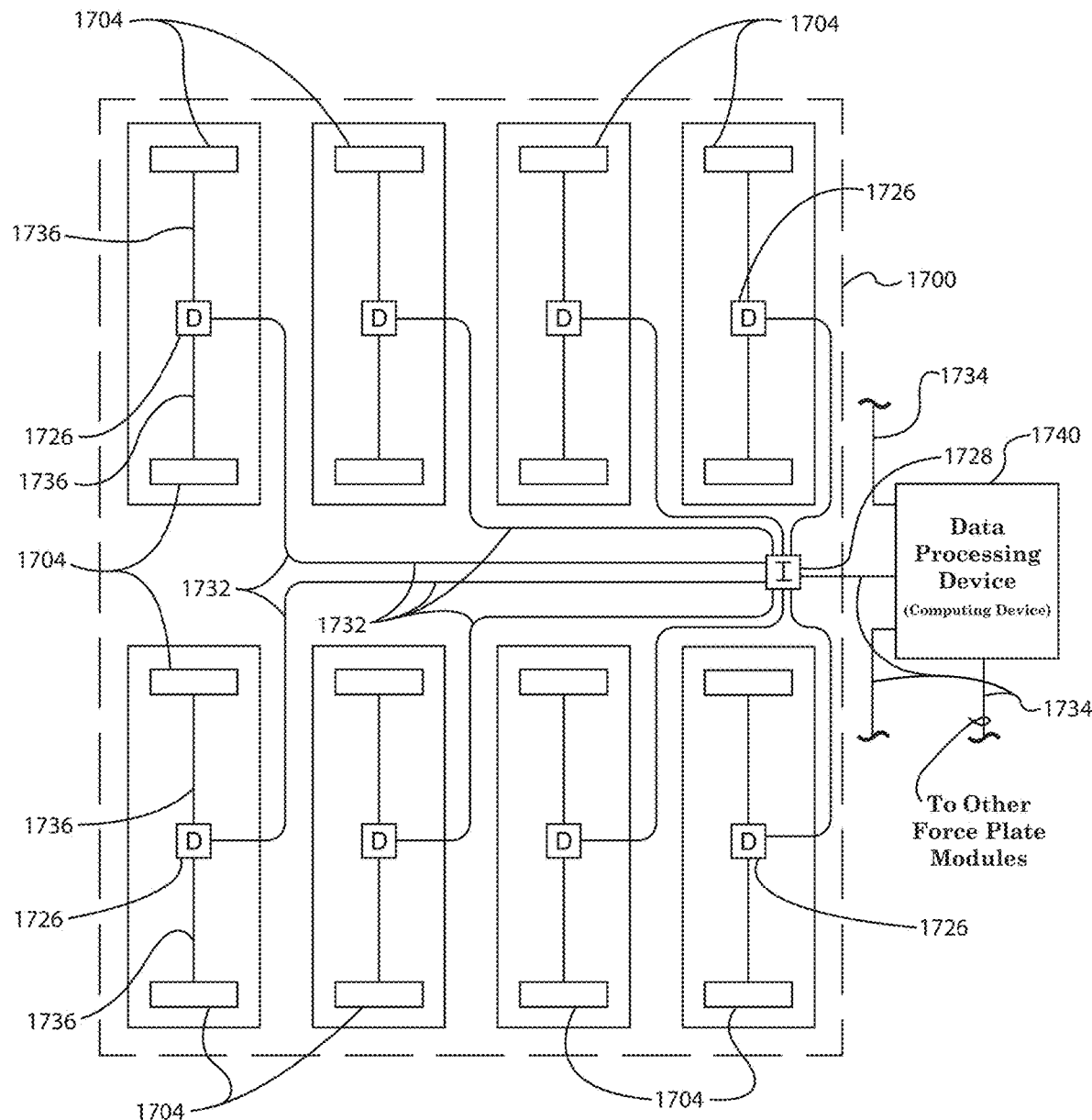
FIG. 50 is a schematic diagram illustrating one configuration for the electrical subassembly of the force plate module of FIG. 44, according to one embodiment of the invention.
Figure 51:
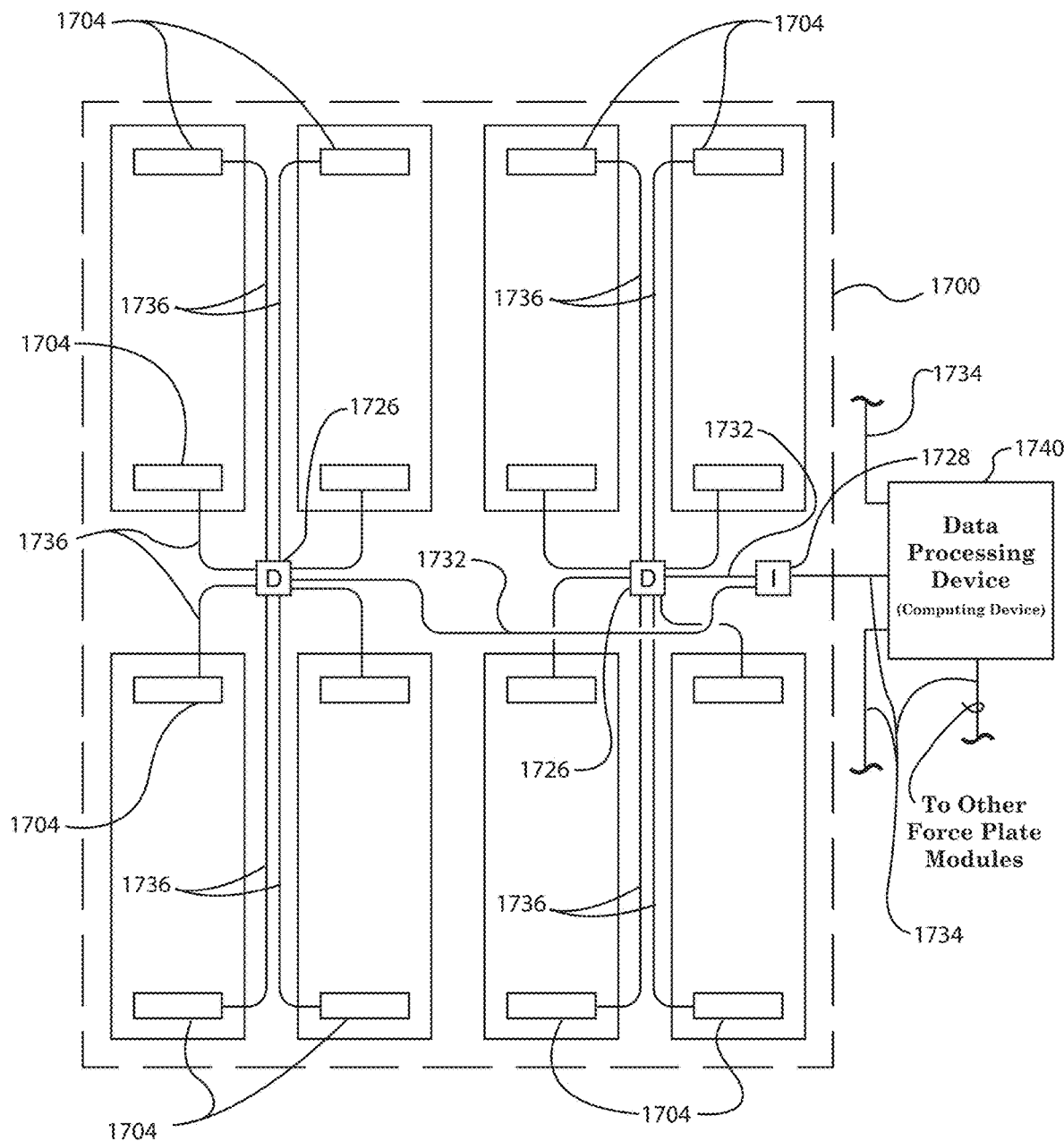
FIG. 51 is another schematic diagram illustrating an alternative configuration for the electrical subassembly of the force plate module of FIG. 44, according to another embodiment of the invention.

Next, referring to FIGS. 50 and 51, illustrative embodiments of the electrical components and wiring of the force plate module 1700 will be explained. Initially, as shown in FIG. 50, it can be seen that, in this first illustrative embodiment, each of the force plate assemblies may comprise a dedicated digitizer and signal conditioner 1726 that is electrically coupled to each of the force transducers 1704 of the respective force plate assembly by electrical transducer wiring 1736. Each digitizer and signal conditioner 1726 converts the analog voltage signals from the transducers 1704 of its respective force plate assembly into digital voltage signals, and may also perform other functions on the signals as well, such as amplification, filtering, etc. Referring again to FIG. 50, it can be seen that each force plate digitizer and signal conditioner 1726 is electrically coupled to an electrical interface 1728 of the force plate module 1700 by electrical wiring 1732 (e.g., by Universal Serial Bus (USB) cables). The electrical interface 1728 of the force plate module 1700 may comprise one or more electrical ports for receiving one or more respective wiring plug connectors of electrical cables that transfer data and/or power to, and from, the force plate module 1700. For example, as shown in FIG. 50, the electrical interface 1728 of the force plate module 1700 is electrically coupled to the data acquisition and processing device 1740 by the electrical cable 1734 so that the signals from the force transducers 1704 of the force plate assemblies may be converted into output loads (i.e., into forces and/or moments). In FIG. 50, it can be seen that a plurality of other force plate modules 1700 are electrically connected to the data acquisition and processing device 1740 by electrical cables 1734 so that load data may be generated from these force plate modules 1700 as well.

In one or more embodiments, the electrical interface 1728 of the force plate module 1700 may comprise a plurality of electrical ports, which include a Universal Serial Bus (USB) port, an Ethernet port, a power over Ethernet (PoE) port, and an additional power input port.

Turning to FIG. 51, it can be seen that the second illustrative embodiment depicted in this figure is similar in many respects to the first illustrative embodiment of FIG. 50 described above. However, unlike the embodiment of FIG. 50, each force plate assembly of the force plate module 1700 is not provided with a dedicated digitizer and signal conditioner 1726. Rather, as shown in FIG. 51, the force transducers 1704 of the four (4) force plate assemblies of the force plate module 1700 are electrically coupled to a first digitizer and signal conditioner 1726 by electrical transducer wiring 1736, and then the force transducers 1704 of the other four (4) force plate assemblies of the force plate module 1700 are electrically coupled to a second digitizer and signal conditioner 1726 by electrical transducer wiring 1736. Then, each of the two (2) digitizers and signal conditioners 1726 are electrically coupled to the electrical interface 1728 of the force plate module 1700 by respective electrical cables 1732 (e.g., by Universal Serial Bus (USB) cables). Finally, as described above for the embodiment of FIG. 50, the electrical interface 1728 of the force plate module 1700 is electrically coupled to the data acquisition and processing device 1740 by the electrical cable 1734 so that the signals from the force transducers 1704 of the force plate assemblies may be converted into output loads (i.e., into forces and/or moments). And, as explained above for FIG. 50, it can be seen that a plurality of other force plate modules 1700 are electrically connected to the data acquisition and processing device 1740 so that load data may be generated from these force plate modules 1700 as well.

Figure 52A:
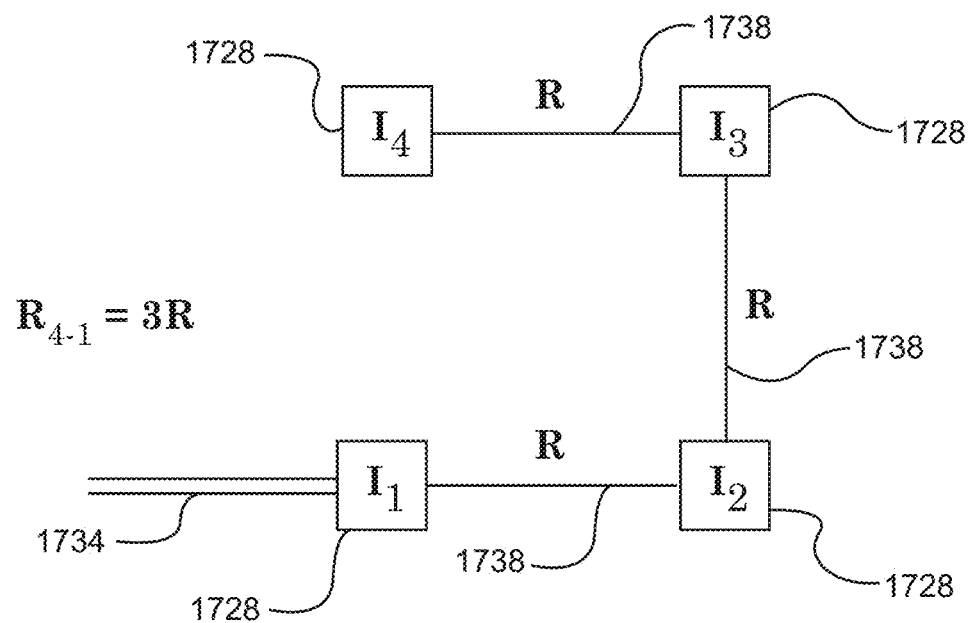
FIG. 52A is a schematic diagram illustrating a series power connection configuration for electrically coupling a plurality of force plate modules to one another, according to one embodiment of the invention.
Figure 52B:
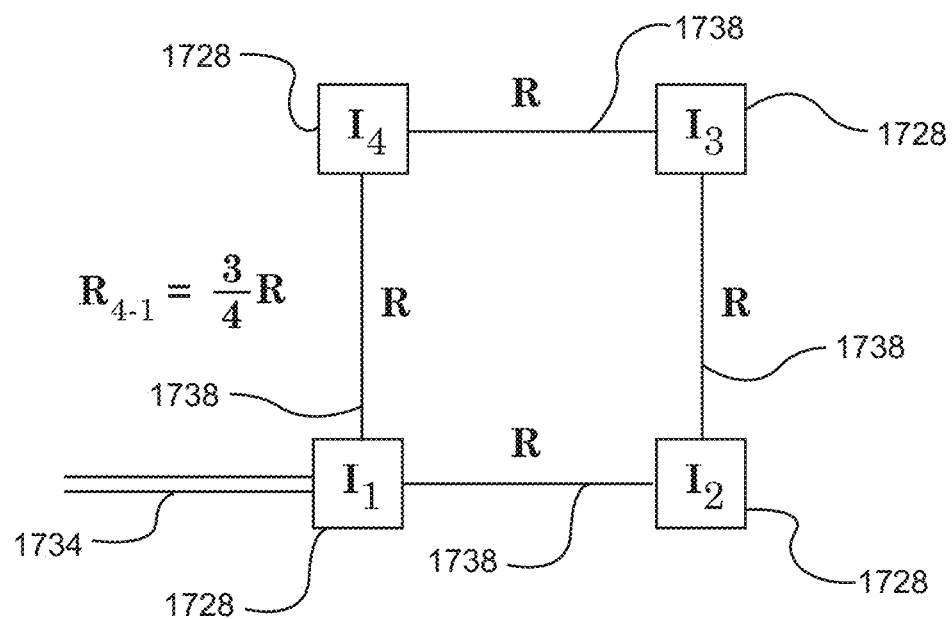
FIG. 52B is a schematic diagram illustrating an alternative power connection configuration for electrically coupling a plurality of force plate modules to one another, according to another embodiment of the invention.

In one or more embodiments, one or more of the plurality of force plate modules 1700 of the force plate array 1730 may comprise a redundant power connection to a power source (e.g., a building wall receptacle) to provide a backup power supply, reduce power transmission losses in the force measurement system, and/or increase the power delivery capacity of the force measurement system. In particular, in the illustrative embodiment of FIG. 52B, a plurality of force plate modules 1700 may comprise power connections to two or more other force plate modules 1700 so as to provide an auxiliary transmission path for electrical power and/or to reduce power transmission losses in the force measurement system. Initially, referring to FIG. 52A, it can be seen that the electrical interfaces 1728 of the four (4) force plate modules 1700 are connected in series with one another by electrical power wiring 1738. As such, in the wiring configuration of FIG. 52A, the equivalent resistance for the electrical current path between electrical interface $I_1$ and electrical interface $I_4$ is $R_{4-1}=3R$ (i.e., between nodes 1 and 4). Although, in the alternative redundant wiring scheme of FIG. 52B, the equivalent resistance for the electrical current path between electrical interface $I_1$ and electrical interface $I_4$ is reduced to $R_{4-1}=0.75R$ (i.e., between nodes 1 and 4). Thus, the addition of the electrical power wiring 1738 directly connecting electrical interface $I_1$ to electrical interface $I_4$ substantially reduces the equivalent resistance $R_{4-1}$, thereby substantially reducing power transmission losses in the force measurement system. Moreover, the addition of the electrical power wiring 1738 directly connecting electrical interface $I_1$ to electrical interface $I_4$ also provides a redundant power connection for the system so as to compensate for the failure of one or more of the cables connecting the electrical interfaces 1728 of two force plate modules 1700 with one another (e.g., in FIG. 52B, if the cable 1738 connecting the electrical interface $I_2$ to the electrical interface $I_3$ fails, power is still capable of being supplied to electrical interfaces $I_3$ and $I_4$ by the cable extending between the electrical interface $I_1$ and electrical interface $I_4$).

Figure 53A:
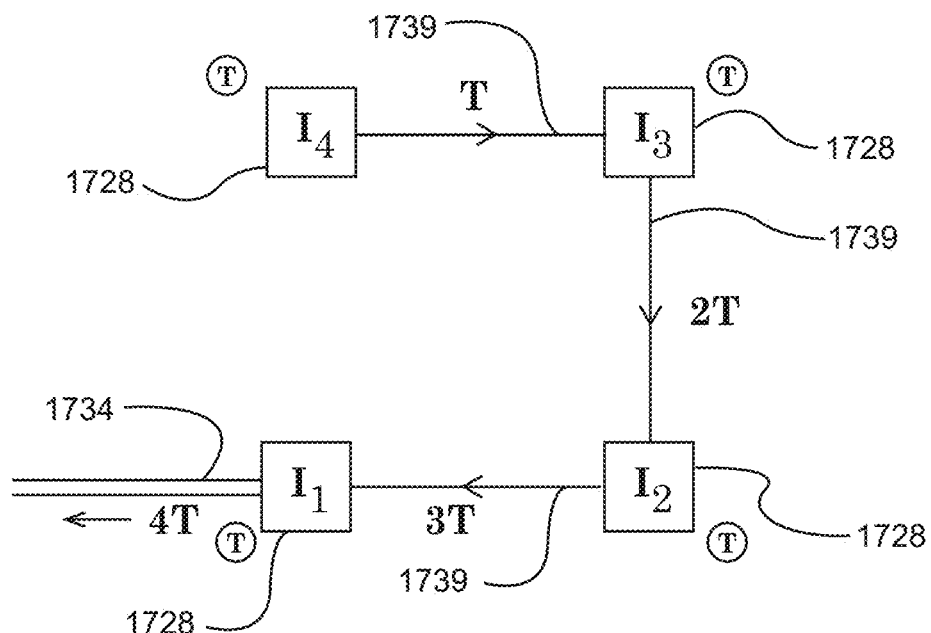
FIG. 53A is a schematic diagram illustrating a series data connection configuration for electrically coupling a plurality of force plate modules to one another, according to one embodiment of the invention.
Figure 53B:
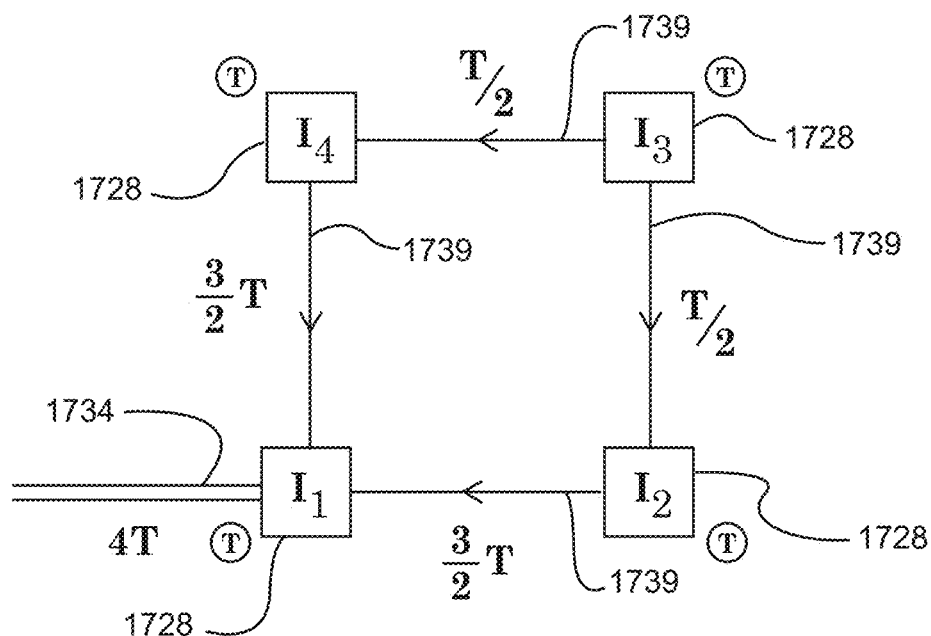
FIG. 53B is a schematic diagram illustrating an alternative data connection configuration for electrically coupling a plurality of force plate modules to one another, according to another embodiment of the invention.

Also, in one or more embodiments, one or more of the plurality of force plate modules 1700 of the force plate array 1730 may comprise a redundant data connection to the data acquisition and processing device 1740 to provide an auxiliary data transmission path and/or to increase a data transfer rate in the force measurement system. In particular, in the illustrative embodiment of FIG. 53B, a plurality of force plate modules 1700 may comprise data connections to two or more other force plate modules 1700 so as to provide an auxiliary data transmission path and/or to increase a data transfer rate in the force measurement system. Initially, referring to FIG. 53A, it can be seen that the electrical interfaces 1728 of the four (4) force plate modules 1700 are connected in series with one another by data transmission wiring 1739. As such, because the electrical interfaces 1728 of the force plate modules 1700 in FIG. 53A are electrically coupled to one another in series, the data from the four (4) force plate modules 1700 are combined with one another such that the data transmission wiring back to the data acquisition and processing device 1740 has an overall data transmission load of 4 T. In the wiring configuration of FIG. 53A, the data transmission load from electrical interface $I_2$ to electrical interface $I_1$ is 3 T. Although, in the alternative redundant wiring scheme of FIG. 53B, the data transmission load from electrical interface $I_2$ to electrical interface $I_1$ is reduced to 1.5 T. In FIG. 53B, the remaining 1.5 T of the data transmission load is transmitted by the data transmission wiring 1739 extending between electrical interface $I_4$ and $I_1$. Thus, the addition of the data transmission wiring 1739 directly connecting electrical interface $I_4$ to electrical interface $I_1$ reduces the maximum data transmission load between any two of the electrical interfaces in FIG. 53B down to 1.5 T, thereby allowing a smaller wire size to be used between electrical interface $I_3$ and $I_2$, and between electrical interface $I_2$ and $I_1$ (multiple smaller data transmission wires are more cost effective for the system than a single larger data transmission wire). Moreover, the addition of the data transmission wiring 1739 directly connecting electrical interface $I_4$ to electrical interface $I_1$ also provides a redundant data connection for the system so as compensate for the failure of one or more of the data cables connecting the electrical interfaces 1728 of two force plate modules 1700 with one another (e.g., in FIG. 53B, if the cable 1739 connecting the electrical interface $I_3$ to the electrical interface $I_2$ fails, data is still capable of being transmitted from electrical interfaces $I_3$ and $I_4$ by the data cable 1739 extending between the electrical interface $I_4$ and electrical interface $I_1$.

In one or more embodiments, electrical power may be provided to one or more of the plurality of force plate modules 1700 in the force plate array 1730 using a power over Ethernet connection. As such, a single cable or wire may be used both for plate module power and data transmission. Further, in one or more embodiments, both redundant data connections and redundant power connections may be utilized between the force plate modules 1700 so as to provide backup connections in the case of either a power failure or a data transmission failure (e.g., resulting from an inoperative connection to a particular force plate module 1700).

In one or more alternative embodiments, one or more of the plurality of force plate modules 1700 in the force plate array 1730 may comprise a wireless data interface and/or a wireless power interface so that electrical cables are not required for power and data transmission to the data acquisition and processing device 1740 (e.g., the electrical interfaces 1726 may include a wireless-type interface). In such a wireless arrangement, the same redundant power and data configurations described above for the wired connections may also be incorporated in the alternative wireless power and data configurations.

As discussed above with regard to FIG. 53A, the electrical interfaces 1728 of the force plate modules 1700 may be electrically coupled to one another in series so that the data from a preceding force plate module 1700 is combined with data from one or more subsequent force plate modules 1700 in the force plate array 1730 (i.e., data combination on the "fly"). For example, the data from the plate assemblies of a plurality of force plate modules 1700 may be combined in one or more of the following ways: (i) data combined in the order received without fallback, (ii) the data of the oldest field is dropped first, (iii) additional data is added to an overflow field when the normal data fields are completely filled, and (iv) the lowest load is dropped by some metric. For data combination scheme (i) above, fields corresponding to particular load locations (e.g., force plate assemblies on force plate modules 1700) are consecutively filled by the force plate modules 1700 in series until there are no longer any empty fields. After there are no longer any empty fields that are capable of being filled, the data from subsequent force plate assemblies of the force plate modules 1700 are simply not included in the combined data collection. As such, the first data combination scheme does not have a fallback strategy (i.e., data fields are filled on a first come, first served basis without fallback). Fallback strategies are needed when there are more loaded, active elements (e.g., loaded force plate assemblies) than data fields. For data combination scheme (ii) above, the oldest field's data is dropped when no empty data fields are remaining. For example, when there are three (3) elements (e.g., force plate assemblies) that are consecutively loaded in series, and there are only two data fields that are capable of being filled, the data corresponding to the first (oldest) element (e.g., force plate assembly) in the series is dropped when the data corresponding to the third (newest) loaded element is added to the plurality of data fields. As such, in the data combination scheme (ii), only the data corresponding to the second and third loaded elements (e.g., second and third loaded force plate assemblies) remain in the data packet containing the data fields. For data combination scheme (iii) above, the data packet is provided with an overflow field, and any subsequent loaded elements (e.g., force plate assemblies) in the series that do not have an available data field are added to the overflow field. For example, the combined data packet being used in conjunction with four (4) loaded elements (e.g., force plate assemblies) connected in series may comprise two regular data fields and one overflow data field. The loads corresponding to the first two loaded elements (e.g., force plate assemblies) in the series respectively fill the first and second regular data fields in the data packet. Because there are no remaining regular data fields left after they are filled by the first two loaded elements (e.g., force plate assemblies) in the series, the loads corresponding to the last two loaded elements (e.g., force plate assemblies) in the series are additively combined in the overflow field. As such, the data of the last two loaded elements is still retained in the combined data packet. For data combination scheme (iv) above, the lowest load in the series is dropped based upon some metric. For example, the combined data packet being used in conjunction with three (3) loaded elements (e.g., force plate assemblies) connected in series may comprise two available data fields. The loads of the two elements (e.g., force plate assemblies) in the series having the two highest load values are retained, while the load of the element (e.g., force plate assembly) in the series having the lowest load value is dropped. As such, in the data combination scheme (iv), only the load data corresponding to the two highest load values is retained in the data packet, while the load data corresponding to the lowest of the load values is not retained in the data packet. A variety of different metrics may be used to determine the lowest load that is dropped. For example, the metric may comprise an overall vector magnitude or the magnitude of one element of the vector (magnitude of the x-component of the vector, magnitude of the y-component of the vector, etc.).

It is readily apparent that the embodiments of the force measurement system with the modular configuration described above offer numerous advantages and benefits. The aforedescribed modular force measurement system is easy to install, and is readily adaptable to different building space configurations (i.e., the force measurement system is easily scalable for different room sizes and geometries). Also, because the plurality of force measurement assemblies of the force plate module are mounted on a common base at the factory, the plurality of force measurement assemblies are capable of being accurately aligned with one another. As such, when installed on site, it is only necessary to attach the individual force plate modules to one another in order to form the overall force plate array (e.g., by using the alignment/securement devices described above). Thus, the force measurement system is capable of being easily deployed on site by simply attaching the individual force plate modules to one another. In addition, because the embodiments of the force measurement system described above incorporate redundant power and data connections, the reliability of the force measurement system is greatly increased.

In accordance with another illustrative embodiment of the measurement and testing system described herein, the measurement and testing system is configured and arranged so as to allow a system user to preselect force plates of a force plate array that form a virtual force plate prior to the collection of load output data using the force plate array. In this illustrative embodiment, the measurement and testing system includes a plurality of force measurement assemblies (e.g., the force plate assemblies described above in conjunction with FIG. 38 and FIGS. 44-49), one or more input devices (e.g., a mouse, keyboard, and/or touchscreen user interface), and a data processing device (e.g., the computing device 1740 described above) operatively coupled to the one or more input devices and each of the force transducers of each of the force plate assemblies. In this illustrative embodiment, the one or more input devices are configured to output one or more signals comprising input data indicative of which of the plurality of force plate assemblies are to be combined with one another, and the data processing device is configured and arranged to receive the one or more signals outputted by the one or more input devices and to form a virtual force measurement assembly comprising a subset of the plurality of force measurement assemblies based upon the input data of the one or more signals. Also, in this illustrative embodiment, the measurement and testing system further comprises a visual display device having an output screen (e.g., the visual display device 1530 described above in conjunction with FIG. 38). The visual display device is configured to display one or more images on the output screen so that the one or more images are viewable by a system user.

Figure 54:
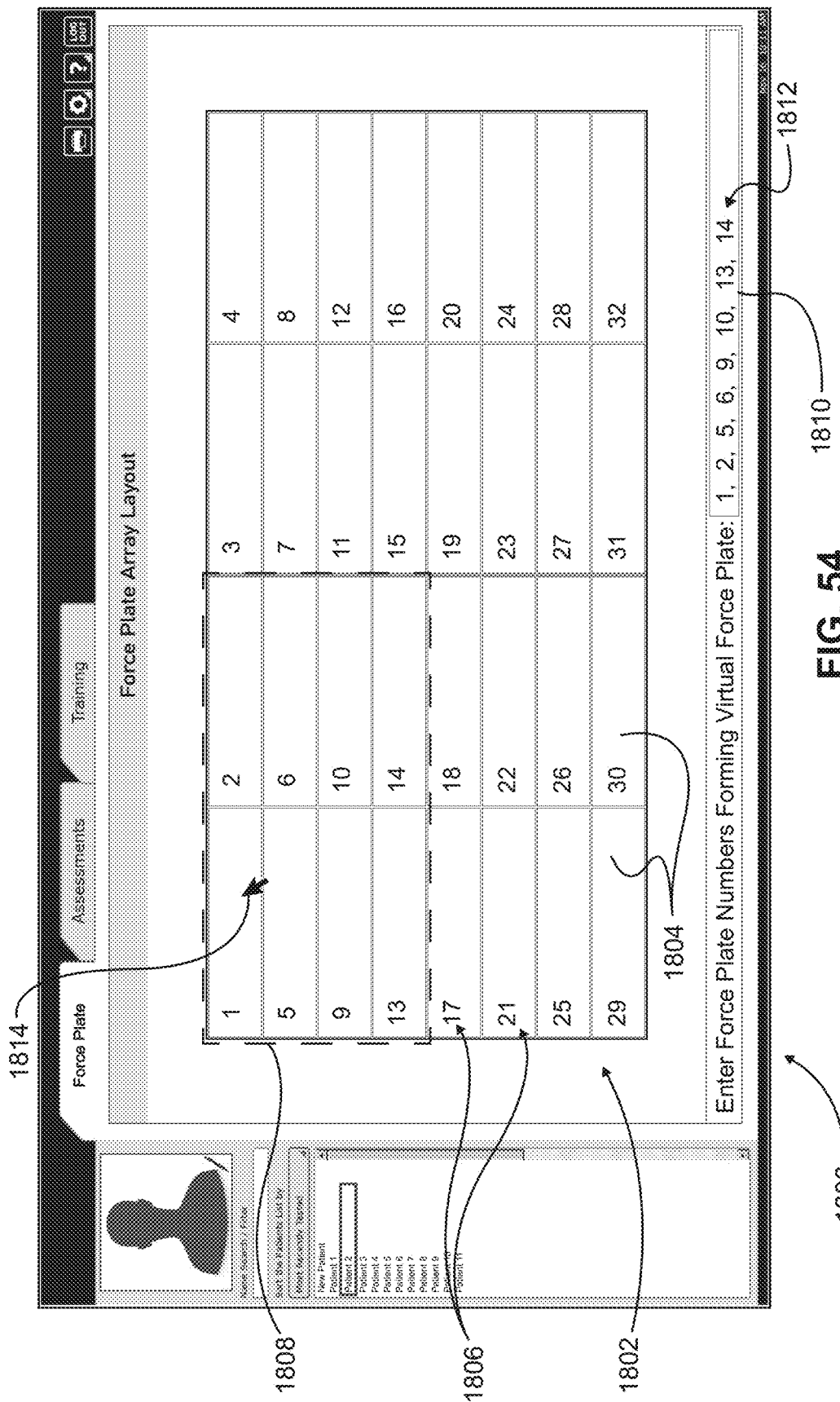
FIG. 54 is a screenshot displayed on the operator visual display device of the measurement and testing system illustrating a graphical representation of a force plate array so that force plates of the array forming a virtual force plate may be selected by a user, according to an embodiment of the invention.

With particular reference to FIG. 54, in the illustrative embodiment, it can be seen that the data processing device of the measurement and testing system is configured and arranged to generate a screen image 1800 on the visual display device that generally includes a graphical representation of a force plate array 1802 and a dialogue box 1810 for entering force plate identification numbers for the selected ones of the force plate assemblies. As shown in FIG. 54, the graphical representation of the force plate array 1802 comprises a plurality of individual force plates 1804 with identification numbers 1806 on each of the force plates 1804. The subset of force plates 1804 selected by the system user to form the virtual force measurement assembly are encircled by a dashed outline 1808 in FIG. 54.

In the illustrative embodiment, the one or more input devices may include a keyboard (i.e., keyboard 1526 in FIG. 38) configured to output one or more signals with the input data in response to a manipulation of the keyboard by the system user. As shown in the screenshot of FIG. 54, the dialog box 1810 enables the system user to specify designated ones of the plurality of force plate assemblies 1804 forming the virtual force measurement assembly 1808 by entering force plate numbers 1812 into the dialog box 1810 by using the keyboard.

In the illustrative embodiment, the one or more input devices also may include a mouse (i.e., mouse 134 in FIG. 1) configured to output one or more signals with the input data in response to a manipulation of the mouse by the system user. As shown in the screenshot of FIG. 54, the graphical representation of the force plate array 1802 enables the system user to specify designated ones of the plurality of force plate assemblies 1804 forming the virtual force measurement assembly 1808 by manipulating the mouse so as to place the selector arrow 1814 on the desired ones of the force plate assemblies 1804, and then selecting the force plate assemblies 1804 for inclusion in the virtual force measurement assembly 1808 by clicking one of the buttons on the mouse.

In the illustrative embodiment, the one or more input devices additionally may include a touchscreen user interface (i.e., a touchscreen user interface of the visual display device) configured to output one or more signals with the input data in response to a manipulation of the touchscreen user interface by the system user. As shown in the screenshot of FIG. 54, the graphical representation of the force plate array 1802 enables the system user to specify designated ones of the plurality of force plate assemblies 1804 forming the virtual force measurement assembly 1808 by touching the locations of the desired ones of the force plate assemblies 1804 on the output screen of the touchscreen user interface.

In the illustrative embodiment, the input device and the data processing device may each be part of a single digital device (e.g., a laptop computing device, a tablet computing device, or a smartphone). In one or more alternative embodiments, the data processing device and the input device may be separate components that are operatively coupled to one another (e.g., a desktop type computing system including a main housing with a central processing unit (CPU), a remote monitor, a remote keyboard, and a remote mouse, as depicted in FIGS. 1 and 35).

Figure 55:
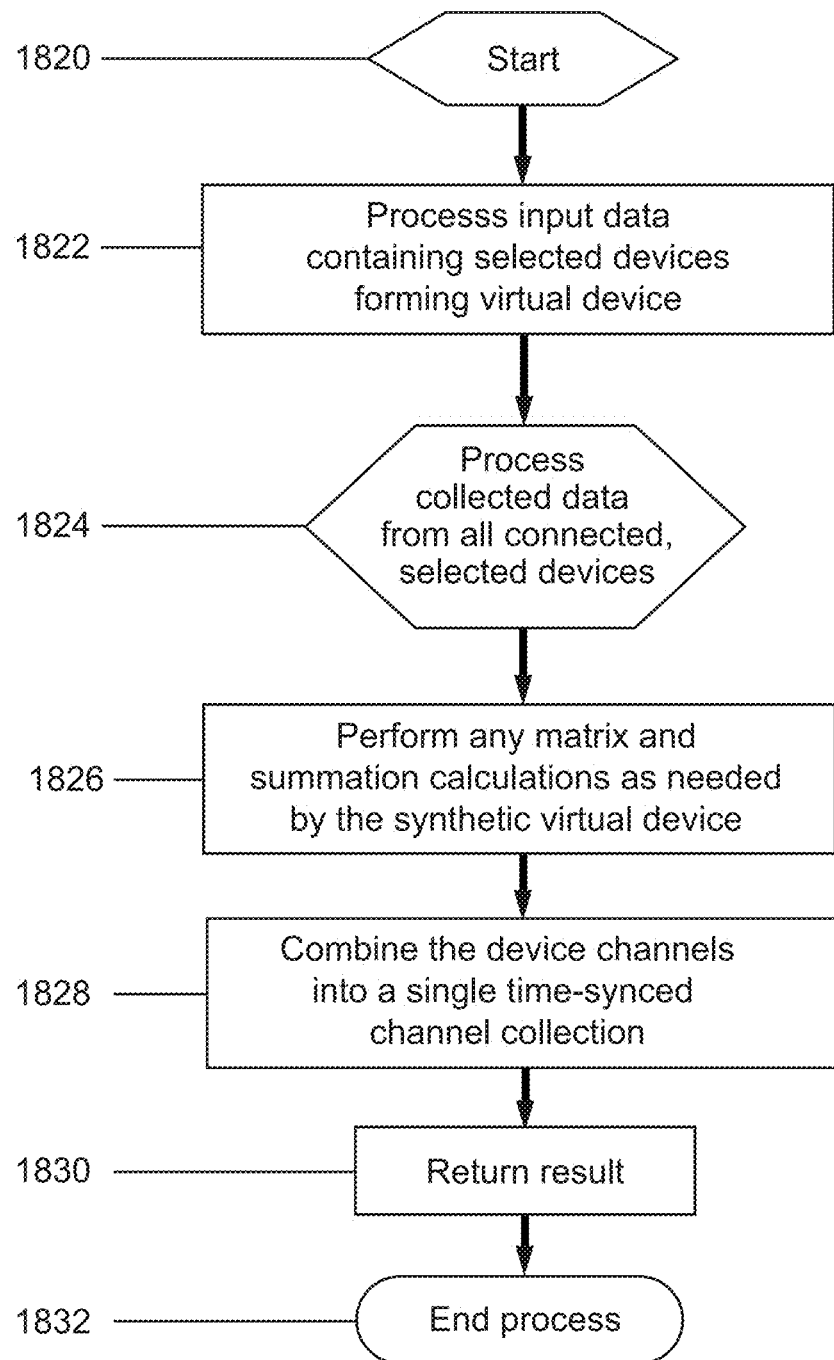
FIG. 55 is a flowchart illustrating the procedure by which output data from selected force plates forming the virtual force plate of the force plate array is combined by the data processing device.

In accordance with the aforedescribed illustrative embodiment, a flowchart illustrating the procedure by which output data from selected force plate assemblies 1804 forming the virtual force measurement assembly 1808 is combined will be described with reference to FIG. 55. All of the steps described below with reference to the flowchart of FIG. 55 are carried out by the data processing device of the measurement and testing system. Referring to FIG. 55, the procedure commences at 1820, and in step 1822, the input data from the one or more input devices is processed by the data processing device so as to determine the selected devices forming the virtual force measurement assembly 1808. In the illustrative embodiment, the data processing device is configured to form the virtual force measurement assembly 1808 using the input data of the one or more signals from the input device prior to generating the load output data from the measurement signals of the selected force plate assemblies 1804 so that load output from inactive force plate assemblies is not required to be generated by the data processing device. Then, in step 1824, collected data from all connected, selected devices (i.e., selected force plate assemblies 1804) is processed by the data processing device. In one embodiment, selected force plate assemblies 1804 are used to collect data from a subject or patient disposed thereon. In this embodiment, after the data processing device receives a plurality of voltage signals (i.e., a plurality of channels of data) from the selected force plate assemblies 1804, it initially transforms the signals into output force and moment components by multiplying the voltage signals by a calibration matrix. For example, the voltage output signals received from each of the selected force plate assemblies 1804 are transformed into the vertical force components $F_Z$ exerted on the plates of the assembly by the feet of the subject, the moment component about the x axis $M_X$ exerted on the plates of the assembly by the feet of the subject, and the moment component about the y axis $M_Y$ exerted on the plates of the assembly by the feet of the subject. Next, with reference again to FIG. 55, it can be seen that, in step 1826, any matrix and summation calculations are performed by the data processing device as needed by the synthetic virtual device (i.e., the virtual force measurement assembly 1808). For example, similar to those described above in conjunction with the embodiment of FIGS. 34-37, the channels of data from the selected force plate assemblies 1804 may be summed into a synthetic channel if required, and matrix rotation may be used to correct for the actual orientation of the selected force plate assemblies 1804 in the force plate array 1802. Then, in step 1828 of FIG. 55, the device channels of the selected force plate assemblies 1804 may be combined into a single time-synced channel collection. That is, in the illustrative embodiment, the data processing device may be configured to generate the load output data by combining the signals of the subset of the plurality of force plate assemblies 1804 forming the virtual force measurement assembly 1808 by combining the signals of the subset of the plurality of force plate assemblies 1804 forming the virtual force measurement assembly 1808 into a single time-synced synthetic channel. The time-syncing of the output data will be described in further detail hereinafter. Once the final computed result (e.g., the overall vertical force and moment components $F_{Z\_VP}$, $M_{X\_VP}$, $M_{Y\_VP}$) is returned in step 1830, the process ends at step 1832.

Figure 56:
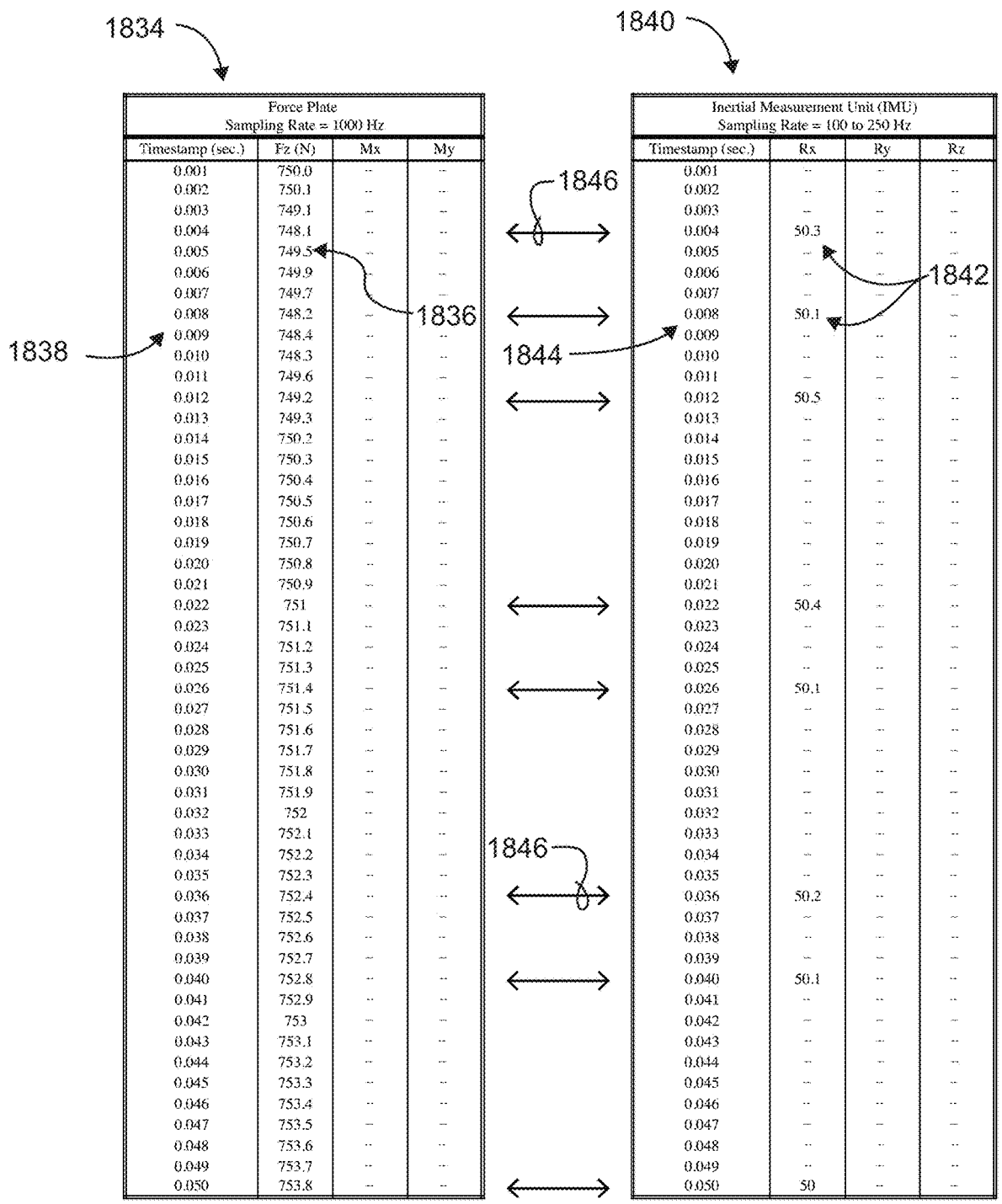
FIG. 56 illustrates an example of data time-syncing carried out by the measurement and testing system described herein, according to an embodiment of the invention.

In accordance with yet another illustrative embodiment of the measurement and testing system described herein, the data processing device of the measurement and testing system is configured and arranged to synchronize data sets with different sampling rates or different sampling frequencies by using timestamp syncing. In this illustrative embodiment, the measurement and testing system includes a first measurement device (e.g., a force plate) and a second measurement device (e.g., an inertial measurement unit (IMU)). The first measurement device has a first sampling rate (e.g., 1,000 Hertz), and the first measurement device is configured to sense one or more measured quantities and output one or more first measurement signals that are representative of the one or more measured quantities. As illustrated in table 1834 of FIG. 56, the one or more first measurement signals comprise a first plurality of data values (i.e., vertical force values 1836 ($F_Z$) in table 1834) with corresponding first timestamps (i.e., timestamps 1838 in table 1834) associated with each of the first plurality of data values 1836. The second measurement device has a second sampling rate (e.g., 100 to 250 Hertz) that is different than the first sampling rate of the first measurement device, and the second measurement device is configured to sense one or more measured quantities and output one or more second measurement signals that are representative of the one or more measured quantities. As illustrated in table 1840 of FIG. 56, the one or more second measurement signals comprise a second plurality of data values (i.e., x position values 1842 ($R_X$) in table 1840) with corresponding second timestamps (i.e., timestamps 1844 in table 1840) associated with each of the second plurality of data values 1842. In this illustrative embodiment, the measurement and testing system further includes a data processing device (i.e., a computing device) operatively coupled to the first measurement device (i.e., the force plate) and the second measurement device (i.e., the IMU). The data processing device is configured to receive the one or more first measurement signals from the first measurement device (i.e., the force plate) and the one or more second measurement signals from the second measurement device (i.e., the IMU). As illustrated in FIG. 56, the data processing device further is configured to synchronize each of the first plurality of data values 1836 with each of the second plurality of data values 1842 by determining which of the first timestamps 1838 correspond to the second timestamps 1844. In particular, as diagrammatically indicated by the arrows 1846, the data values 1842 in table 1840 are aligned with the data values 1836 in table 1834 that correspond to the same point in time by matching the corresponding timestamps 1838, 1844 of the data values 1836, 1842.

In the illustrative example of FIG. 56, the first sampling rate or frequency (i.e., 1,000 Hertz) of the force plate is greater than the second sampling rate or frequency (i.e., 100 to 250 Hertz) of the inertial measurement unit (IMU). Also, in the illustrative example of FIG. 56, the second sampling rate or frequency of the inertial measurement unit (IMU) is variable over time (i.e., the sampling frequency varies between 100 Hertz and 250 Hertz over time). In other alternative embodiments, the first measurement device may be in form of a different device with a sampling rate or frequency that is less than the sampling rate or frequency of the second measurement device. Also, the second measurement device may be in form of a different measurement device with a constant sampling frequency, rather than a variable sampling rate or frequency.

Also, in the illustrative embodiment, the data processing device may be further configured to fill-in missing data values for the second measurement device (i.e., the IMU), which has the lower sampling frequency. According to a first technique, the data processing device may be configured to duplicate data values until a new data sample is acquired from the second measurement device. For example, in the table 1840 of FIG. 56, it can be seen that there are no $R_X$ values corresponding to the timestamps of 0.005, 0.006, and 0.007 seconds. To fill-in these missing values, the data processing device may be configured to duplicate the $R_X$ value of 50.3 for the 0.005, 0.006, and 0.007 second timestamp values. The duplication of the $R_X$ value would cease at the timestamp of 0.008 seconds, where the new $R_X$ value of 50.1 is acquired. Then, to fill-in the missing values for the timestamps of 0.009, 0.010, and 0.011 seconds, the data processing device may be configured to duplicate the $R_X$ value of 50.1 until the new $R_X$ value of 50.5 is acquired at 0.012 seconds. In accordance with the first technique, this pattern for completing missing data values would continue for the entire data sample in FIG. 56.

According to a second technique for filling-in missing data values for a device having a lower sampling rate, the data processing device may be configured to employ a fractional delay technique together with interpolation. In the illustrative embodiment, the fractional delay technique, which may be based on a three-term Blackman Harris window, may delay the data up to 4.875 milliseconds in order to allow the interpolation to be performed during real-time data processing. In the illustrative embodiment, the interpolation performed by the data processing device may comprise linear interpolation, polynomial interpolation, or another suitable interpolation technique. For example, in the table 1840 of FIG. 56, it can be seen that there are no $R_X$ values corresponding to the timestamps of 0.023, 0.024, and 0.025 seconds. To fill-in these missing values, the data processing device may be configured to perform a linear interpolation technique in order to fill-in the missing values between the $R_X$ value of 50.4 at 0.022 seconds and the $R_X$ value of 50.1 at 0.026 seconds. Then, to fill-in the missing values for the timestamps between 0.027 and 0.035 seconds, the data processing device may be configured to perform another linear interpolation technique in order to fill-in the missing values between the $R_X$ value of 50.1 at 0.026 seconds and the $R_X$ value of 50.2 at 0.036 seconds. In accordance with the second technique, this pattern for completing missing data values would continue for the entire data sample in FIG. 56.

In a further illustrative embodiment, a secondary time base is utilized in order to facilitate the syncing of a primary measurement device with one or more secondary measurement devices. In this further illustrative embodiment, there is a low resolution and a high resolution version of the system. In general, the low resolution version estimates a series of discrete data points for synchronizing two measurement systems with different sampling frequencies, whereas the high resolution version estimates a continuous data curve for synchronizing two measurement systems with different sampling frequencies.

Figure 57:
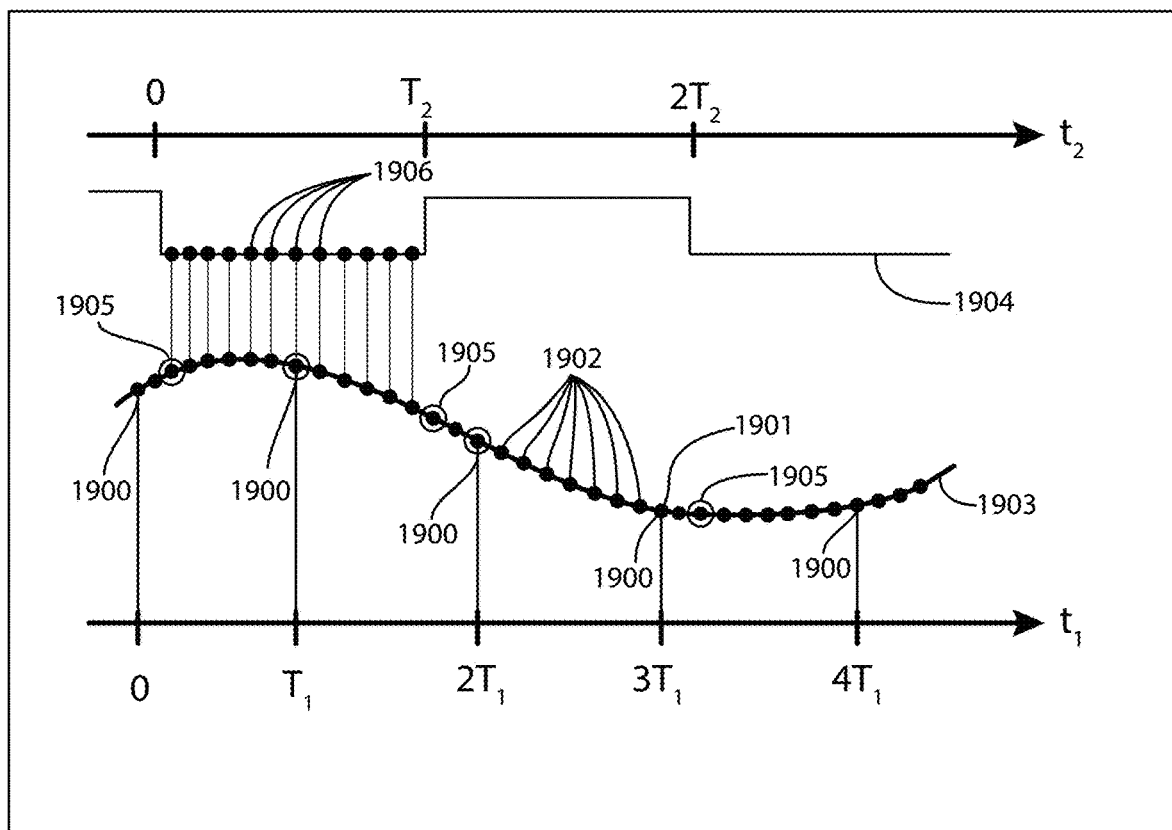
FIG. 57 illustrates an exemplary incoming signal curve and digital time reference signal depicting re-sampling using a particular timebase for an illustrative low resolution data acquisition system.

Now, turning to FIGS. 57 and 58, the low resolution version of the system of this further illustrative embodiment will be described. Initially, the microcontroller of the primary measurement device is configured and arranged to take a data sample that is sampled at a fixed primary sampling period ($T_1$) from the sensors of the primary measurement device (e.g., the force transducers of a force measurement device). For example, if the primary measurement device is a force plate, the primary sampling frequency may be 1000 Hz, thus the sampling period $T_1$ would be 0.001 seconds. Referring to FIG. 57, it can be seen that the incoming sample S(t) 1903 is sampled using the time base $t_1$ with the sampling period $T_1$. As shown in FIG. 57, the sample 1903 is sampled at the discrete sampling points 1900. Then, the microcontroller of the primary measurement device is configured and arranged to sample a digital time reference signal 1904 (i.e., a binary time reference signal) with secondary time base $t_2$ at a sampling period $T_2$. In FIG. 57, exemplary sampling points 1906 are shown. After the data samples are taken, the data samples are transmitted to the data processing device (i.e., the computer) of the measurement and testing system.

Figure 58:
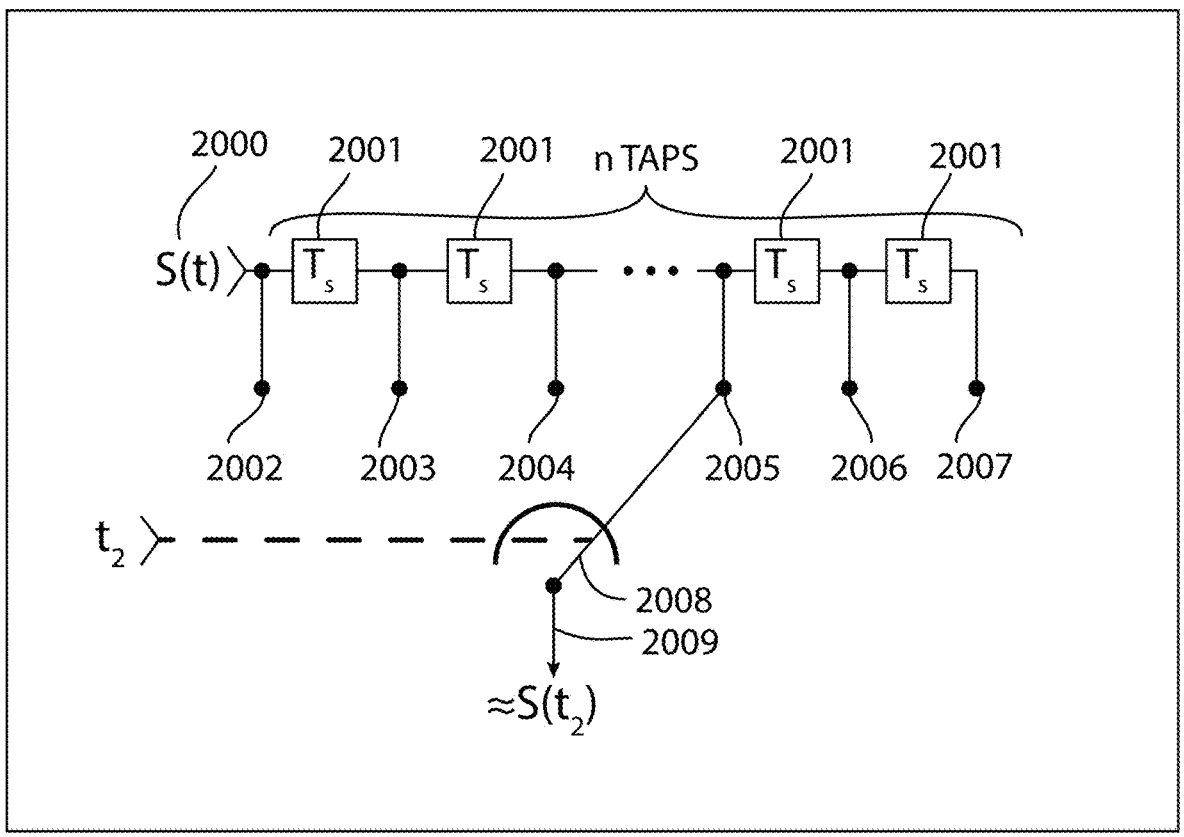
FIG. 58 illustrates an exemplary signal flow diagram for the illustrative low resolution data acquisition system.

Then, with reference to the exemplary signal flow diagram of FIG. 58, the data processing device of the measurement and testing system computes time-delayed values of the data sample S(t) 2000 that is sampled at time t with the fixed primary sampling period $T_1$. In FIG. 58, each element 2001 denotes an n element of an n-element digital delay line, each element 2001 delays by a time $T_S$. In the exemplary signal flow diagram of FIG. 58, the first delay line tap S(t) is denoted by tap line 2002, the second delay line tap $S(t-T_S)$ is denoted by tap line 2003, the third delay line tap $S(t-2\,T_S)$ is denoted by tap line 2004, the n−2 delay line tap $S(t-(n-3)T_S)$ is denoted by tap line 2005, the n−1 delay line tap $S(t-(n-2)T_S)$ is denoted by tap line 2006, and the n delay line tap $S(t-(n-1)T_S)$ is denoted by tap line 2007. In FIG. 58, the selector switch 2008 picks up the value $S(t+iT_S)$ at the time closest to $t_2$ so as to compute an approximate value $S(t_2)$ 2009. In the illustrative embodiment, the delay "taps" used to generate the time delay are interdependent (i.e., it is not possible to just compute some of the delay "taps", all of the delay "taps" must be computed). These time-delayed values can be computed using linear interpolation, polynomial interpolation, etc. In the illustrative embodiment, the time delay is needed for the prediction of the points because the time delay values are being computed "on the fly" by the system.

Next, referring again to FIGS. 57 and 58, the time-delayed values of the data samples are selected such that they occur coincident with a chosen transition of the digital time reference signal 1904. The user-selectable transitions can be up, down, or both (e.g., up may be 0 to 1, and down may be 1 to 0). That is, the data processing device of the measurement and testing system is programmed to select time-delayed values that occur coincident with a chosen transition of the digital time reference signal 1904. In this step, only some of the computed time-delayed values are chosen for use (e.g., based on the selected transition). The other computed values are not used. For example, referring to FIG. 57, if the selector 2008 in FIG. 58 selects the time-delayed value 1905 based upon a "down" transition of the digital time reference signal 1904, the outputs of the delay line taps for the sample 1901 (i.e., $S(t)=S(3\ T_1)$) would be the points 1902 in FIG. 57. In this example, the closest data point of the sample $S(t)$ 1903 is the point 1901 in FIG. 57. Finally, the data processing device of the measurement and testing system sends the computed time-delayed values to another user device (i.e., a secondary measurement device or system, such as a motion capture system) that is sampling some other data using the digital time reference signal 1904 as a time base. Advantageously, the data generated by the primary measurement device (e.g., the force transducers of a force measurement device) is able to be synchronized with the secondary measurement device or system (e.g., the motion capture system) by means of the computed time delay values. That is, when the secondary measurement device or system has a higher sampling frequency than the primary measurement device, the computed time delay values fill-in the missing data values between the acquired sampled points of the primary measurement device so that there is one-to-one correspondence between the data values of the primary and secondary measurement devices.

Figure 59:
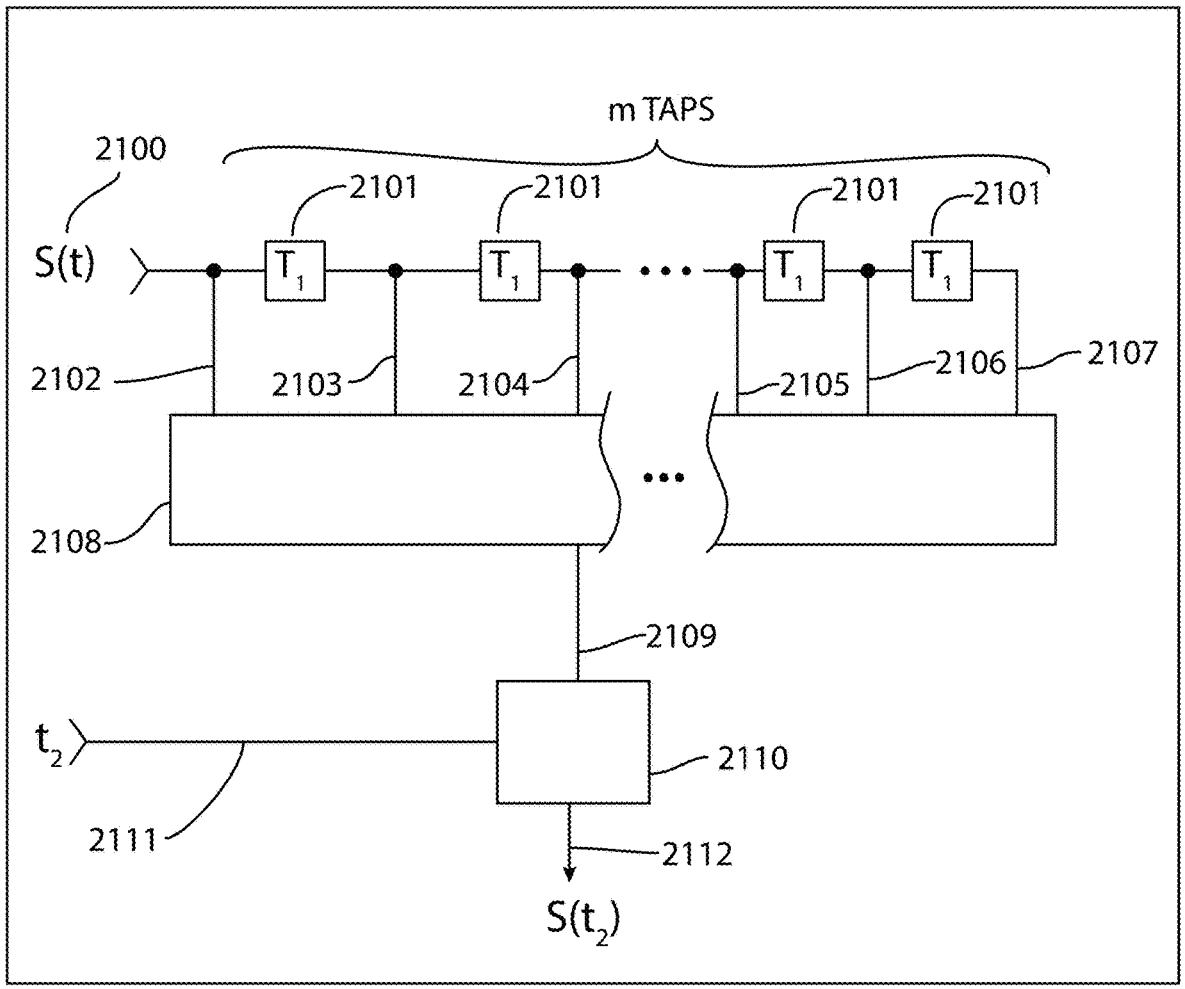
FIG. 59 illustrates an exemplary signal flow diagram for an illustrative high resolution data acquisition system.
Figure 60:
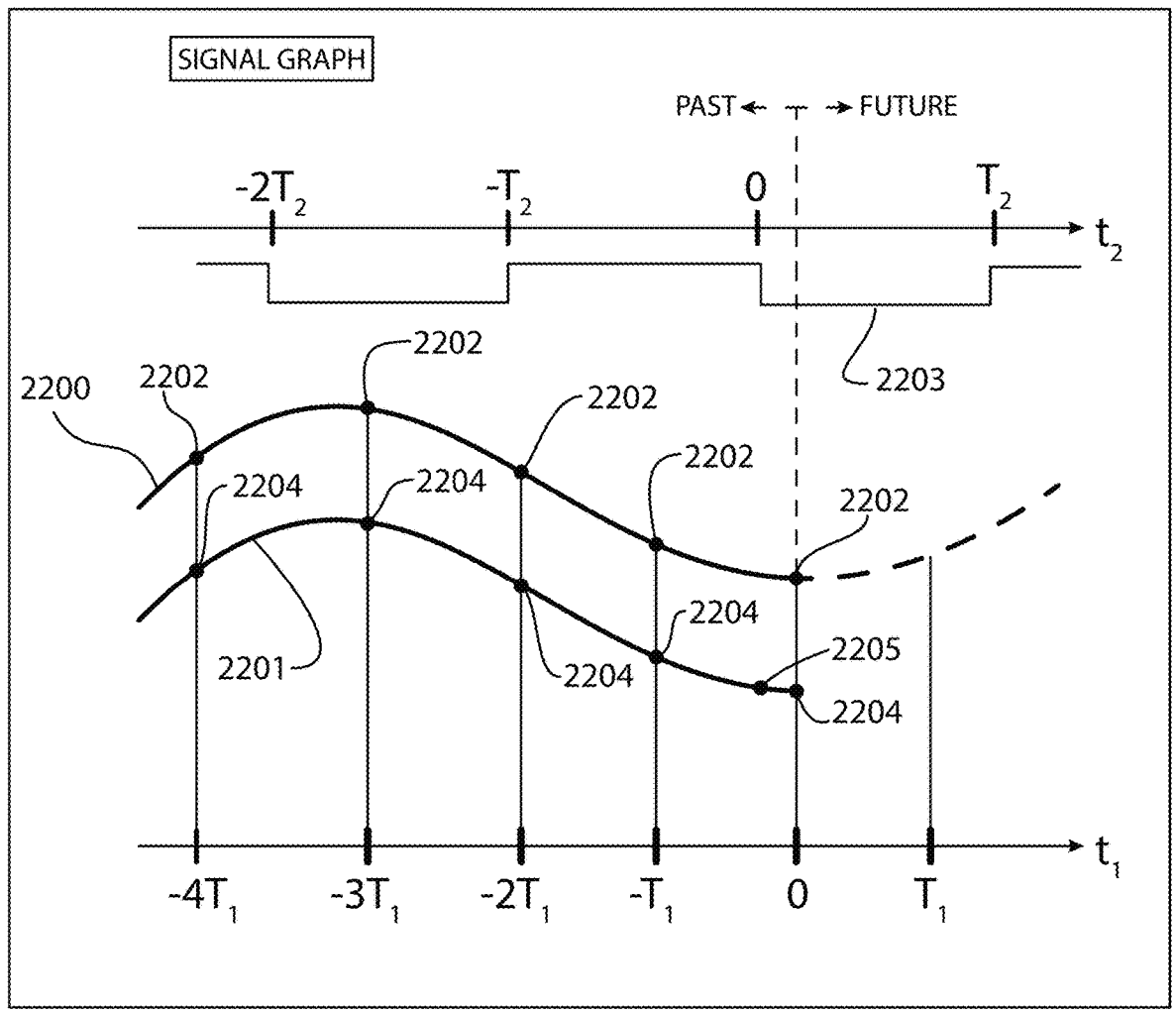
FIG. 60 illustrates an exemplary incoming signal curve and digital time reference signal depicting sampling using a particular timebase for the illustrative high resolution data acquisition system.

Now, referring to FIGS. 59 and 60, the high resolution version of the system of this further illustrative embodiment will be described. In the illustrative embodiment, the microcontroller of the primary measurement device has a primary clock measuring the passage of time in units ($T_1$). For example, in the illustrative embodiment, the passage of time may be measured in microseconds. Initially, the microcontroller of the primary measurement device (e.g., the force transducers of a force measurement device) is configured and arranged to take a data sample that is sampled at every n1 time units of the primary clock. For example, if the primary measurement device is a force plate, the primary sampling frequency may be 1000 Hz, thus the sampling period $T_1$ would be 0.001 seconds. Referring to FIG. 60, it can be seen that the incoming sample $S(t)$ 2200 is sampled using the time base $t_1$ with the sampling period $T_1$. As shown in FIG. 57, the sample 2200 is sampled at the discrete sampling points 2202. Then, the microcontroller of the primary measurement device is configured and arranged to sample a digital time reference signal 2203 (i.e., a binary time reference signal) with secondary time base $t_2$ at a sampling period $T_2$, and on every up or down transition, the microcontroller records the current time. After the data samples 2202, 2203 are taken, the data samples are transmitted to the data processing device (i.e., the computer) of the measurement and testing system.

Then, with reference again to FIGS. 59 and 60, the data processing device of the measurement and testing system calculates, for every time value of the digital time reference signal, sinc (or similar) reconstructed values 2204 of the time-continuous signal sampled at every n1 time units of the primary clock. In the exemplary signal flow diagram of FIG. 59, the reference numeral 2100 denotes the input signal sampled using the time base $T_1$ at time t, while each element 2101 denotes an m element of an m-element digital delay line, each element 2101 delaying by a time $T_1$. The determination of the elements 2101 in the signal flow diagram of FIG. 59 is trivial compared to the determination of the elements 2001 in the signal flow diagram of FIG. 58 because $S(t)$ is already sampled with period $T_1$, whereas elements 2001 had to be determined as a result of a computationally expensive fractional delay ($T_S=T_1/n$). In the exemplary signal flow diagram of FIG. 59, the first delay line tap $S(t)$ at time $t_1$ is denoted by tap line 2102, the second delay line tap $S(t-T_1)$ is denoted by tap line 2103, the third delay line tap $S(t-2T_1)$ is denoted by tap line 2104, the m−2 delay line tap $S(t-(m-3)T_1)$ is denoted by tap line 2105, the m−1 delay line tap $S(t-(m-2)T_1)$ is denoted by tap line 2106, and the m delay line tap $S(t-(m-1)T_1)$ is denoted by tap line 2107. In FIG. 59, the element 2108 denotes the interpolation function fitter. The coefficients 2109 of the interpolation function are transmitted to the interpolator 2110 in FIG. 59. In FIG. 59, the interpolated value 2112 of the signal $S(t)$ is calculated at the time value 2111 which, in the case of the illustrative example, is time $t_2$. The interpolation function fitter 2108 needs to be computed only when the interpolator 2110 needs its coefficients, and at most as often as $T_1$. The interpolator 2110 needs to be computed only when a new secondary time base $T_2$ time instant $t_2$ is available. Referring again to FIG. 60, the curve 2201 is the interpolated approximation curve that is generated using the high resolution version of the system. In contrast to the low resolution version of the system, which simply approximates discrete points 1902, the high resolution version approximates a continuous curve 2201. In FIG. 60, the interpolation nodes, which are available at the interpolation function fitter 2108, are denoted by reference numeral 2204. In the illustrative embodiment, there are a total of five (5) nodes (i.e., m=5). With reference again to FIG. 60, for the exemplary time $t_2$, the interpolated value on the continuous estimated curve 2201 is denoted by point 2205. Finally, for each of the time values associated with the time base transitions chosen by the user (the up, down, or both up and down transitions), the data processing device of the measurement and testing system sends the reconstructed values of the time-continuous signal to the user when the high resolution version of the system is employed. Advantageously, the data generated by the primary measurement device (e.g., the force transducers of a force measurement device) is able to be synchronized with the secondary measurement device or system (e.g., the motion capture system) by means of the approximated continuous curve 2201. That is, when the secondary measurement device or system has a higher sampling frequency than the primary measurement device, the data processing device uses the approximated continuous curve 2201 to fill-in the missing data values between the acquired sampled points of the primary measurement device so that there is one-to-one correspondence between the data values of the primary and secondary measurement devices.

Both the low resolution and high resolution version of the system have numerous benefits. First of all, both versions are easy to implement on low-cost microcontrollers. Low-cost microcontrollers typically provide peripherals that enable the time base signal sampling. Secondly, both the low resolution and high resolution versions result in low overhead. In the low resolution mode, there are only n additional binary bits per sample of the load signal. In the high resolution mode, there are a few multiples of ceil ($\log_2(n_1)$) bits of data (i.e., as many bits of data as the anticipated number of time base transitions within the samples of digital time reference signal).

Now, the stop-start feature of the further illustrative embodiment will be described. The stop-start feature may have two modes of operations. In the first mode of operation, the microcontroller does not send out any samples when the digital time reference signal is zero. In the second mode of operation, the microcontroller sends samples out, but tags the samples with the state of "sample enable".

Although the invention has been shown and described with respect to a certain embodiment or embodiments, it is apparent that this invention can be embodied in many different forms and that many other modifications and variations are possible without departing from the spirit and scope of this invention. Moreover, while reference is made throughout this disclosure to, for example, "an illustrative embodiment", "one embodiment" or a "further embodiment", it is to be understood that some or all aspects of these various embodiments may be combined with one another as part of an overall embodiment of the invention. Also, the compound conjunction "and/or" is used throughout this disclosure to mean one or the other, or both.

In addition, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A measurement and testing system, comprising:
a first measurement device having a first sampling rate, the first measurement device configured to sense one or more first measured quantities and output one or more first measurement signals that are representative of the one or more first measured quantities, a first sampling period of the one or more first measurement signals being an inverse of the first sampling rate;
a second measurement device having a second sampling rate that is different than the first sampling rate of the first measurement device, the second measurement device configured to sense one or more second measured quantities and output one or more second measurement signals that are representative of the one or more second measured quantities, the second measurement device being included as a part of a data collection subsystem, the data collection subsystem forming a portion of the measurement and testing system and being separate from the first measurement device;
a microcontroller configured to produce a digital time reference signal using a reference sampling period; and
a data processing device operatively coupled to the first measurement device, the second measurement device, and the microcontroller, the data processing device including at least one hardware component, and the data processing device configured to execute computer executable stored instructions, the computer executable stored instructions comprised by the data processing device and comprising instructions for:

receiving the one or more first measurement signals from the first measurement device and the digital time reference signal from the microcontroller;
computing time-delayed values of the one or more first measurement signals from the first measurement device using a time delay;
selecting particular ones of the computed time-delayed values that occur coincident with a transition of the digital time reference signal produced by the microcontroller; and
sending the particular ones of the computed time-delayed values to the data collection subsystem with the second measurement device such that the one or more first measurement signals are able to be synchronized with the one or more second measurement signals.

2. The measurement and testing system according to claim 1, wherein the digital time reference signal produced by the microcontroller is in the form of square wave signal.

3. The measurement and testing system according to claim 2, wherein the transition of the digital time reference signal comprises an up transition of the square wave signal, a down transition of the square wave signal, or both an up transition and down transition of the square wave signal.

4. The measurement and testing system according to claim 1, wherein the time delay used by the data processing device to compute the time-delayed values is based upon a predetermined fraction of the first sampling period of the one or more first measurement signals from the first measurement device.

5. The measurement and testing system according to claim 1, wherein the reference sampling period of the digital time reference signal produced by the microcontroller is fractionally proportionate to the first sampling period of the first measurement device.

6. The measurement and testing system according to claim 1, wherein the transition of the digital time reference signal determined by the data processing device comprises an increase in the digital time reference signal, a decrease in the digital time reference signal, or both an increase in the digital time reference signal and a decrease in the digital time reference signal.

7. A measurement and testing system, comprising:
a first measurement device having a first sampling rate, the first measurement device configured to sense one or more first measured quantities and output one or more first measurement signals that are representative of the one or more first measured quantities;
a second measurement device having a second sampling rate that is different than the first sampling rate of the first measurement device, the second measurement device configured to sense one or more second measured quantities and output one or more second measurement signals that are representative of the one or more second measured quantities, the second measurement device being included as a part of a data collection subsystem, the data collection subsystem forming a portion of the measurement and testing system and being separate from the first measurement device;
a microcontroller configured to sample a digital time reference signal on each of one or more transitions of the digital time reference signal and record time values; and
a data processing device operatively coupled to the first measurement device, the second measurement device, and the microcontroller, the data processing device including at least one hardware component, and the data processing device configured to execute computer executable stored instructions, the computer executable stored instructions comprised by the data processing device and comprising instructions for:
- receiving the one or more first measurement signals from the first measurement device and the digital time reference signal from the microcontroller;
- computing, for each of the time values determined by the microcontroller, a reconstructed value of the one or more first measurement signals outputted by the first measurement device; and
- sending the computed reconstructed values to the data collection subsystem with the second measurement device for each transition of the digital time reference signal such that the one or more first measurement signals are able to be synchronized with the one or more second measurement signals.

8. The measurement and testing system according to claim 7, wherein the digital time reference signal sampled by the microcontroller is in the form of square wave signal.

9. The measurement and testing system according to claim 8, wherein the transition of the digital time reference signal comprises an up transition of the square wave signal, a down transition of the square wave signal, or both an up transition and down transition of the square wave signal.

10. The measurement and testing system according to claim 7, wherein the reconstructed values computed by the data processing device comprise reconstructed values determined using interpolation.

11. The measurement and testing system according to claim 7, wherein the transition of the digital time reference signal determined by the data processing device comprises an increase in the digital time reference signal, a decrease in the digital time reference signal, or both an increase in the digital time reference signal and a decrease in the digital time reference signal.

* * * * *